United States Patent
Fukui et al.

(10) Patent No.: US 11,311,523 B2
(45) Date of Patent: *Apr. 26, 2022

(54) PYRIDINONE COMPOUND AND USE THEREOF

(71) Applicant: KYUSHU UNIVERSITY, NATIONAL UNIVERSITY CORPORATION, Fukuoka (JP)

(72) Inventors: Yoshinori Fukui, Fukuoka (JP); Takehito Uruno, Fukuoka (JP)

(73) Assignee: KYUSHU UNIVERSITY, NATIONAL UNIVERSITY CORPORATION, Fukuoka (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/517,385

(22) Filed: Jul. 19, 2019

(65) Prior Publication Data

US 2020/0061039 A1 Feb. 27, 2020

Related U.S. Application Data

(62) Division of application No. 15/553,762, filed as application No. PCT/JP2016/055927 on Feb. 26, 2016, now Pat. No. 10,406,141.

(30) Foreign Application Priority Data

Feb. 27, 2015 (JP) .............................. JP2015-039071

(51) Int. Cl.
| | | |
|---|---|---|
| A61K 31/4412 | (2006.01) | |
| A61P 35/04 | (2006.01) | |
| A61K 45/00 | (2006.01) | |
| A61K 31/4439 | (2006.01) | |
| A61K 31/444 | (2006.01) | |
| A61K 31/4453 | (2006.01) | |
| A61K 31/5377 | (2006.01) | |
| A61K 31/541 | (2006.01) | |
| A61K 31/55 | (2006.01) | |

(Continued)

(52) U.S. Cl.
CPC ........ *A61K 31/4412* (2013.01); *A61K 31/444* (2013.01); *A61K 31/4439* (2013.01); *A61K 31/4453* (2013.01); *A61K 31/5377* (2013.01); *A61K 31/541* (2013.01); *A61K 31/55* (2013.01); *A61K 45/00* (2013.01); *A61P 35/00* (2018.01); *A61P 35/04* (2018.01); *G01N 33/15* (2013.01); *G01N 33/50* (2013.01); *G01N 33/5011* (2013.01)

(58) Field of Classification Search
None
See application file for complete search history.

(56) References Cited

U.S. PATENT DOCUMENTS

| | | | |
|---|---|---|---|
| 7,541,153 B2* | 6/2009 | Fukui ................... | G01N 33/564 435/7.1 |
| 10,406,141 B2* | 9/2019 | Fukui ................. | A61K 31/5377 |

(Continued)

FOREIGN PATENT DOCUMENTS

| | | |
|---|---|---|
| CA | 2726588 A1 | 12/2009 |
| JP | S51-143667 A | 12/1976 |

(Continued)

OTHER PUBLICATIONS

Kunisaki et al., "DOCK2 is a Rac activator that regulates motility and polarity during neutrophil chemotaxis", 2006, The Journal of Cell Biology, 174(5), pp. 647-652. (Year: 2006).*

(Continued)

*Primary Examiner* — My-Chau T. Tran
(74) *Attorney, Agent, or Firm* — Kratz, Quintos & Hanson, LLP

(57) ABSTRACT

The present invention provides a compound capable of being used as an active ingredient of an anti-cancer agent. To provide an anti-cancer agent with few side effects, an object of the present invention is to provide a compound capable of selectively inhibiting the target, i.e., DOCK1, or a salt thereof. The pyridinone compound of the present invention is represented by Formula (1):

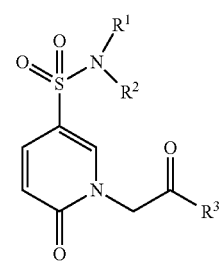

(1)

wherein $R^1$ and $R^2$ are the same or different, and each represents $C_{1-6}$ alkyl; and
$R^3$ is a group represented by, for example, Formula (3) below

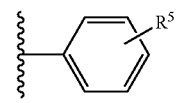
(3)

wherein $R^5$ in the group represented by Formula (3) is hydrogen.

17 Claims, 25 Drawing Sheets

(51) Int. Cl.
G01N 33/50 (2006.01)
A61P 35/00 (2006.01)
G01N 33/15 (2006.01)

(56) References Cited

U.S. PATENT DOCUMENTS

2011/0319459 A1  12/2011  Gupta
2018/0028515 A1  2/2018  Fukui

FOREIGN PATENT DOCUMENTS

| JP | 2011-522056 A1 | 7/2011 |
| WO | 2006/024823 A1 | 3/2006 |
| WO | 2008/079787 A2 | 7/2008 |
| WO | 2009/149188 A1 | 12/2009 |
| WO | 2012/157389 A1 | 11/2012 |
| WO | 2016/136985 A1 | 9/2016 |
| WO | 2018/216822 A1 | 11/2018 |

OTHER PUBLICATIONS

Sperandio et al., "Rationalizing the chemical space of protein-protein interaction inhibitors", 2010, Drug Discovery Today, 15(5/6), pp. 220-229. (Year: 2010).*
Hughes et al., "Principles of early drug discovery", 2011, British Journal of Pharmacology, 162(6), pp. 1239-1249. (Year: 2011).*
Watanabe et al., "DOCK2 and DOCK5 Act Additively in Neutrophils to Regulate Chemotaxis, Superoxide Production, and Extracellular Trap Formation", 2014, The Journal of Immunology, 193(11), pp. 5660-5667. (doi: 10.4049/jimmunol.1400885) (Year: 2014).*
International Search Report for International Application No. PCT/JP2016/055927 dated Apr. 19, 2016 (3 sheets).
H.Feng, et al.; "Phosphorylation of dedicator of cytokinesis 1(Dock180) at tyrosine residue Y722 by Src family kinases mediates EGFRvIII-driven glioblastoma tumorigensis"; PNAS; vol. 109; No. 8; Feb. 21, 2012; pp. 3018-3023 (6 sheets total)/ Cited in International Search Report dated Apr. 19, 2016.
M. Jarzynka, et al.; "ELMO1 and Dock180, a Bipartite Rac1 Guanine Nucleotide Exchange Factor, Promote Human Glioma Cell Invasion"; Cancer Research; vol. 67; No. 15; Aug. 1, 2007; pp. 7203-7211 and end sheet (10 sheets total)/ Cited in International Search Report dated Apr. 19, 2016.
M. Laurin, et al.; "Rac-specific guanine nucleotide exchange factor DOCK1 is a critical regulator of HER2-mediated breast cancer metastasis"; PNAS; vol. 110; No. 18; Apr. 30, 2013; pp. 7434-7439 (6 sheets total)/ Cited in International Search Report dated Apr. 19, 2016/ p. 2 of Specification.
F. Sanematsu, et al.; "Phosphatidic Acid-dependent Recruitment and Function of the Rac Activator DOCK1 during Dorsal Ruffle Formation"; The Journal of Biological Chemistry; vol. 288; No. 12; Mar. 22, 2013; pp. 8092-8100 and end sheet (10 sheets total)/ Cited in International Search Report dated Apr. 19, 2016/ p. 2 of Specification.
T. Owa, et al.; "Synthesis and Biological Evaluation of N-(7-Indolyl)-3-pyridinesulfonamide Derivatives as Potent Antitumor Agents"; Bioorganic & Medicinal Chemistry Letters; vol. 12; 2002; pp. 2097-2100 (4 sheets total)/ Cited in International Search Report dated Apr. 19, 2016.
C. Commisso, et al.; "Macropinocytosis of protein is an amino acid supply route in Ras-transformed cells"; Nature; vol. 497; May 30, 2013; pp. 633-638 (6 sheets total)/ p. 2 of Specification.
Y. Fukui, et al.; "Haematopoietic cell-specific CDM family protein DOCK2 is essential for lymphocyte migration" Nature; vol. 412; Aug. 23, 2001; pp. 826-831 (6 sheets total)/ p. 2 of Specification.
Partial Supplementary European Search Report for European Patent Application No. 16755729.7 dated Oct. 12, 2018 (11 pages).
G. Cardama, et al.; "Preclinical Development of Novel Rac1-GEF Signaling Inhibitors using a Rational Design Approach in Highly Aggressive Breast Cancer Cell Lines"; Anti-Cancer Agents in Medicinal Chemistry; 2014; vol. 14; No. 6; pp. 840-851 (12 pages total)/ Cited in Extended European Search Report dated Feb. 11, 2019.
X. Nishikimi, et al.; "Blockade of Inflammatory Responses by a Small-Molecule Inhibitor of the Rac Activator DOCK2"; Chemistry & Biology; 2012; vol. 19; No. 4; Apr. 20, 2012; pp. 488-497 (10 pages total)/ Cited in Extended European Search Report dated Feb. 11, 2019.
N. Bouquier, et al.; "A Cell Active Chemical GEF Inhibitor Selectively Targets the Trio/RhoG/Rac1 Signaling Pathway"; Chemistry & Biology; vol. 16; No. 6; Jun. 26, 2009; pp. 657-666 (10 pages total)/ Cited in Extended European Search Report dated Feb. 11, 2019.
Extended European Search Report for European Patent Application No. 16755729.7 dated Feb. 11, 2019 (13 pages).
Kinnings, et al.; "Drug Discovery Using Chemical Systems Biology: Repositioning the Safe Medicine Comtan to Treat Multi-Drug and Extensively Drug Resistant Tuberculosis"; PLOS Computational Biology; vol. 5(7); 2009; pp. 1-10.
Kulkarni, et al.; "Multiple Factors Confer Specific Cdc42 and Rac Protein Activation by Dedicator of Cytokinesis (DOCK) Nucleotide Exchange Factors"; The Journal of Biological Chemistry; vol. 286(28); 2011; pp. 25341-25351.
Ajay, et al.; "Identification of novel, less toxic PTP-LAR inhibitors using silico strategies: pharmacophore modeling, SADMET-based virtual screening and docking"; J. Mol. Model.; vol. 18(1); 2012; pp. 187-201.
Jungmichel, et al.; "Specificity and Commonality of the Phosphoinositide-Binding Proteome Analyzed by Quantitative Mass Spectrometry"; Cell Reports; vol. 6(3); 2014; pp. 578-591.
L. Salerno, et al.; "Potholing of the hydrophobic heme oxygenase-1 western region for the search of potent and selective imidazole-based inhibitors"; European Journal of Medicinal Chemistry; 2018; vol.;148; pp. 54-62 (9 pages).
Y. Chen, et al.; "Synthesis of novel triazole and imidazole derivatives containing biphenyl"; Chemical Research and Application; 2011; vol. 23; No. 3; pp. 302-304 (3 pages)/ English Abstract.
D. Nardi, et al.; "α-Amino-Metilchetoni, α-Amino-Etanoli E Loro Sali Quaternari A Presumibile Attivita' Farmacologica"; Bollettino Chimico Farmaceutico; 1963; vol. 102; No. 11; pp. 765-776 (12 pages)/ English Summary.
T. Hirotada, et al.; "Targeting Ras-Driven Cancer Cell Survival and Invasion through Selective Inhibition of DOCK1"; Cell Reports; 2017; vol. 19; No. 5; pp. 969-980 (12 pages).
M. Laurin, et al.; "Insights into the biological functions of Dock family guanine nucleotide exchange factors"; Genes & Development; 2014; vol. 28; pp. 533-547 (15 pages).
A. Nishikimi, et al.; "Immune regulatory functions of DOCK family proteins in health and disease"; Experimental Cell Research; 2013; vol. 319; pp. 2343-2349 (7 pages).
T. Tomino, et al.; "DOCK1 inhibition suppresses cancer cell invasion and macropinocytosis induced by self-activating Rac1 P29S mutation"; Biochemical and Biophysical Research Communications; 2018; vol. 497; pp. 298-304 (7 pages).
I. A. Prior, et al.; "A Comprehensive Survey of Ras Mutations in Cancer"; Cancer Research; 2012; vol. 72; No. 10; pp. 2457-2467 (11 pages, 1 end sheet, 12 sheets total).
A. D. Cox, et al.; "Drugging the undruggable Ras: mission possible?"; Nature Reviews Drug Discovery; 2014; vol. 13; No. 11; pp. 1-47 (47 pages).
F. Zwartkruis, et al.; "Ras and macropinocytosis: trick and treat"; Cell Research; 2013; vol. 23; pp. 982-983 (2 pages).
Office Action of corresponding Japanese Patent Application No. 2019-238590 dated Dec. 1, 2020 (3 sheets, 3 sheets translation, 6 sheets total).
A. Abu-Thuria, et al.; "Axl Phosphorylates Elmo Scaffold Proteins to Promote Rac Activation and Cell Invasion" Molecular and Cellular Biology; 2015; vol. 35; No. 1; pp. 76-87 (12 pages)/ Cited in JP-OA dated Dec. 1, 2020 for App. No. 2019-238590.
U.S. Appl. No. 17/298,540, filed May 28, 2021.
H. Tajiri, et al.; "Targeting Ras-Driven Cancer Cell Survival and Invasion through Selective Inhibition DOCK1"; Cell Reports; 2017; vol. 19; No. 5; pp. 969-980 (12 pages).

(56) References Cited

OTHER PUBLICATIONS

D. M. Allwood, et al.; Metal-Free Coupling of Saturated Heterocyclic Sulfonylhydrazones wuth Boronic Acids; The Journal of Organic Chemistry; 2014; vol. 79; pp. 328-338 (11 pages).

* cited by examiner

CPYPP

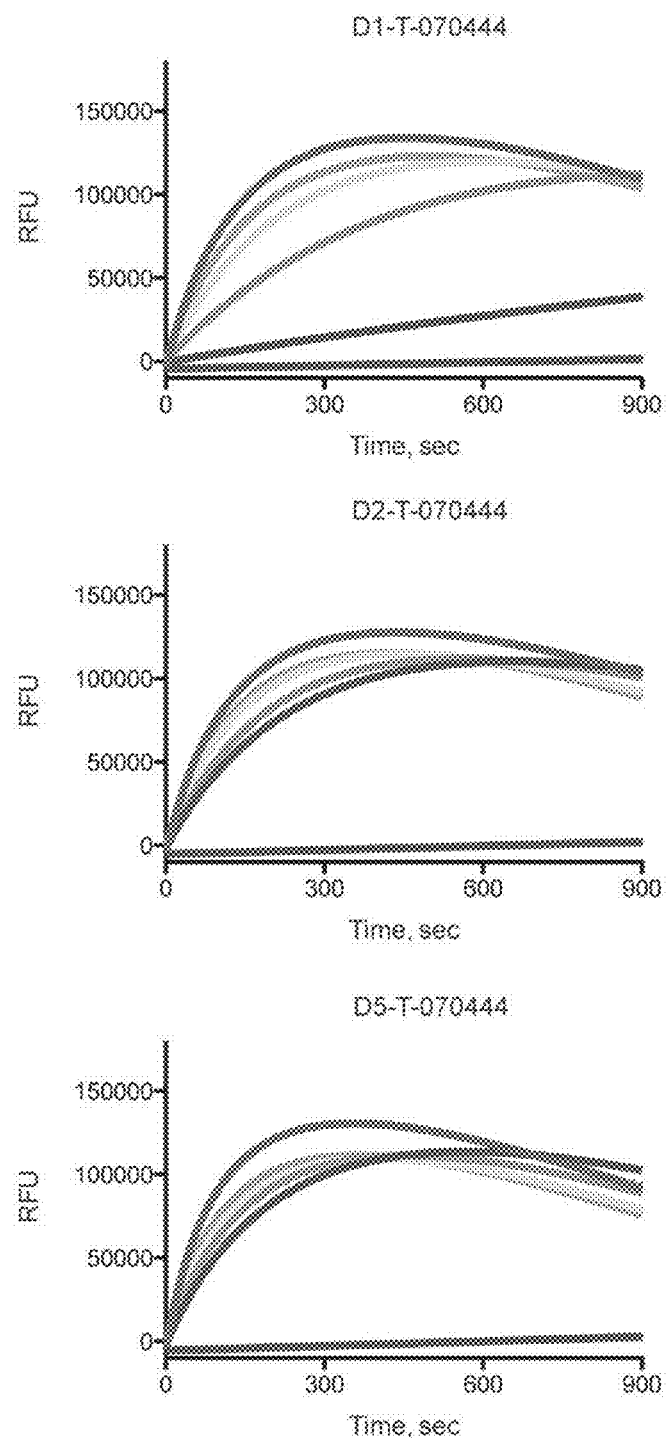
FIG. 11(B) T-070444

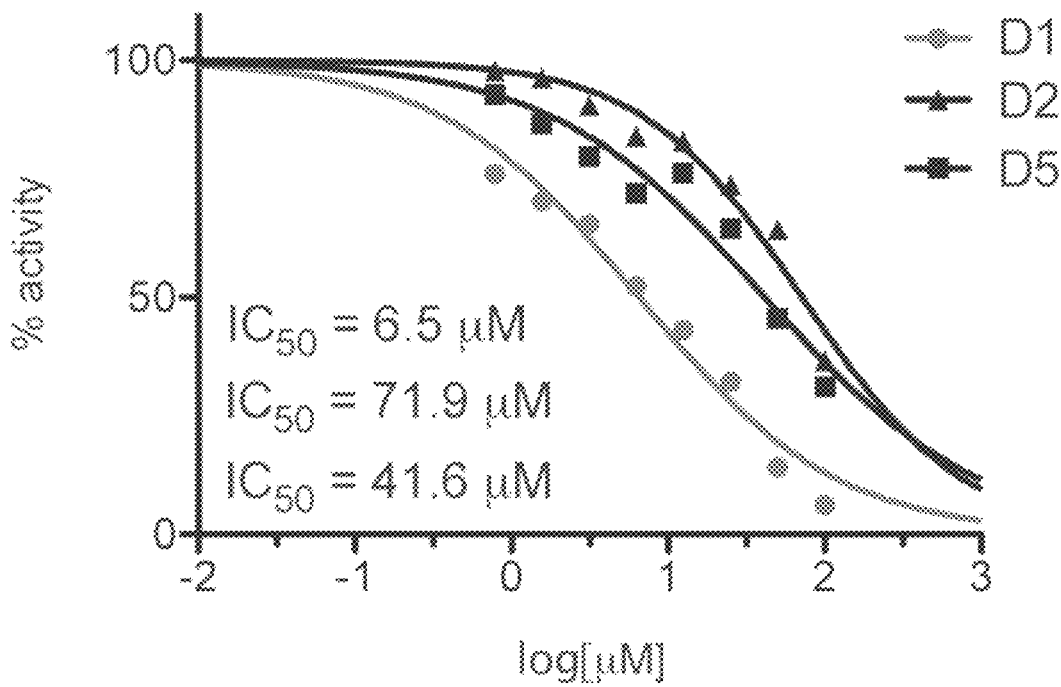
FIG. 11(F)
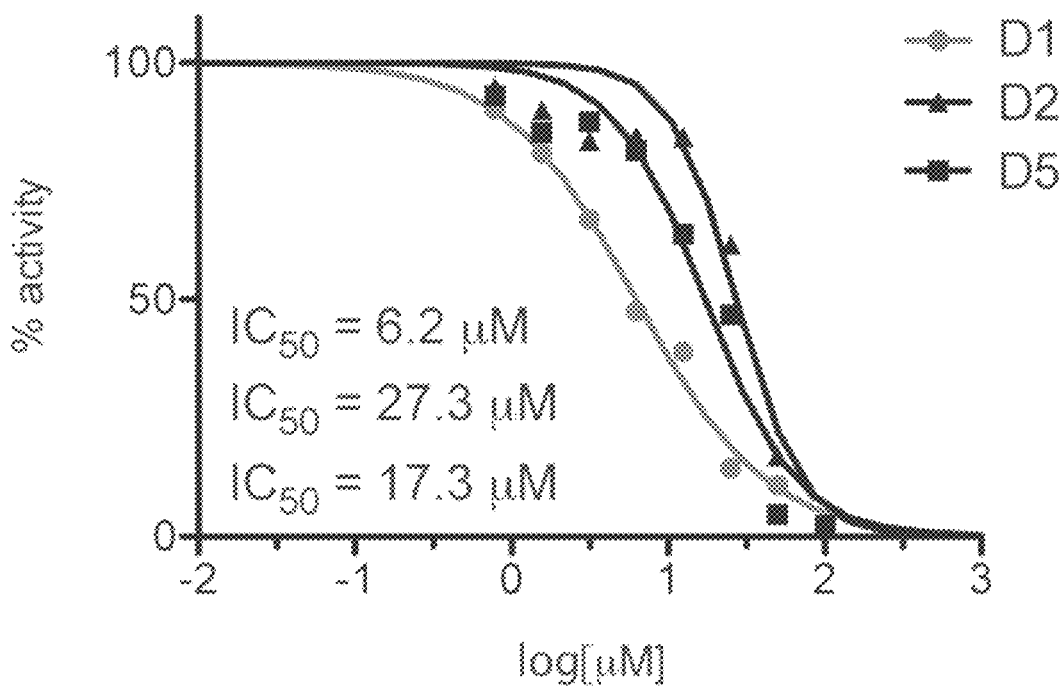

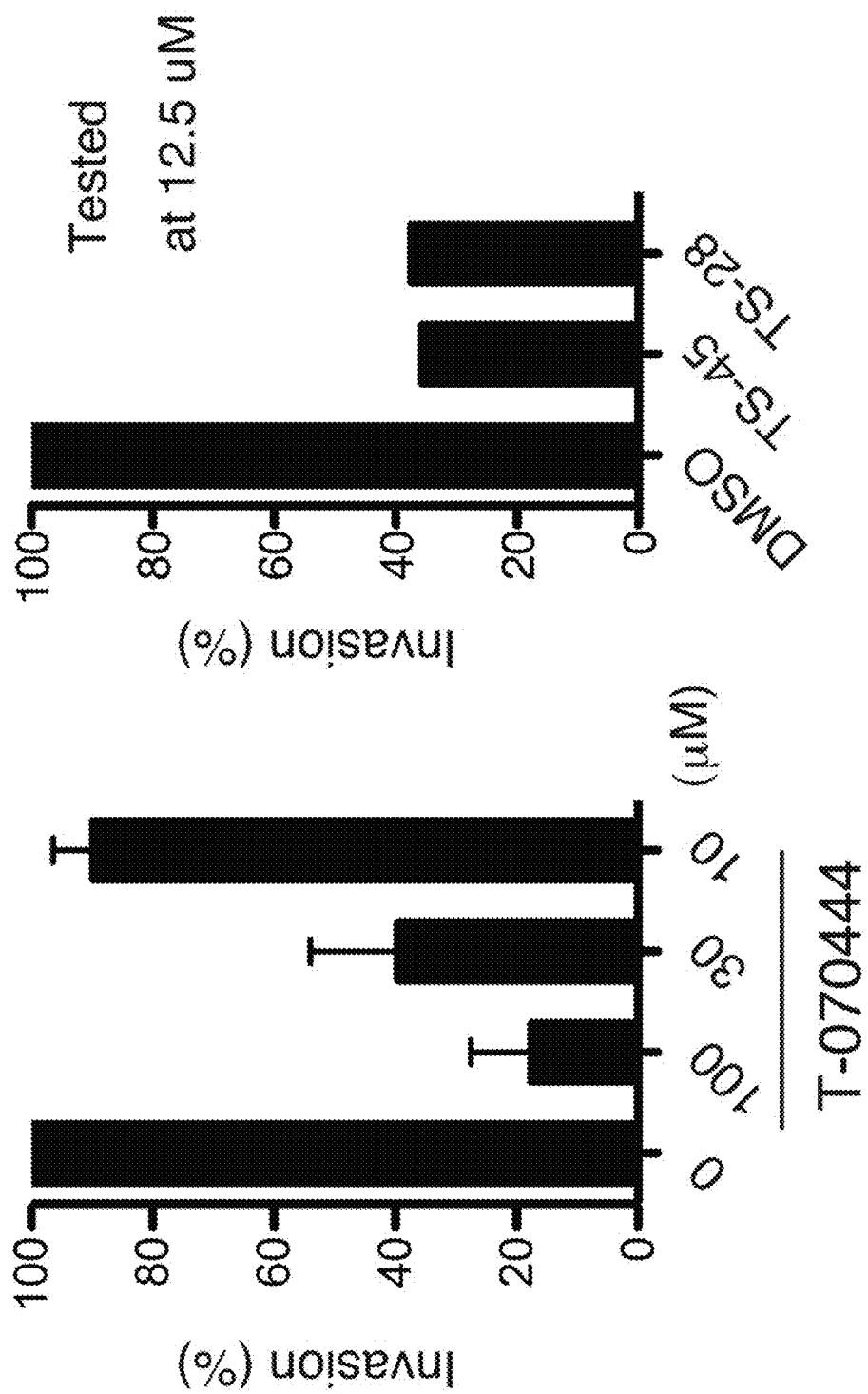

(A)

(B)

(A)

(B)

PYRIDINONE COMPOUND AND USE THEREOF

TECHNICAL FIELD

The present invention relates to a pyridinone compound and its use.

BACKGROUND ART

Cancer is the leading cause of death among the Japanese, and anti-cancer agents are being constantly developed. In particular, anti-cancer agents that are capable of inhibiting cancer cell invasion, metastasis, and other symptoms are being developed.

Generally, many anti-cancer agents cause serious side effects, and to meet the market's needs, it is time to develop anti-cancer agents that cause few side effects. Although molecularly targeted drugs, such as antibody drugs, in particular, are drawing attention, their manufacturing costs are high, and the drug prices do not decrease, which imposes a great burden on patients in terms of costs.

Patent Literature (PTL) 1 discloses a pyrazolidinedione derivative as a DOCK inhibitor. This compound is known to have an inhibitory effect on the Rac-GDP-to-Rac-GTP conversion activity (in this specification, this activity is sometimes referred to as "GEF activity") of DOCK1 (or DOCK180), DOCK2, and DOCK5, which are members of the DOCK-A subfamily.

In view of DOCK2 being expressed specifically in immune cells, PTL 1 confirms that pyrazolidinedione derivatives (e.g., CPYPP) inhibit chemokine-induced migration of immune cells (T cells, B cells), and discloses that such derivatives can be used as an active ingredient for treating immune diseases. The document also confirms that pyrazolidinedione derivatives have an inhibitory effect on cancer cell invasion and cancer cell anchorage-independent growth, and discloses that such derivatives can be used as an anti-cancer agent.

DOCK1 and DOCK5 have already been known to ubiquitously express in the whole body. Regarding DOCK1, in particular, a mechanism has been reported recently in which Rac activated by the GEF activity of DOCK1 regulates HER2-mediated breast cancer metastasis (Non-Patent Literature (NPL) 1). This document also reports that the CPYPP mentioned above inhibits the Rac activation and cancer cell migration.

DOCKs are known to be involved in ruffle formation, which serves as an index of morphological changes in cell migration. Two types of ruffles, i.e., peripheral ruffles and dorsal ruffles, have been clarified to be present in ruffle formation. It has also been clarified that the former is regulated by both DOCK1 and DOCK5 while the latter is regulated by DOCK1 alone (NPL 2).

CITATION LIST

Patent Literature

PTL 1: WO 2012/157389

Non-Patent Literature

NPL 1: Proc Natl Acad Sci USA, 2013, Vol. 110, 7434-7439
NPL 2: J Biol Chem, 2012, Vol. 288, 8092-8109
NPL 3: Nature, 2013, Vol. 497, 633-638
NPL 4: Nature, 2001, Vol. 412, 826-831

SUMMARY OF INVENTION

Technical Problem

As described above, pyrazolidinedione derivatives, such as CPYPP, have been found to inhibit the GEF activity of DOCK1, and DOCK1 activation is involved in the mechanism of the progression of cancer metastasis etc. In view of these findings, it may be effective to advance the development of an active ingredient of anti-cancer agents using pyrazolidinedione derivatives.

However, considering that CPYPP also inhibits the GEF activity of other in vivo molecules, such as DOCK2 and DOCK5, which are members of the DOCK-A subfamily, and that DOCK2 is specifically expressed in immune cells, the use of CPYPP as an active ingredient of anti-cancer agents would be likely to cause side effects in the immune system.

Accordingly, an object of the present invention is to provide a compound capable of being used as an active ingredient of an anti-cancer agent. To provide an anti-cancer agent with few side effects, an object of the present invention is to provide a compound capable of selectively inhibiting the target, i.e., DOCK1.

Solution to Problem

The present inventors performed in silico screening based on three-dimensional structure prediction models of a DOCK2-Rac complex, and further performed screening using various biological activities as an index, such as cancer cell invasion, cancer cell anchorage-independent growth, and the GEF activity of DOCK1, thus finding that specific pyridinone compounds can be used as an active ingredient of an anti-cancer agent. The inventors also found that these pyridinone compounds selectively inhibit the GEF activity of DOCK1.

The present invention has been accomplished based on these findings. More specifically, the invention encompasses the following various embodiments.

Item 1. A compound represented by Formula (1) below, or a salt thereof:

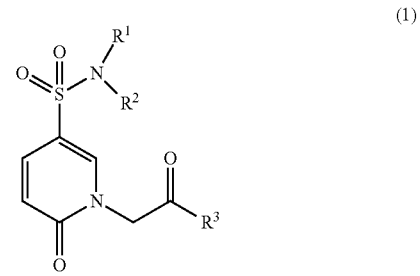

(1)

wherein $R^1$ and $R^2$ are the same or different, and each represents hydrogen, $C_{1-6}$ alkyl, or $C_{2-6}$ alkenyl, or $R^1$ and $R^2$, taken together with the nitrogen atom to which they are attached, may form a saturated 5- to 8-membered monocyclic ring, directly or via one or more heteroatoms; and $R^3$ is a group represented by any one of Formulas (2) to (6) below:

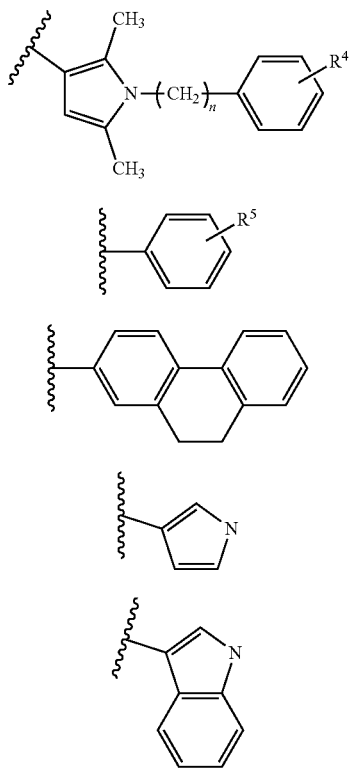

wherein n in a group represented by Formula (2) is 0 or 1, and $R^4$ in the group represented by Formula (2) is hydrogen, $C_{1-6}$ alkyl, halogen, $C_{1-6}$ alkoxy, or hydroxyl; and $R^5$ in a group represented by Formula (3) is hydrogen, phenyl, or naphthyl;

wherein the phenyl represented by $R^5$ is optionally substituted with at least one substituent selected from the group consisting of halogen, $C_{1-6}$ alkyl, trihalo $C_{1-6}$ alkyl, $C_{1-6}$ alkoxy, trihalo $C_{1-6}$ alkoxy, phenyl, biphenyl, aryl $C_{1-6}$ alkyl, naphthyl, nitro, and cyano, and wherein the pyrrole ring represented by Formula (5) and the indole ring represented by Formula (6) are optionally substituted with at least one $C_{1-6}$ alkyl.

Item 2. The pyridinone compound or a salt thereof according to Item 1, wherein $R^1$ and $R^2$ in Formula (1), taken together with the nitrogen atom to which they are attached, form a pyrrolidine ring, a pyrazolidine ring, an imidazolidine ring, an (iso)thiazolidine ring, an (iso) oxazolidine ring, a piperidine ring, a piperazine ring, a morpholine ring, a thiomorpholine ring, an azepane ring, a thioazepane ring, or an oxazepane ring.

Item 3. The pyridinone compound or a salt thereof according to Item 1 or 2, wherein $R^1$ and $R^2$ in Formula (1), taken together with the nitrogen atom to which they are attached, form a saturated 5-membered monocyclic ring via one or more heteroatoms.

Item 4. The pyridinone compound or a salt thereof according to any one of Items 1 to 3, wherein $R^1$ and $R^2$ in Formula (1), taken together with the nitrogen atom to which they are attached, form a pyrrolidine ring.

Item 5. The pyridinone compound or a salt thereof according to any one of Items 1 to 4, wherein $R^3$ in Formula (1) is a group represented by Formula (2).

Item 6. The pyridinone compound or a salt thereof according to any one of Items 1 to 5, wherein n in the group represented by Formula (2) is 1.

Item 7. The pyridinone compound or a salt thereof according to any one of Items 1 to 6, wherein $R^4$ in the group represented by Formula (2) is located at the para-position with respect to $—(CH_2)_n—$ bonding to the benzene ring.

Item 8. The pyridinone compound or a salt thereof according to any one of Items 1 to 7, wherein $R^4$ in the group represented by Formula (2) is halogen atoms.

Item 9. The pyridinone compound or a salt thereof according to any one of Items 1 to 4, wherein $R^3$ in Formula (1) is a group represented by Formula (3).

Item 10. The pyridinone compound or a salt thereof according to any one of Items 1 to 4, and 9, wherein $R^5$ in the group represented by Formula (3) is phenyl.

Item 11. The pyridinone compound or a salt thereof according to any one of Items 1 to 4, 9, and 10, wherein the phenyl represented by $R^5$ is substituted with at least one of halogen atoms or trihalo $C_{1-6}$ alkyl groups.

Item 12. The pyridinone compound or a salt thereof according to any one of Items 1 to 4 and 9 to 11, wherein the substituent or substituents on the phenyl represented by $R^5$ are located at the meta- and/or para-positions with respect to the carbonyl group bonding to the benzene ring.

Item 13. The pyridinone compound or a salt thereof according to any one of Items 1 to 4 and 9 to 12, wherein the pyridinone compound represented by Formula (1) is 1-(2-(1-(4-fluorobenzyl)-2,5-dimethyl-1H-pyrrol-3-yl)-2-oxoethyl)-5-(pyrrolidin-1-ylsulfonyl)pyridin-2(1H)-one, 1-(2-oxo-2-(4'-(trifluoromethyl)-[1,1'-biphenyl]-4-yl)ethyl)-5-(pyrrolidin-1-ylsulfonyl)pyridin-2(1H)-one, 1-(2-(4-(naphthalen-2-yl)phenyl)-2-oxoethyl)-5-(pyrrolidin-1-ylsulfonyl)pyridin-2(1H)-one, 1-(2-oxo-2-(3'-(trifluoromethyl)-[1,1'-biphenyl]-4-yl)ethyl)-5-(pyrrolidin-1-ylsulfonyl)pyridin-2(1H)-one, or 1-(2-(3'-chloro-[1,1'-biphenyl]-4-yl)-2-oxoethyl)-5-(pyrrolidin-1-ylsulfonyl)pyridin-2(1H)-one.

Item 14. A method for producing the pyridinone compound or a salt thereof of any one of items 1 to 13, the method comprising reacting a compound represented by Formula (7) below:

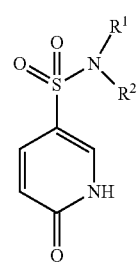

wherein $R^1$ and $R^2$ are each as defined in Item 1, with a compound represented by Formula (8) below:

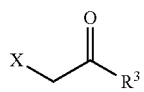

wherein X is halogen, and $R^3$ is as defined in Item 1, in the presence of a reducing agent.

Item 15. A DOCK1-selective inhibitor comprising the pyridinone compound or a salt thereof of any one of Items 1 to 13.

Item 16. The inhibitor according to Item 15, which selectively inhibits the GEF activity of DOCK1.

Item 17. A pharmaceutical composition comprising the DOCK1-selective inhibitor of Item 15 or 16 and a pharmaceutically acceptable salt.

Item 18. The pharmaceutical composition according to Item 16, for use in the treatment and/or prevention of cancer.

Item 19. The pharmaceutical composition according to Item 17, wherein the cancer is a metastatic cancer.

Item 20. A pharmaceutical composition comprising the pyridinone compound of any one of Items 1 to 13 or a pharmaceutically acceptable salt thereof.

Item 21. The pharmaceutical composition according to Item 19, for use in the treatment and/or prevention of cancer.

Item 22. The pharmaceutical composition according to Item 17, wherein the cancer is a metastatic cancer.

Item 23. A method for treating and/or preventing a disease, the method comprising the step of administering to a patient the pyridinone compound of any one of Items 1 to 13 or a pharmaceutically acceptable salt thereof.

Item 24. The method of treatment and/or prevention according to Item 22, wherein the patient is suffering from cancer, and the disease is cancer.

Item 25. The method of treatment and/or prevention according to Item 23, wherein the cancer is a metastatic cancer.

Item 26. Use of the pyridinone compound of any one of Items 1 to 13 or a pharmaceutically acceptable salt thereof in the manufacture of a pharmaceutical composition for the treatment and/or prevention of a disease.

Item 27. The use according to Item 25, wherein the disease is cancer.

Item 28. The use according to Item 26, wherein the cancer is a metastatic cancer.

Item 29. A method for screening a DOCK1-selective inhibitor from test substances, the method comprising the following steps 1 and 2:

step 1 of adding test substances to cells; and step 2 of selecting a substance that selectively inhibits a function of DOCK1 in the cells from the test substances added in step 1.

Item 30. The method according to Item 29, wherein the selective inhibition of the function of DOCK1 in step 2 is to selectively inhibit the GEF activity of DOCK1 in the cells to which the test substances have been added.

Item 31. The method according to Item 29 or 30, wherein the cells to which the test substances are added in step 1 are invasive cells, and the selective inhibition of the function of DOCK1 in step 2 is to inhibit the invasiveness of the cells after the addition of the test substances to the cells.

Item 32. The method according to any one of Items 29 to 31, wherein the cells to which the test substances are added in step 1 are non-immune system cells, and the selective inhibition of the function of DOCK1 in step 2 is to inhibit dorsal ruffle formation without affecting the peripheral ruffle formation in the cells after the addition of the test substances to the cells.

Item 33. The method according to any one of Items 29 to 31, wherein the cells to which the test substances are added in step 1 are immune cells, and the selective inhibition of the function of DOCK1 in step 2 does not affect the migration response of cells through inhibition of proteins belonging to the DOCK families, other than DOCK1, after the addition of the test substances to the cells.

The present invention also encompasses the invention according to the following embodiments.

Item A-1. A pharmaceutical composition comprising a DOCK1-selective inhibitor as an active ingredient.

Item A-2. The pharmaceutical composition according to item A-1, wherein the DOCK1-selective inhibitor selectively inhibits the GEF activity of DOCK1.

Item A-3. The pharmaceutical composition according to Item A-2, for use in the treatment and/or prevention of cancer.

Item A-4. The pharmaceutical composition according to Item A-3, wherein the cancer is a metastatic cancer.

Item A-5. The pharmaceutical composition according to any one of Items A-1 to A-4, wherein the DOCK1-selective inhibitor is a pyridinone compound represented by Formula (1) below, or a salt thereof:

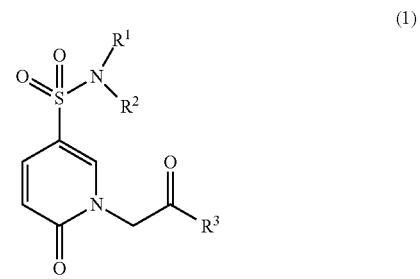

(1)

wherein $R^1$ and $R^2$ are the same or different, and each represents hydrogen, $C_{1-6}$ alkyl, or $C_{2-6}$ alkenyl, or $R^1$ and $R^2$, taken together with the nitrogen atom to which they are attached, may form a saturated 5- to 8-membered monocyclic ring, directly or via one or more heteroatoms; and $R^3$ is a group represented by any one of Formulas (2) to (6) below:

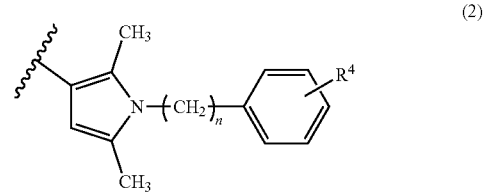

(2)

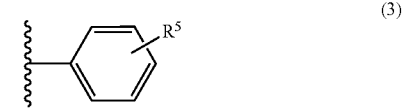

(3)

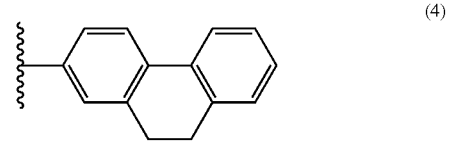

(4)

(5)

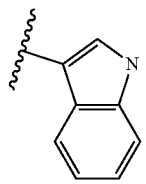
(6)

wherein n in a group represented by Formula (2) is 0 or 1, and $R^4$ in the group represented by Formula (2) is hydrogen, $C_{1-6}$ alkyl, halogen, $C_{1-6}$ alkoxy, or hydroxyl; and $R^5$ in a group represented by Formula (3) is hydrogen, phenyl, or naphthyl;

wherein the phenyl represented by $R^5$ is optionally substituted with at least one substituent selected from the group consisting of halogen, $C_{1-6}$ alkyl, trihalo $C_{1-6}$ alkyl, $C_{1-6}$ alkoxy, trihalo $C_{1-6}$ alkoxy, phenyl, biphenyl, aryl $C_{1-6}$ alkyl, naphthyl, nitro, and cyano, and wherein the pyrrole ring represented by Formula (5) and the indole ring represented by Formula (6) are optionally substituted with at least one $C_{1-6}$ alkyl.

Item A-6. The pharmaceutical composition according to any one of Items A-1 to A-5, wherein $R^1$ and $R^2$ in Formula (1), taken together with the nitrogen atom to which they are attached, form a pyrrolidine ring, a pyrazolidine ring, an imidazolidine ring, an (iso)thiazolidine ring, an (iso)oxazolidine ring, a piperidine ring, a piperazine ring, a morpholine ring, a thiomorpholine ring, an azepane ring, a thioazepane ring, or an oxazepane ring.

Item A-7. The pharmaceutical composition according to any one of Items A-1 to A-6, wherein $R^1$ and $R^2$ in Formula (1), taken together with the nitrogen atom to which they are attached, form a saturated 5-membered monocyclic ring via one or more heteroatoms.

Item A-8. The pharmaceutical composition according to any one of Items A-1 to A-7, wherein $R^1$ and $R^2$ in Formula (1), taken together with the nitrogen atom to which they are attached, form a pyrrolidine ring.

Item A-9. The pharmaceutical composition according to any one of Items A-1 to A-8, wherein $R^3$ in Formula (1) is a group represented by Formula (2).

Item A-10. The pharmaceutical composition according to any one of Items A-1 to A-9, wherein n in the group represented by Formula (2) is 1.

Item A-11. The pharmaceutical composition according to any one of Items A-1 to A-10, wherein $R^4$ in the group represented by Formula (2) is located at the para-position with respect to —$(CH_2)_n$— bonding to the benzene ring.

Item A-12. The pharmaceutical composition according to any one of Items A-1 to A-11, wherein $R^4$ in the group represented by Formula (2) is halogen.

Item A-13. The pharmaceutical composition according to any one of Items A-1 to A-12, wherein $R^3$ in Formula (1) is a group represented by Formula (3).

Item A-14. The pharmaceutical composition according to any one of Items A-1 to A-13, wherein $R^5$ in the group represented by Formula (3) is phenyl.

Item A-15. The pharmaceutical composition according to any one of Items A-1 to A-8, A-13, and A-14, wherein the phenyl represented by $R^5$ is substituted with at least one of halogen atoms or trihalo $C_{1-6}$ alkyl groups.

Item A-16. The pharmaceutical composition according to any one of Items A-1 to A-8 and A-13 to A-15, wherein the substituent or substituents on the phenyl represented by $R^5$ are located at the meta- and/or para-positions with respect to the carbonyl group bonding to the benzene ring.

Item A-17. The pharmaceutical composition according to any one of Items A-1 to A-8 and A-13 to A-16, wherein the pyridinone compound represented by Formula (1) is 1-(2-(1-(4-fluorobenzyl)-2,5-dimethyl-1H-pyrrol-3-yl)-2-oxoethyl)-5-(pyrrolidin-1-ylsulfonyl) pyridin-2(1H)-one, 1-(2-oxo-2-(4'-(trifluoromethyl)-[1,1'-biphenyl]-4-yl)ethyl)-5-(pyrrolidin-1-ylsulfonyl)pyridin-2(1H)-one, 1-(2-(4-(naphthalen-2-yl)phenyl)-2-oxoethyl)-5-(pyrrolidin-1-ylsulfonyl)pyridin-2(1H)-one, 1-(2-oxo-2-(3'-(trifluoromethyl)-[1,1'-biphenyl]-4-yl)ethyl)-5-(pyrrolidin-1-ylsulfonyl)pyridin-2(1H)-one, or 1-(2-(3'-chloro-[1,1'-biphenyl]-4-yl)-2-oxoethyl)-5-(pyrrolidin-1-ylsulfonyl) pyridin-2(1H)-one.

Item A-18. A method for screening a DOCK1-selective inhibitor from test substances, the method comprising the following steps 1 and 2:
step 1 of adding test substances to cells; and
step 2 of selecting a substance that selectively inhibits a function of DOCK1 in the cells from the test substances added in step 1.

Item A-19. The method according to Item A-18, wherein the selective inhibition of the function of DOCK1 in step 2 is to selectively inhibit the GEF activity of DOCK1 in the cells to which the test substances have been added.

Item A-20. The method according to Item A-18 or A-19, wherein the cells to which the test substances are added in step 1 are invasive cells, and the selective inhibition of the function of DOCK1 in step 2 is to inhibit the invasiveness of the cells after the addition of the test substances to the cells.

Item A-21. The method according to any one of Items A-18 to A-20, wherein the cells to which the test substances are added in step 1 are non-immune system cells, and the selective inhibition of the function of DOCK1 in step 2 is to inhibit dorsal ruffle formation without affecting the peripheral ruffle formation in the cells after the addition of the test substances to the cells.

Item A-22. The method according to any one of Items A-18 to A-20, wherein the cells to which the test substances are added in step 1 are immune cells, and the selective inhibition of the function of DOCK1 in step 2 does not affect the migration response of cells through inhibition of proteins belonging to the DOCK families, other than DOCK1, after the addition of the test substances to the cells.

The present invention further encompasses the invention according to the following embodiments.

Item B. A method for treating and/or preventing a disease, the method comprising the step of administering to a patient a DOCK1-selective inhibitor.

Item C. Use of a DOCK1-selective inhibitor in the manufacture of a pharmaceutical composition for the treatment and/or prevention of a disease.

As the DOCK1-selective inhibitor recited in Items B and C, those recited in Items A-2 to A-17 are applicable.

Advantageous Effects of Invention

The pyridinone compound of the present invention has an inhibitory activity with selectivity to DOCK1.

The pyridinone compound of the present invention is useful as an active ingredient of an anti-cancer agent.

(A) shows the results, from the left, of DMSO, T-070444, NT-01, NT-02, NT-03, NT-04, NT-05, NT-06, NT-07, NT-08, NT-09, NT-10, NT-11, NT-12, NT-13, TS-03, TS-07, TS-08, TS-09, and TS-10.

(B) shows the results, from the left, of DMSO, T-070444, NT-07, NT-09, NT-12, TS-09, TS-11, TS-12, TS-13, TS-14, TS-15, TS-16, TS-17, TS-18, TS-20, TS-21, TS-22, TS-24, TS-25, and TS-26.

(C) shows the results, from the left, of DMSO, T-070444, TS-27, TS-28, TS-29, TS-30, TS-35, TS-36, TS-37, TS-38, TS-39, TS-40, TS-41, TS-42, TS-43, TS-44, TS-45, TS-46, TS-47, and TS-48.

(D) shows the results, from the left, of DMSO, T-070444, TS-49, TS-50, TS-51, TS-52, TS-53, TS-54, TS-56, TS-57, TS-58, TS-59, TS-60, TS-61, TS-62, TS-63, TS-64, TS-65, TS-66, TS-67, and TS-68. The vertical axis represents percent inhibition (%) of cellular invasion. The percent inhibition is obtained by converting the number of invading cells at the time of the addition of each compound to percentage, taking the number of invading cells in a control group (DMSO at the same concentration was added alone) as 100%, and deducting the resulting value from 100%.

Figure 9:
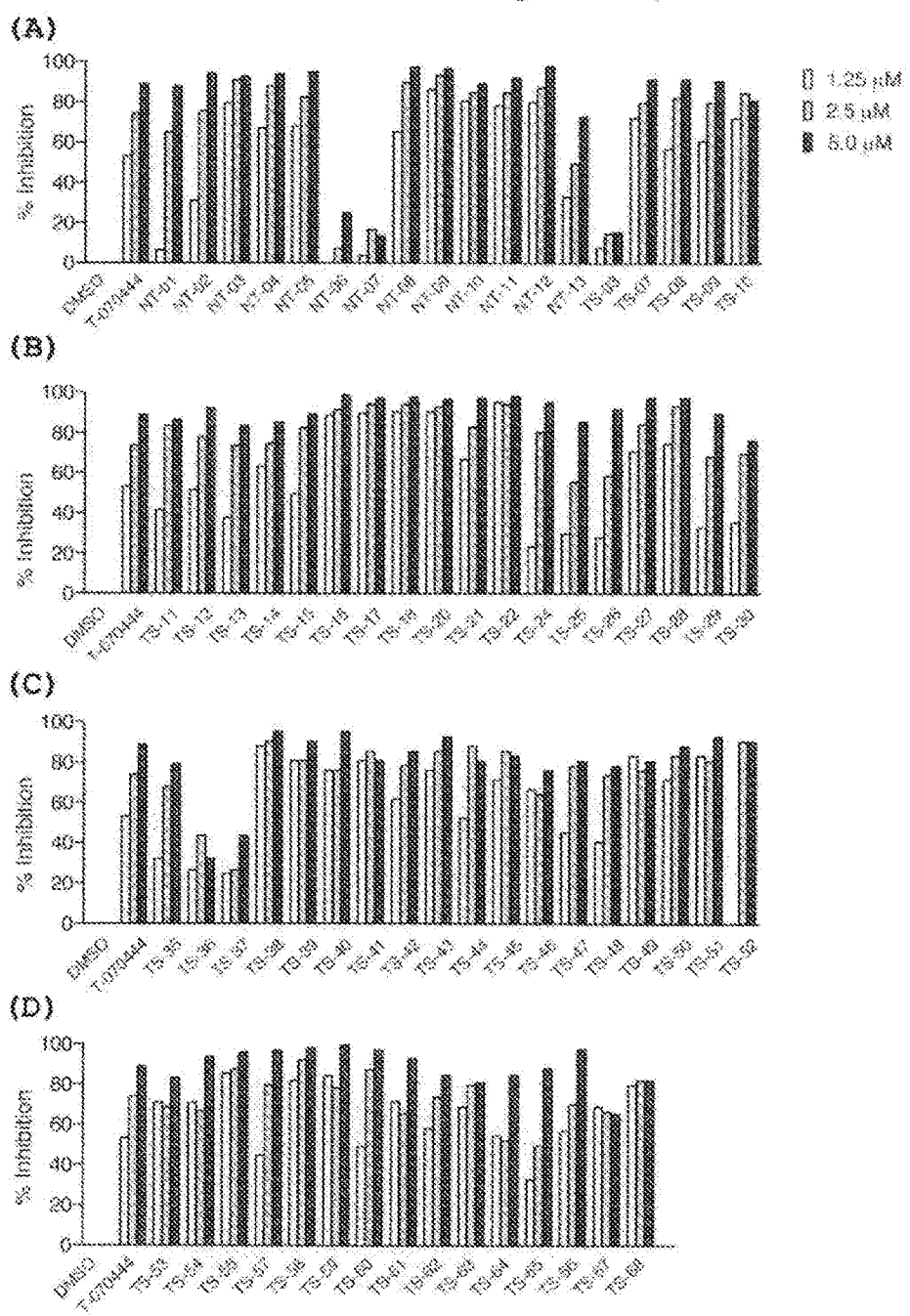

FIG. 9 is graphs showing the screening results obtained using as an index the inhibitory effect of the pyridinone compounds of the present invention on the anchorage independent growth of cancer cell (3LL).

(A) shows the results, from the left, of DMSO, T-070444, NT-01, NT-02, NT-03, NT-04, NT-05, NT-06, NT-07, NT-08, NT-09, NT-10, NT-11, NT-12, NT-13, TS-03, TS-07, TS-08, TS-09, and TS-10.

(B) shows the results, from the left, of DMSO, T-070444, TS-11, TS-12, TS-13, TS-14, TS-15, TB-16, TS-17, TS-18, TS-20, TS-21, TS-22, TS-24, TS-25, TS-26, TS-27, TS-28, TS-29, and TS-30.

(C) shows the results, from the left, of DMSO, T-070444, TS-35, TS-36, TS-37, TS-38, TS-39, TS-40, TS-41, TS-42, TS-43, TS-44, TS-45, TS-46, TS-47, TS-48, TS-49, TS-50, TS-51, and TS-52.

(D) shows the results, from the left, of DMSO, T-070444, TS-53, TS-54, TS-56, TS-57, TS-58, TS-59, TS-60, TS-61, TS-62, TS-63, TS-64, TS-65, TS-66, TS-67, and TS-68. The vertical axis represents the percent inhibition (%) of anchorage independent growth. The percent inhibition is obtained by converting the number of colonies formed at the time of addition of predetermined concentration of each compound to percentage, taking the number of colonies formed in soft agar of a control group (DMSO at the same concentration was added alone) as 100%, and deducting the resulting value from 100%.

Figure 10:
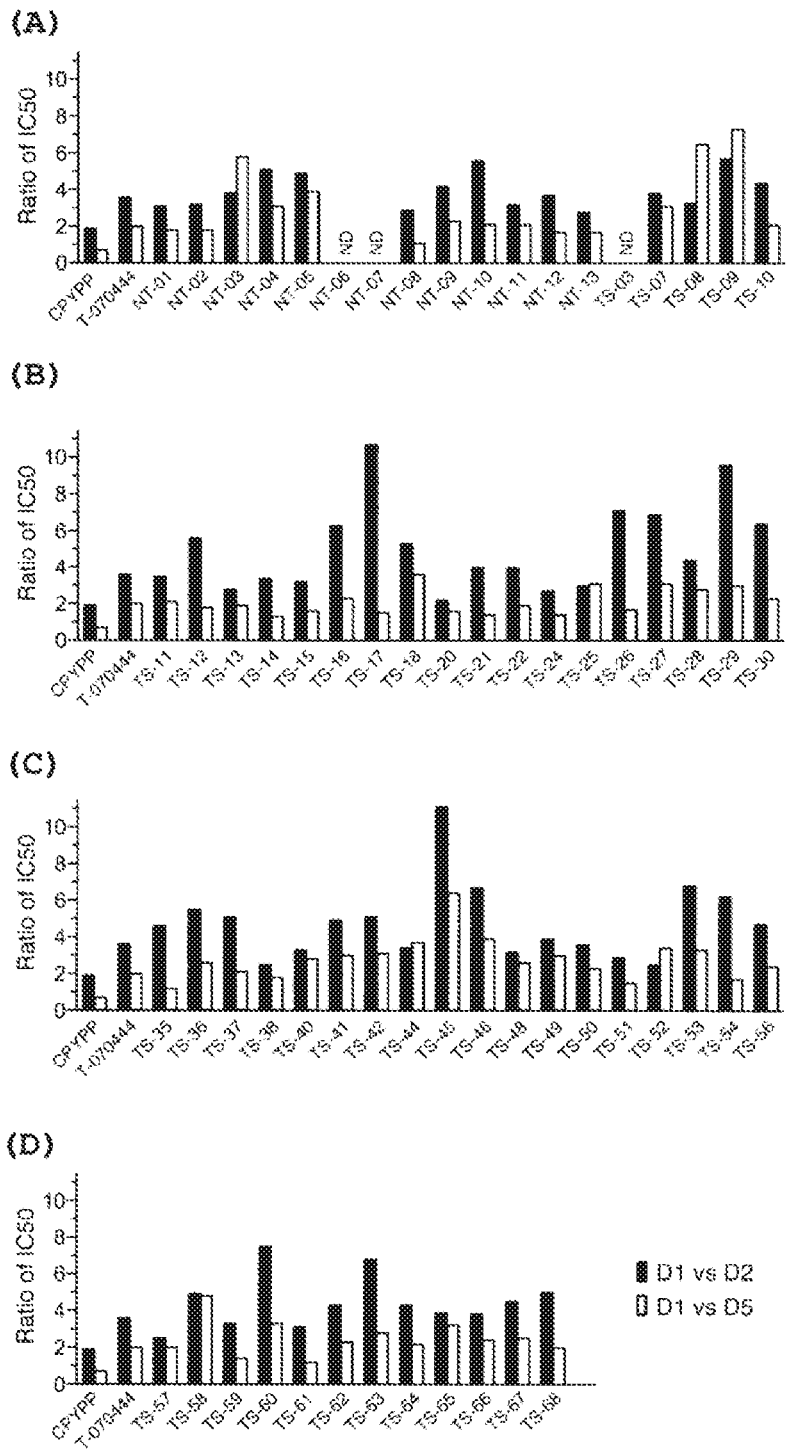

FIG. 10 is graphs showing the screening results obtained using as an index the effect of the pyridinone compound of the present invention on DOCK1 selective inhibition.

(A) shows the results, from the left, of CPYPP, T-070444, NT-01, NT-02, NT-03, NT-04, NT-05, NT-06, NT-07, NT-08, NT-09, NT-10, NT-11, NT-12, NT-13, TS-03, TS-07, TS-08, TS-09, and TS-10.

(B) shows the results, from the left, of CPYPP, T-070444, TS-11, TS-12, TS-13, TS-14, TS-15, TS-16, TS-17, TS-18, TS-20, TS-21, TS-22, TS-23, TS-24, TS-25, TS-26, TS-27, TS-28, TS-29, and TS-30.

(C) shows the results, from the left, of CPYPP, T-070444, TS-35, TS-36, TS-37, TS-38, TS-40, TS-41, TS-42, TS-44, TS-45, TS-46, TS-48, TS-49, TS-50, TS-51, TS-52, TS-53, TS-54, and TS-56.

(D) shows the results, from the left, of CPYPP, T-070444, TS-57, TS-58, TS-59, TS-60, TS-61, TS-62, TS-63, TS-64, TS-65, TS-66, TS-67, and TS-68. The vertical axis represents (■) DOCK1 selectivity of each compound relative to DOCK2, and (□) DOCK1 selectivity relative to DOCK5, calculated using the $IC_{50}$ values for DOCK1, DOCK2, and DOCK5 of each compound in the in vitro GEF assay. The DOCK1 selectivity relative to DOCK2 is a value obtained by dividing the $IC_{50}$ value for DOCK2 by the $IC_{50}$ value for DOCK1. The DOCK1 selectivity relative to DOCK5 is a value obtained by dividing the $IC_{50}$ value for DOCK5 by the $IC_{50}$ value for DOCK1.

Figure 11A:
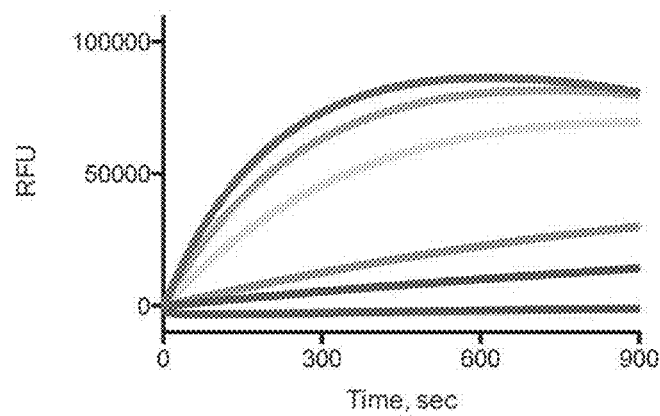
Figure 11A:
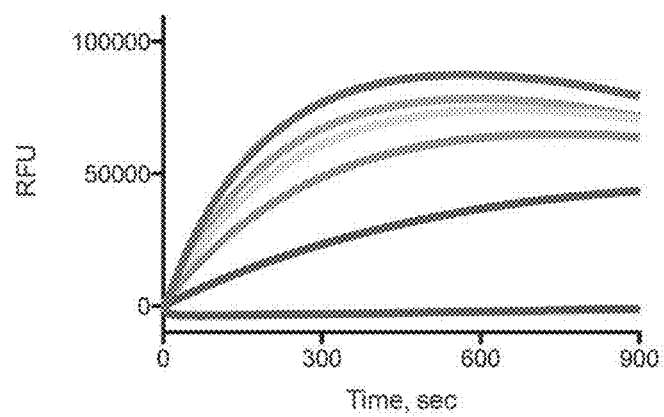
Figure 11A:
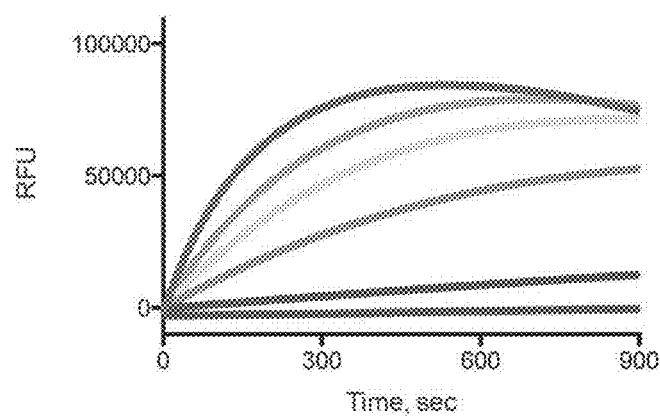
Figure 11C:
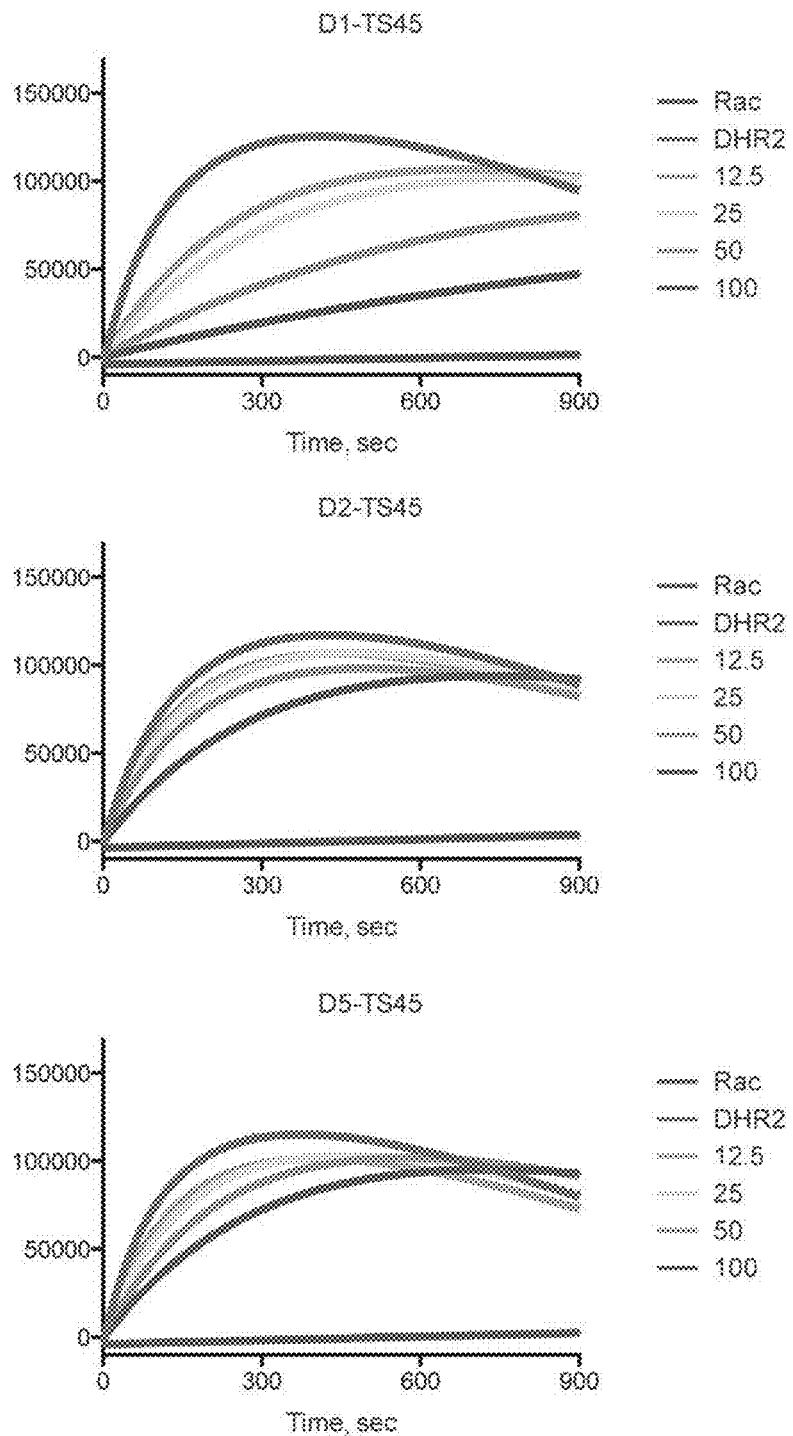
Figure 11D:
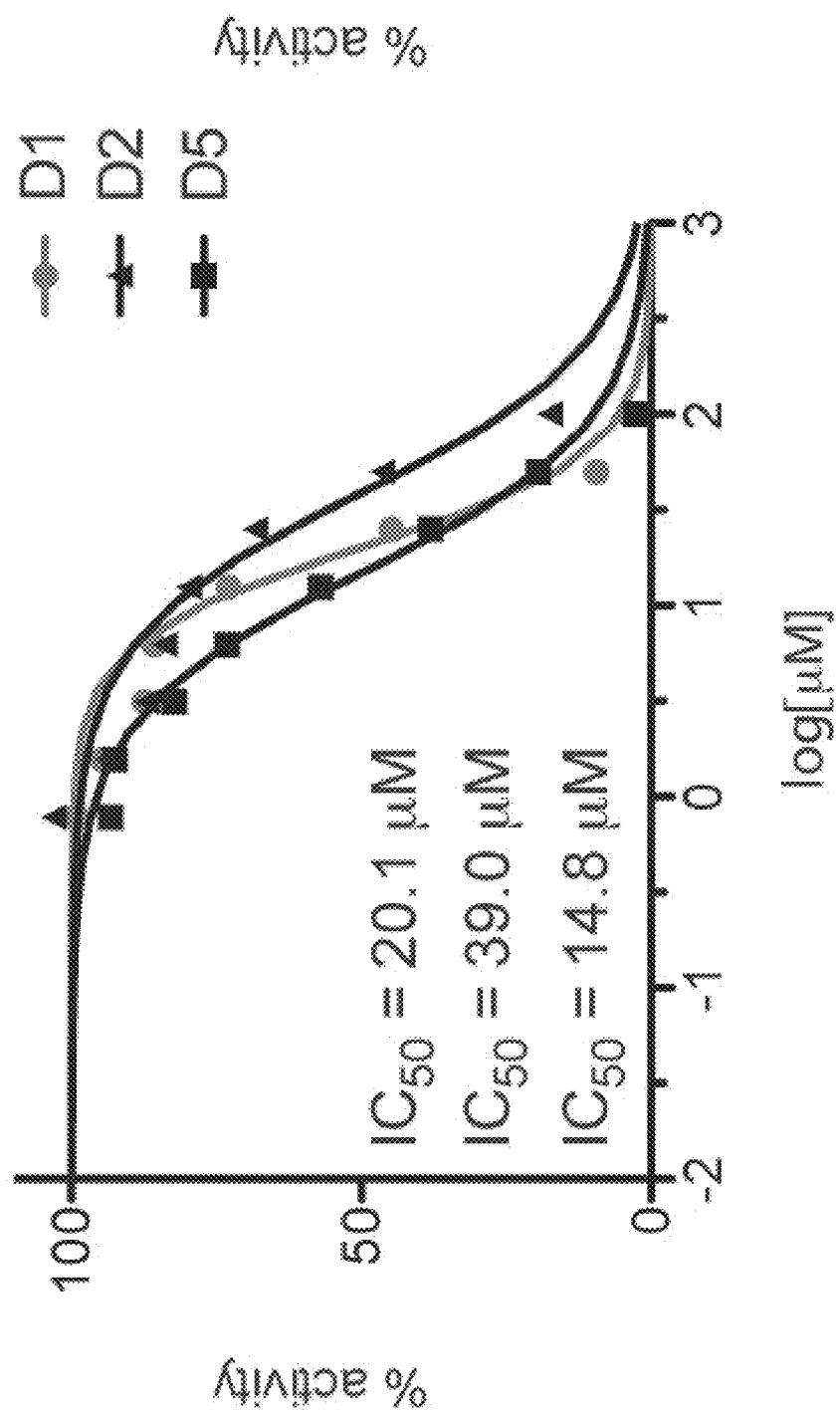
Figure 11E:
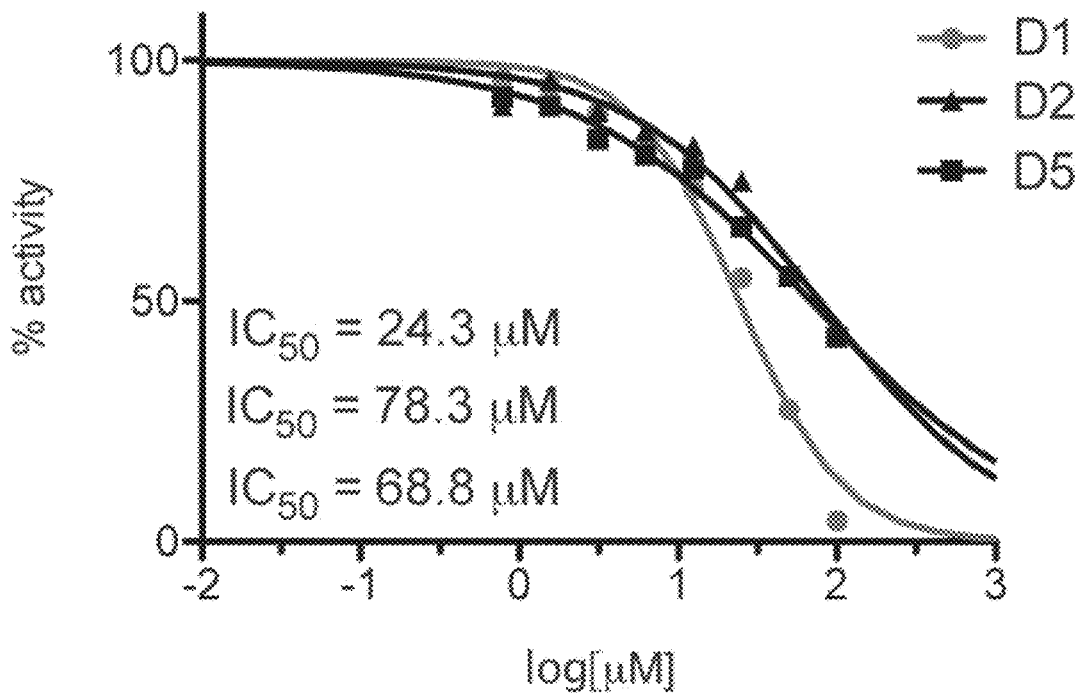
Figure 11E:
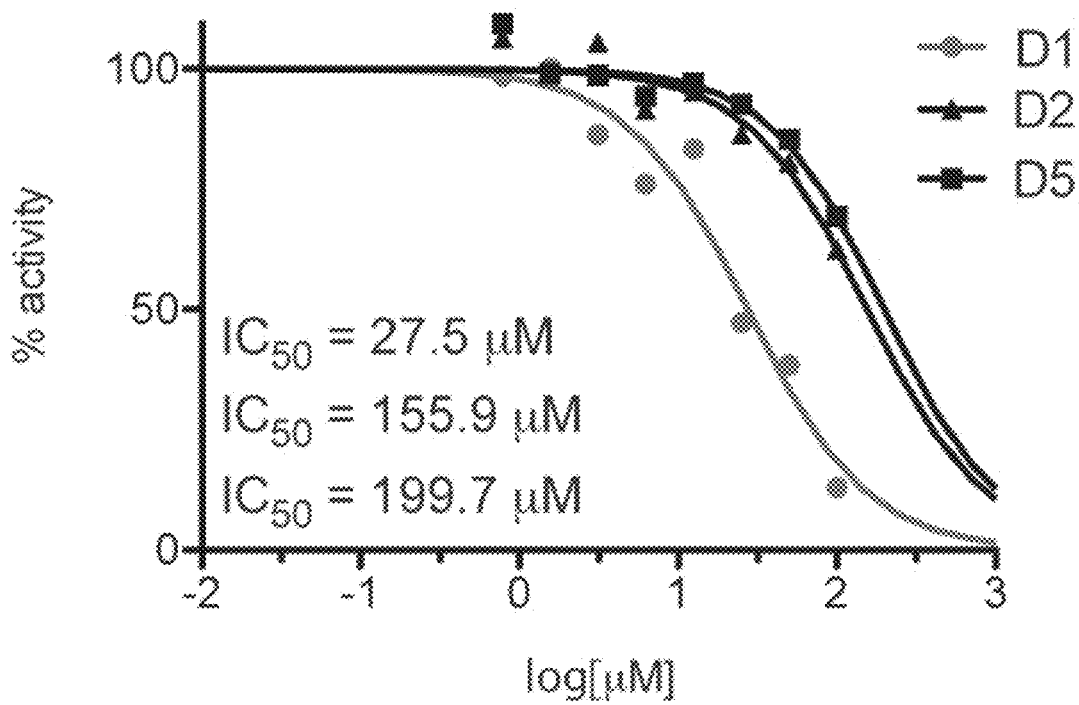

FIGS. 11(A)-(F) show graphs of the results confirming the effect of the pyridinone compounds of the present invention on DOCK1 selective inhibition. In the graphs shown in FIGS. 11(A)-(C), the vertical axis represents the fluorescence intensity obtained in the experiment while the horizontal axis represents the time from the initiation of the reaction. The fluorescence intensity reflects the amount of GTP-Rac produced. The reaction curves in each panel represent the following: a reaction solution containing Rac and the DHR-2 domain of DOCK1, DOCK2, or DOCK5, as well as containing DMSO of the same concentration (red); a reaction solution containing Rac and the DHR-2 domain of DOCK1, DOCK2, or DOCK5, as well as containing a predetermined concentration of each compound (12.5, 25, 50, and 100 µM from the top, which are orange, yellow, green, and blue, respectively); and Rac alone. The unit of the vertical axis is a relative fluorescence unit (RFU). The graphs in FIG. 11(D)-(F) show the GEF activity calculated based on the graphs in FIG. 11(A)-(C). The numerical values in the graphs are $IC_{50}$ values for DOCK1, DOCK2, and DOCK5 in order from the top. Specifically, referring to the graph for CPYPP, the $IC_{50}$ value for DOCK1 is 20.0 µM, the $IC_{50}$ value for DOCK2 is 39.0 µM, and the $IC_{50}$ value for DOCK5 is 14.8 µM. The same applies to the other graphs.

Figure 12A:
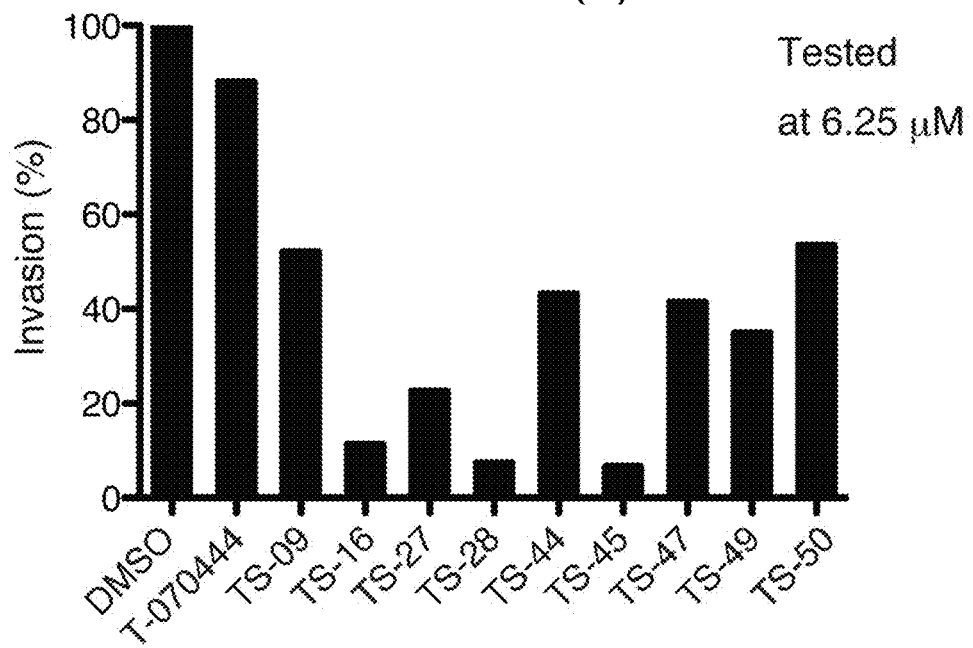
Figure 12B:
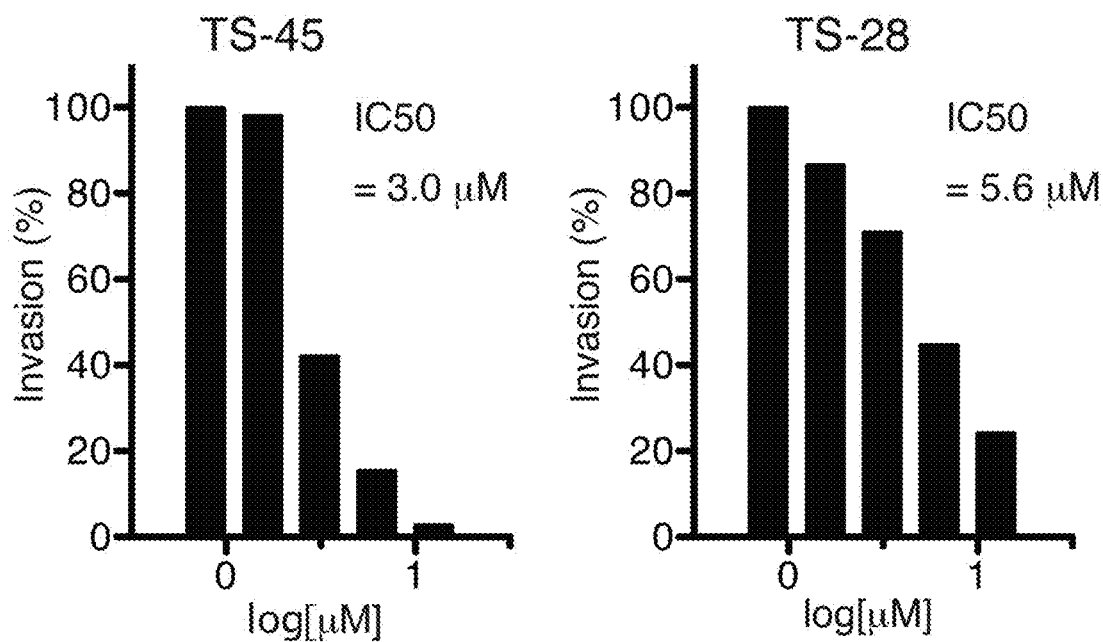
Figure 12D:
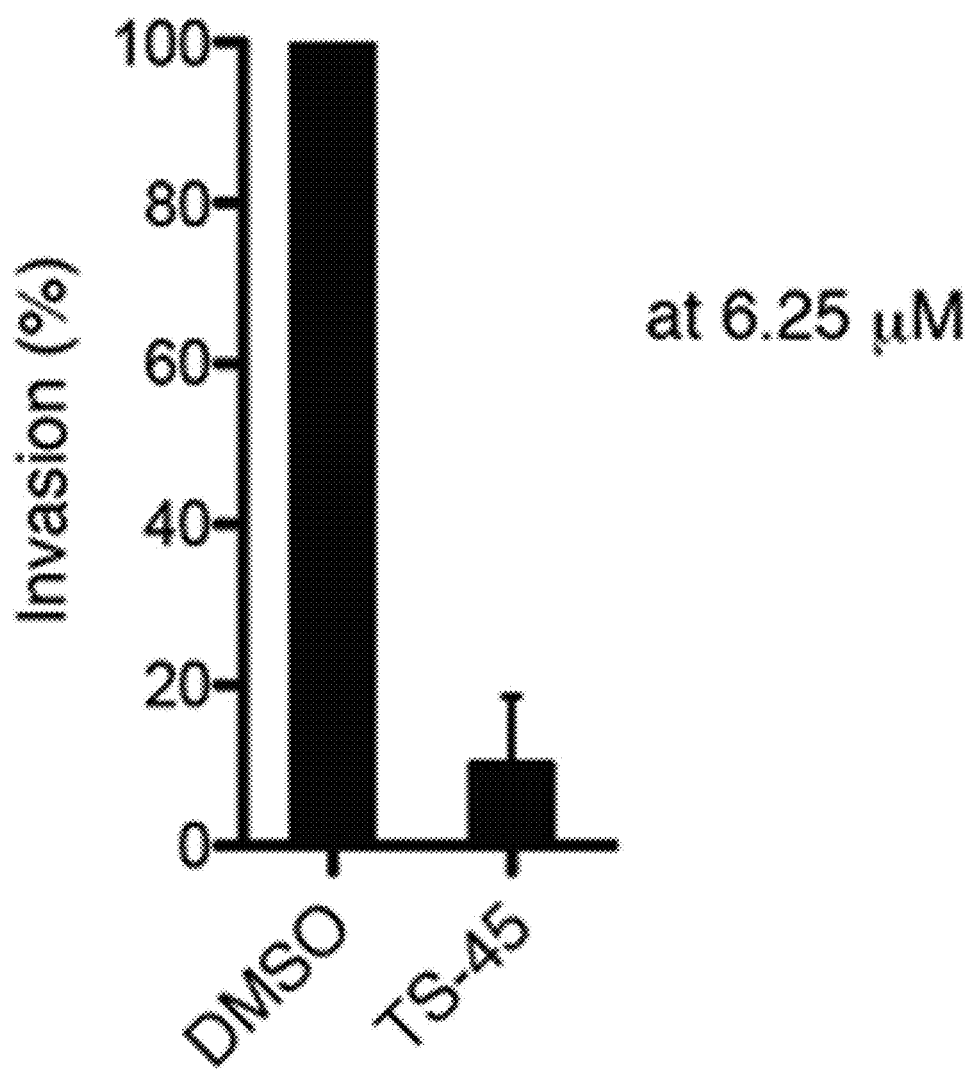

FIGS. 12(A)-(D) are graphs showing the experimental results confirming the inhibitory effect of the pyridinone compounds of the present invention on cancer cell invasion. The graphs shown in FIG. 12(A) or FIG. 12(B) show quantified invasive potential of mouse lung carcinoma cell line (3LL) in the presence of the pyridinone compounds of the present invention. The graphs shown in FIG. 12(C) show quantified invasive potential of human fibrosarcoma cell line (HT-1080) in the presence of the pyridinone compound of the present invention. The graph in FIG. 12(D) shows quantified invasive potential of human colon cancer cell line (DLD-1) in the presence of the pyridinone compound of the present invention. The vertical axis in FIGS. 12(C) and (D) represents percent cell invasion (%), taking the number of invading cells under control conditions (with addition of DMSO) as 100%.

Figure 13:
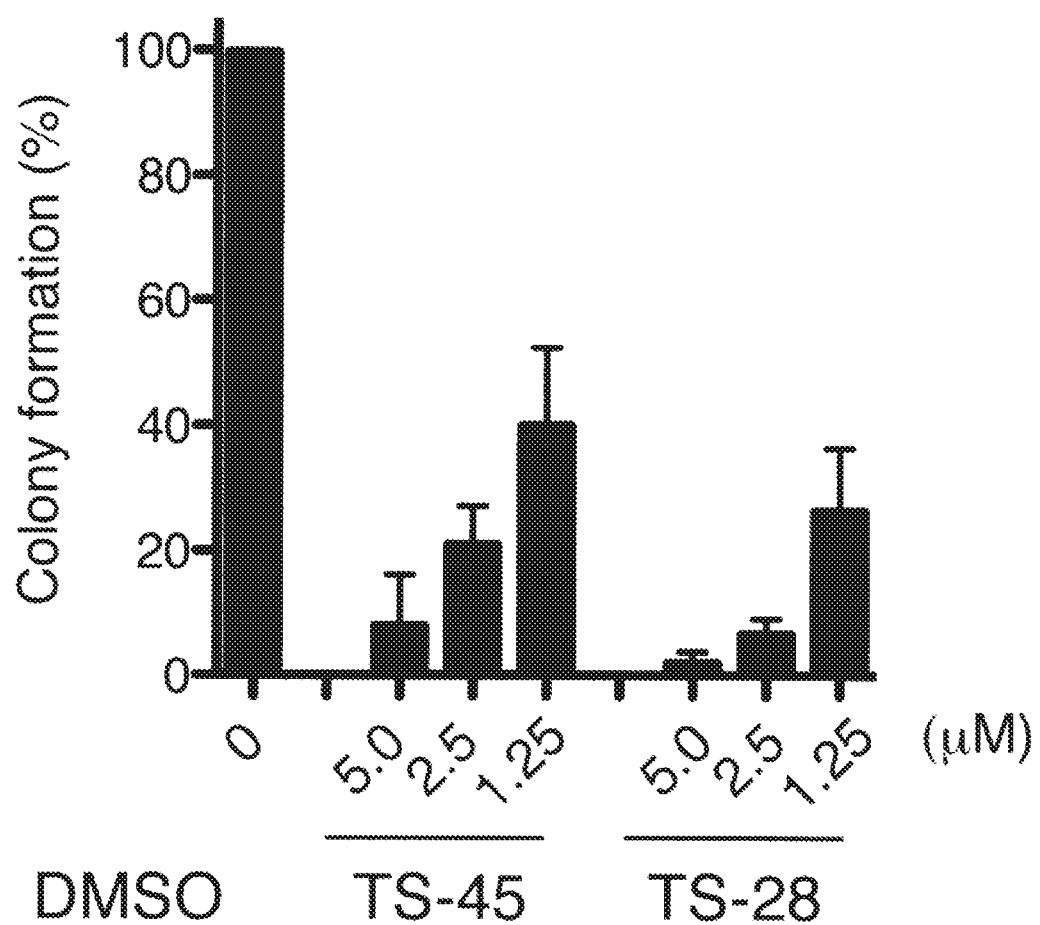

FIG. 13 is a graph showing the experimental results confirming the inhibitory effect of the pyridinone compounds of the present invention on cancer cell anchorage-independent growth. The graph shows quantified colony formation potential of mouse lung carcinoma cell line (3LL) in soft agar in the presence of the pyridinone compounds of the present invention.

Figure 14:
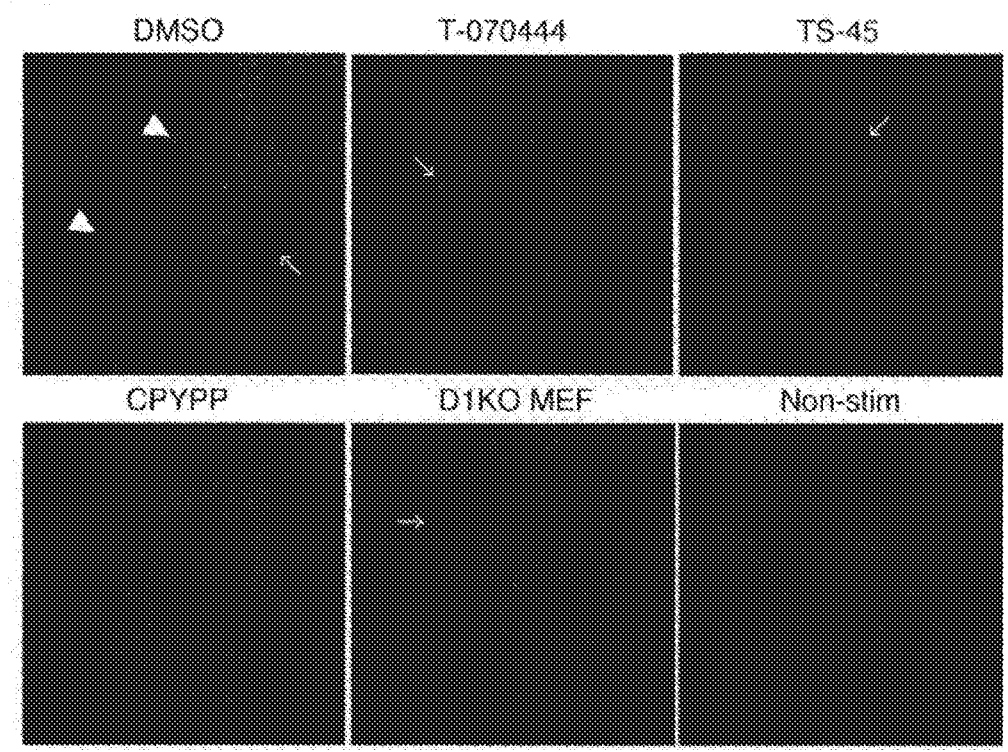
Figure 14:
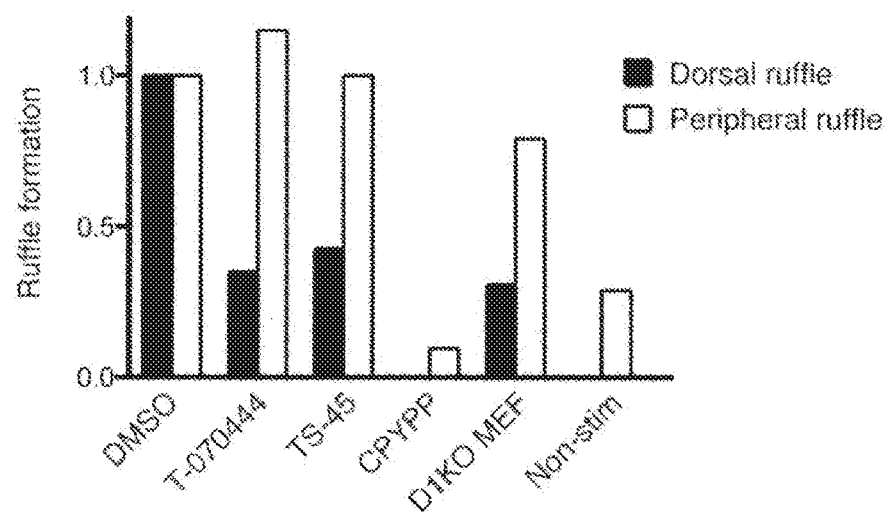

FIG. 14 shows the experimental results of inhibition on ruffle formation by the pyridinone compounds of the present invention. (A) is fluorescence microscope images based on analysis of morphological changes when primary mouse embryonic fibroblasts (MEFs) were pretreated with the compound and stimulated with PDGF. The arrows indicate peripheral ruffles while the arrowheads indicate dorsal ruffles. (B) is a graph showing quantified peripheral ruffle or dorsal ruffle formation potential in the presence of the pyridinone compounds of the present invention, based on the fluorescence microscope images in (A). The vertical axis represents the ratio of peripheral ruffle or dorsal ruffle formation under each condition, relative to the peripheral ruffle or dorsal ruffle formation under control conditions (with the addition of DMSO) taken as 1.

Figure 15:
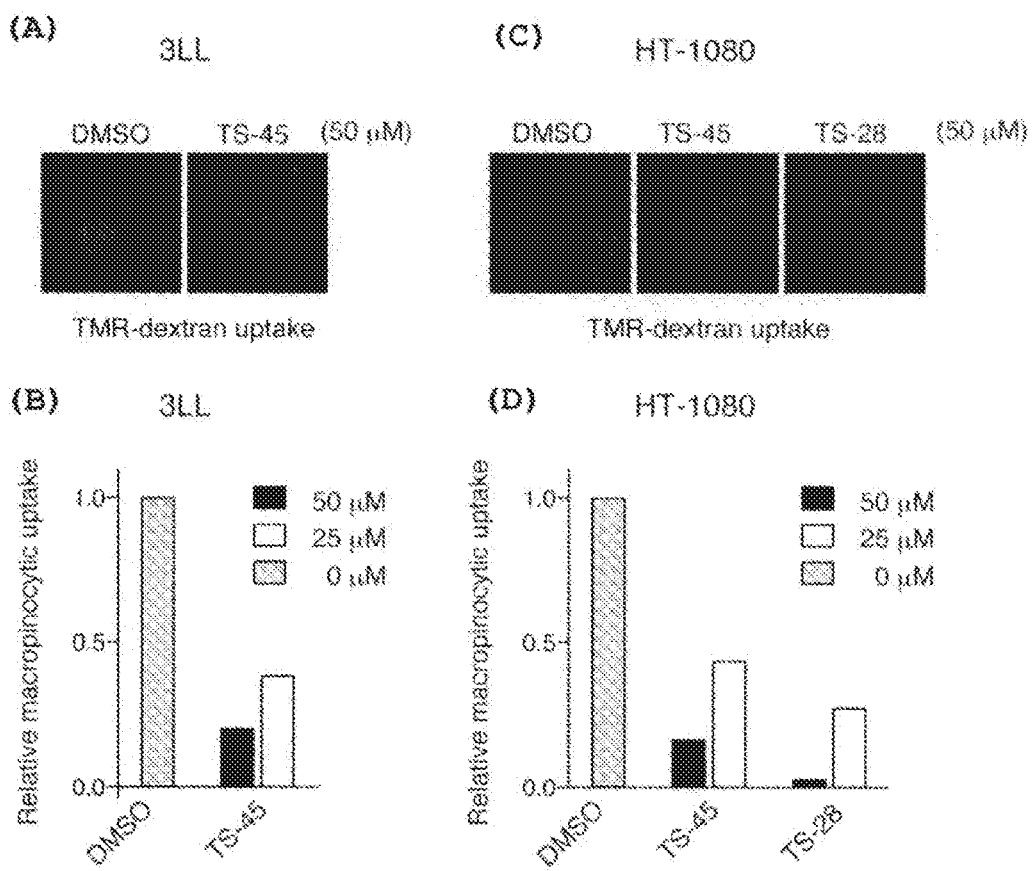

FIG. 15 shows the experimental results of macropinocytosis inhibition by the pyridinone compound of the present invention. (A) is fluorescence microscope images based on analysis on macropinocytosis activity of mouse lung carcinoma cell line (3LL), using uptake of TMR-dextran (dextran labeled with TMR, red) as an index. The cell nuclei were stained with DAPI (blue). (B) is a graph showing quantified macropinocytosis activity in the presence of the pyridinone compound of the present invention, based on the fluorescence microscope images in (A). (C) is fluorescence microscope images based on analysis on macropinocytosis activity of human fibrosarcoma cell line (HT-1080), using uptake of TMR-dextran (dextran labeled with TMR, red) as an index. The cell nuclei were stained with DAPI (blue). (D) is a graph showing quantified macropinocytosis activity in the presence of the pyridinone compounds of the present invention, based on the fluorescence microscope images in (C). The vertical axis represents the degree of dextran uptake under each condition, relative to the degree of dextran uptake by the cells under control conditions (with the addition of DMSO) taken as 1.

Figure 16:
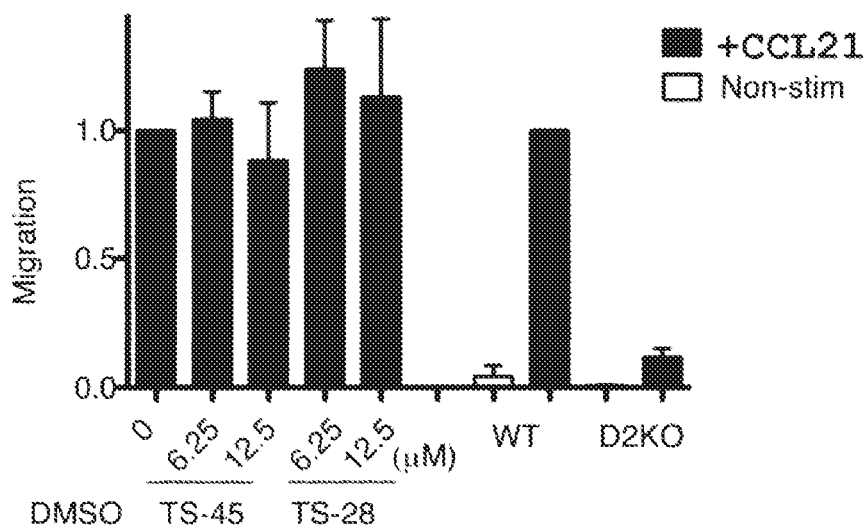
Figure 16:
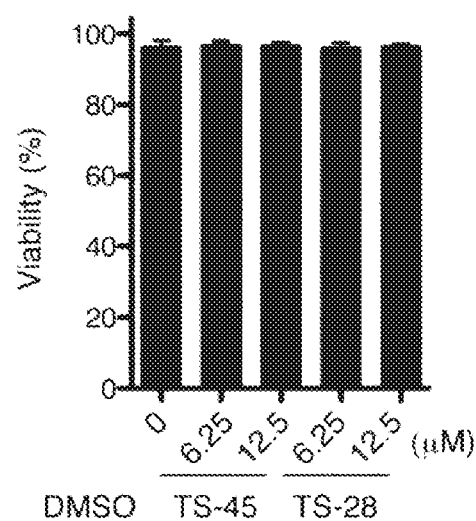

FIG. 16 is graphs showing the experimental results that confirm the effect on migration and viability of lymphocytes. (A) is a graph showing the results based on analysis of effect on the migration of T cells. The vertical axis represents the ratio of the number of migrating cells under each condition, relative to the number of wild-type T cells (with the addition of DMSO) (control) migrated towards CCL21 taken as 1. "WT" and "D2KO" on the right side of the graph indicate the ratio of the number of migrating wild-type T cells and DOCK2 knockout T cells in the presence (CCL21) or absence (−) of CCL21. (B) is a graph showing the results of T cell viability.

Figure 17B:
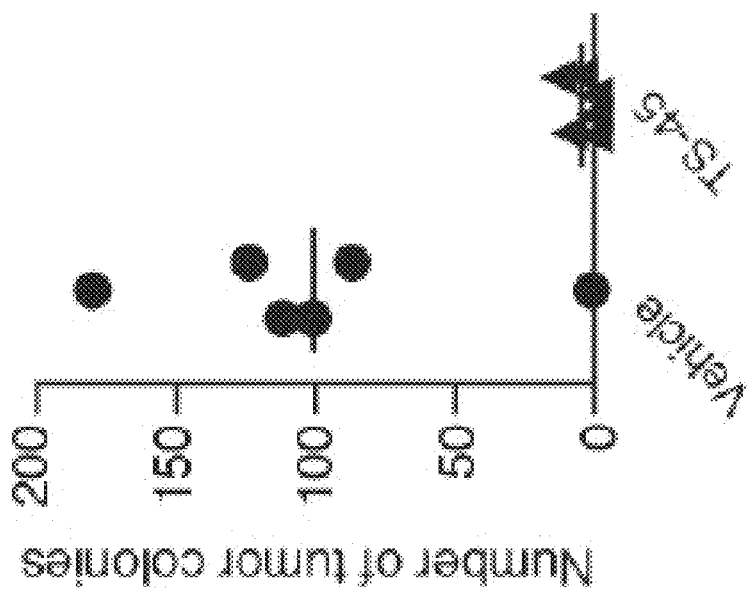
Figure 17A:
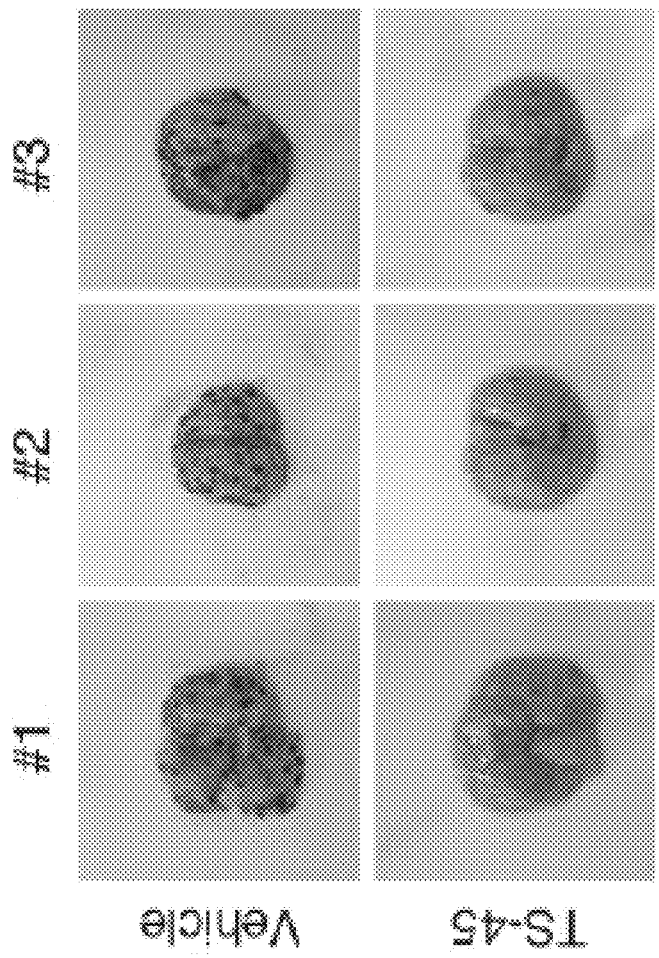
Figure 17D:
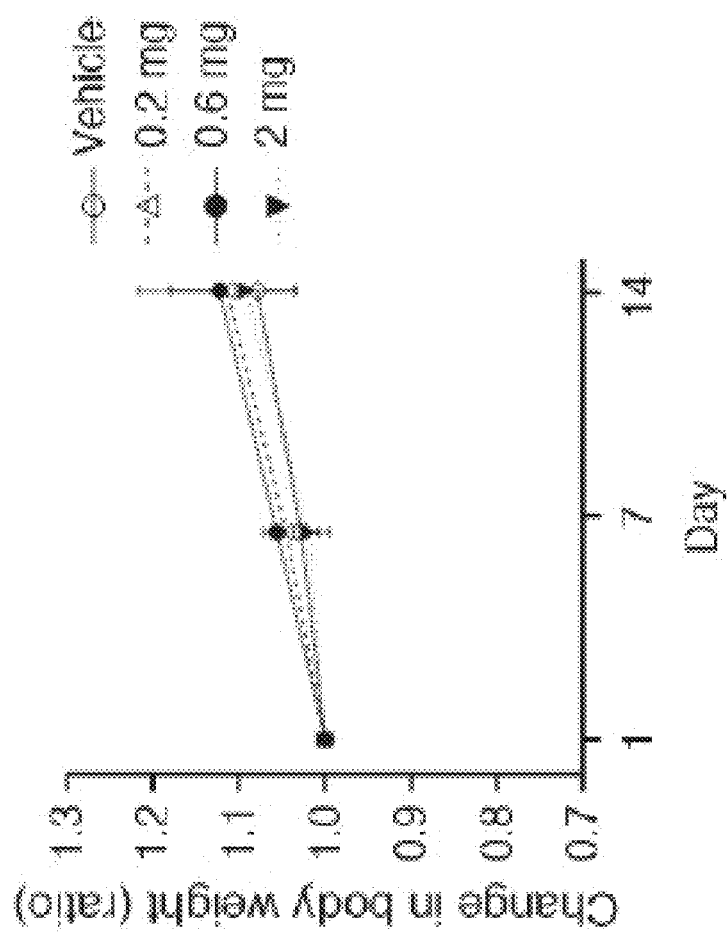
Figure 17C:
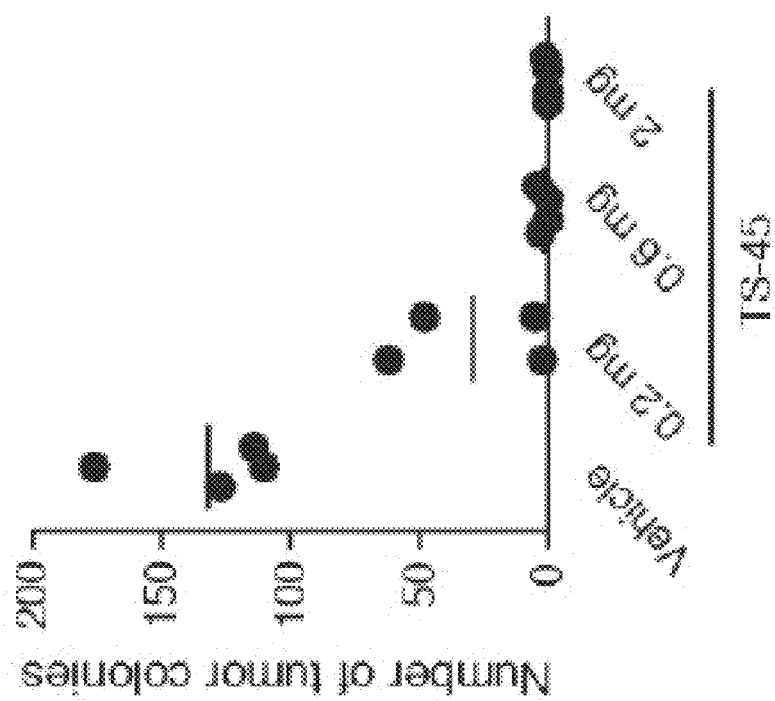

FIGS. 17(A)-(D) show the experimental results that confirm the inhibitory effect of the pyridinone compound of the present invention on lung metastasis of melanoma cells. FIG. 17(A) shows images of lungs isolated from mice into which melanoma cells were transplanted.

The upper row shows images of a control group to which a solvent was administered alone (vehicle), and the lower row shows images of a group to which TS45 was administered (TS45; 2 mg/mouse). (For each group, intravenous administration (iv) was performed 4 times in total.)

(B) is a graph showing the results obtained by counting the number of melanoma metastatic foci in each mouse in the experiment above. The vertical axis represents the number of tumor metastatic foci per lung (n=6 per group).

(C) is a graph showing dose-response curves of the inhibitory effect of TS45 on metastasis of melanoma cells to the lung. The vertical axis represents the number of the tumor metastatic foci per lung (n=4 per group). (C) shows the results of a control group to which a solvent was administered alone (vehicle), and a group to which TS45 was administered (TS45; 0.2, 0.6, or 2 mg/mouse). (For each group, intravenous administration (iv) was performed four times in total.)

(D) is a graph showing the results obtained by measuring the weight change of each mouse (n=4 per group) in the experiment above.

DESCRIPTION OF EMBODIMENTS

Pyridinone Compound or a Salt Thereof

The pyridinone compound of the present invention is represented by Formula (1) below:

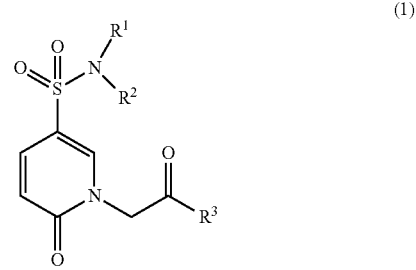

(1)

$R^1$ and $R^2$ in Formula (1) are the same or different, and each represents hydrogen, $C_{1-6}$ alkyl, or $C_{2-6}$ alkenyl, or $R^1$ and $R^2$, taken together with the nitrogen atom to which they are attached, may form a saturated 5- to 8-membered monocyclic ring, directly or via a heteroatom.

In addition to a pyridinone group and two "=O" groups, a nitrogen atom is attached to the sulfur atom in Formula (1). This nitrogen atom preferably constitutes n-propylamine, diethyleneamine, or diallylamine.

The saturated 5- to 8-membered monocyclic ring is not particularly limited. Examples of such a monocyclic ring include a pyrrolidine ring, a pyrazolidine ring, an imidazolidine ring, an (iso)thiazolidine ring, an (iso)oxazolidine ring, a piperidine ring, a piperazine ring, a morpholine ring, a thiomorpholine ring, an azepane ring, a thioazepane ring, an oxazepane ring, and the like. Of these, 5-membered monocyclic rings are preferable, with a pyrrolidine ring and an azepane ring being more preferable.

$R^3$ in Formula (1) is a group represented by any one of Formulas (2) to (6) below:

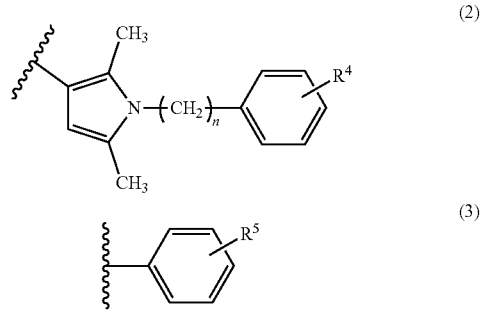

(2)

(3)

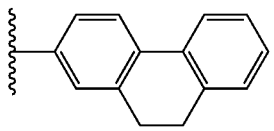
(4)

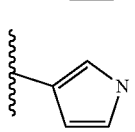
(5)

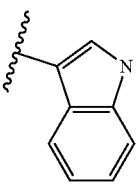
(6)

Of these groups, a group represented by Formula (2) or (3) is preferable, with a group represented by Formula (3) being more preferable.

In the group represented by Formula (2), n is 0 or 1, and is preferably 1.

In the group represented by Formula (2), $R^4$ is $C_{1-6}$ alkyl, halogen, $C_{1-6}$ alkoxy, or hydroxyl. $R^4$ is preferably a halogen atom.

In the group represented by Formula (2), $R^4$ is located at any of ortho-, meta-, or para-position, and preferably para-position, with respect to the —$(CH_2)_n$— bonding to the benzene ring.

$R^5$ in Formula (3) represents hydrogen, phenyl, or naphthyl. Of these, $R^5$ is preferably phenyl.

$R^5$ in Formula (3) is present at any position from among the ortho-, meta-, or para-position, and preferably para-position, with respect to the carbonyl group bonding to the benzene ring.

In the group represented by Formula (3), when $R^5$ is phenyl, the phenyl may be substituted with at least one, preferably 1 to 3, and more preferably 1 to 2 substituents selected from the group consisting of halogen, $C_{1-6}$ alkyl, trihalo $C_{1-6}$ alkyl, $C_{1-6}$ alkoxy, trihalo $C_{1-6}$ alkoxy, phenyl, biphenyl, aryl $C_{1-6}$ alkyl, naphthyl, nitro, and cyano. Of these substituents, halogen and/or trihalo $C_{1-6}$ alkyl are preferable.

Although not limiting to the present invention, the substituent or substituents on the phenyl may be located at any of the ortho-, meta-, or para-position, and preferably meta- and/or para-positions, with respect to the carbonyl group bonding to the benzene ring.

A naphthyl group as a substituent on the phenyl may be 1-naphthyl group or 2-naphthyl group.

In the group represented by Formula (3), in particular, when $R^5$ is phenyl as a substituent at the para-position above, and when the naphthyl group is substituting the para-position of the phenyl, the naphthyl group as a substituent on the phenyl is preferably 1-naphthyl group.

Examples of biphenyl groups as a substituent on the phenyl include, but are not particularly limited to, 3-biphenyl group, 4-biphenyl group, and the like.

The groups represented by Formulas (5) and (6) may be substituted with at least one, preferably 1 to 3, and more preferably 1 to 2, $C_{1-6}$ alkyl groups. Although not limiting to the present invention, a $C_{1-6}$ alkyl group or $C_{1-6}$ alkyl groups may replace hydrogen bonding to the carbon or nitrogen in the group represented by Formula (5) or (6).

The following are specific examples of the groups referred to in this specification.

Examples of $C_{1-6}$ alkyl groups include linear or branched $C_{1-6}$ alkyl groups, such as methyl, ethyl, n-propyl, isopropyl, n-butyl, isobutyl, tert-butyl, n-pentyl, and n-hexyl.

Examples of $C_{2-6}$ alkenyl groups include linear or branched $C_{2-6}$ alkenyl groups, such as vinyl, allyl, 2-butenyl, 3-butenyl, 1-methylallyl, 2-pentenyl, and 2-hexenyl.

Examples of halogen atoms include fluorine, chlorine, bromine, and iodine.

Examples of $C_{1-6}$ alkoxy groups include linear or branched $C_{1-6}$ alkoxy groups, such as methoxy, ethoxy, n-propoxy, isopropoxy, n-butoxy, tert-butoxy, n-pentyloxy, and n-hexyloxy.

Examples of trihalo $C_{1-6}$ alkyl groups include linear or branched $C_{1-6}$ alkyl groups substituted with 3 halogen atoms, such as trifluoromethyl, trichloromethyl, 2,2,2-trifluoroethyl, 2,2,2-trichloroethyl, 3,3,3-trifluoropropyl, and 4,4,4-trichlorobutyl.

Examples of trihalo $C_{1-6}$ alkoxy groups include linear or branched $C_{1-6}$ alkoxy groups substituted with 3 halogen atoms, such as trifluoromethoxy, trichloromethoxy, 2,2,2-trifluoroethoxy, 2,2,2-trichloroethoxy, 3,3,3-trifluoropropoxy, and 4,4,4-trichlorobutoxy.

Examples of aryl $C_{1-6}$ alkyl groups include alkyl groups whose alkyl moiety is a linear or branched chain having 1 to 6 carbon atoms, the alkyl having one to two aryl groups, such as phenyl and naphthyl. Specific examples include benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, diphenylmethyl, 2,2-diphenylethyl, 1-naphthylmethyl, 2-naphthylmethyl, and the like.

Of the pyridinone compounds represented by Formula (1) according to the present invention above, preferable embodiments include 1-(2-(1-(4-fluorobenzyl)-2,5-dimethyl-1H-pyrrol-3-yl)-2-oxoethyl)-5-(pyrrolidin-1-ylsulfonyl)pyridin-2(1H)-one [T-070444], 1-(2-oxo-2-(4'-(trifluoromethyl)-[1,1'-biphenyl]-4-yl)ethyl)-5-(pyrrolidin-1-ylsulfonyl)pyridin-2(1H)-one [TS-16], 1-(2-(4-(naphthalen-2-yl)phenyl)-2-oxoethyl)-5-(pyrrolidin-1-ylsulfonyl)pyridin-2(1H)-one [TS-28], 1-(2-oxo-2-(3'-(trifluoromethyl)-[1,1'-biphenyl]-4-yl)ethyl)-5-(pyrrolidin-1-ylsulfonyl)pyridin-2(1H)-one [TS-45], 1-(2-(3'-chloro-[1,1'-biphenyl]-4-yl)-2-oxoethyl)-5-(pyrrolidin-1-ylsulfonyl)pyridin-2(1H)-one [TS-51], and the like.

The salts of the pyridinone compounds are not particularly limited and may take the following form of salts.

Of the pyridinone compounds described above, for example, those having an acidic group can easily form a salt with a basic compound. Examples of basic compounds include metal hydroxides, such as sodium carbonate, sodium hydroxide, potassium hydroxide, calcium hydroxide, and lithium hydroxide; alkali metal carbonates, such as sodium hydrogen carbonate; alkali metal alcoholates, such as sodium methylate and potassium ethylate; and the like.

Further, of the pyridinone compounds described above, those having a basic group may easily form a salt. Examples of the acid include inorganic acids, such as nitric acid, hydrochloric acid, hydrobromic acid, and sulfuric acid; and organic acids, such as acetic acid, methanesulfonic acid, oxalic acid, maleic acid, fumaric acid, p-toluenesulfonic acid, citric acid, succinic acid, and benzoic acid.

These salts can be used in the same manner as the pyridinone compound in free form.

The pyridinone compounds above encompass isomers such as stereoisomers and enantiomers, and these isomers are also encompassed in the pyridinone compounds of the present invention.

Production Method

The method for producing a pyridinone compound represented by Formula (1) above, or a salt thereof, is not particularly limited. The following is one example of the production method for pyridinone compounds. For example, a pyridinone compound of the present invention is produced by reacting a compound represented by Formula (7) below:

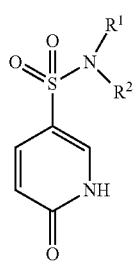

(7)

wherein $R^1$ and $R^2$ are as defined above,
with a compound represented by Formula (8) below:

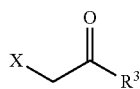

(8)

wherein X and $R^3$ are as defined above,
in the presence of a reducing agent.

The conditions for the reaction above may be arbitrarily determined, and the reaction conditions used in, for example, Production Example 58 in the Examples below may be applicable.

The compounds represented by Formulas (7) and (8), which are known compounds, can be easily produced from known and available compounds.

Of the pyridinone compounds of the present invention, a pyridinone compound in which $R^3$ in Formula (1) is a group represented by any one of Formulas (3) to (6) is produced by the method described in Production Example 1 in the Examples below as is, or by arbitrarily modifying this method.

The pyridinone compound of the present invention produced by the method described above is isolated and/or purified from the reaction mixture by using a known isolation and/or purification means. Examples of the separation and purification means include distillation, recrystallization, solvent extraction, column chromatography, ion-exchange chromatography, gel chromatography, affinity chromatography, preparative thin-layer chromatography, and the like.

DOCK1-Selective Inhibitor

The DOCK1-selective inhibitor according to the present invention comprises the pyridinone compound according to the present invention or a salt thereof.

DOCK1 inhibition means inhibiting DOCK1 activity. The activity is not particularly limited. Examples of the activity to be inhibited include the Rac-GDP-to-Rac-GTP conversion activity (GEF activity). The GEF activity is easily confirmed by using the method shown in the Examples below, or a known method in accordance with this method.

The term "selective" as used herein does not limit the inhibition to only DOCK1 inhibition, and may also include inhibition of the activities above of DOCK5 and/or DOCK2, as in DOCK1, as long as the DOCK1 activity is more significantly inhibited, compared to the activities of DOCK2 or DOCK5, which are DOCK-A subfamily members.

As the DOCK1-selective inhibitor according to the present invention, the pyridinone compound of the present invention or a salt thereof may be used as is. It is also possible to incorporate other components such as additives that are usually used in this field. Specific additives and the amount of the additives incorporated in the DOCK1-selective inhibitor are not particularly limited, and may be arbitrarily selected with reference to, for example, the additives and the amount mentioned in the Pharmaceutical Composition section below.

The DOCK1-selective inhibitor according to the present invention is obtained by the method of the present invention for screening the DOCK1-selective inhibitor from test substances mentioned later.

Pharmaceutical Composition

The pharmaceutical composition according to the present invention comprises the pyridinone compound according to the present invention described above, or a pharmaceutically acceptable salt thereof.

The pharmaceutically acceptable salt may be arbitrarily selected in view of the Pyridinone Compound or a Salt Thereof section above.

The pharmaceutical composition of the present invention may consist only of the pyridinone compound of the present invention or a pharmaceutically acceptable salt thereof. Alternatively, the pyridinone compound of the present invention, or a pharmaceutically acceptable salt thereof, may be combined with an arbitrary carrier or additives using known methods to prepare a pharmaceutical composition in the form suitable for a desired application, such as administration route and mode of administration.

Specific examples of dosage forms include tablets, pills, powders, solutions, suspensions, emulsions, granules, capsules, suppositories, infections (e.g., solution and suspension), and the like.

The amount of the pyridinone compound of the present invention, or a pharmaceutically acceptable salt thereof, incorporated into the pharmaceutical composition of the present invention is not particularly limited, and is arbitrarily selected from a range of, for example, about 0.001 wt % to 99 wt % or less, preferably about 0.01 wt % to 50 wt %, and more preferably about 0.05 wt % to 10 wt %, per 100 wt % of the pharmaceutical composition.

The disease to be treated by the pharmaceutical composition of the present invention is not particularly limited. Examples of the disease include cancer. According to the Examples shown below, the pyridinone compounds of the present invention exert an inhibitory effect on cancer cell invasion; thus, the cancer is preferably a metastatic cancer.

The Examples shown below also demonstrates that the pyridinone compounds of the present invention exert an inhibitory effect on macropinocytosis in cancer cells. Therefore, the pharmaceutical composition of the present invention is preferably used particularly for cancer of types that undergo the phenomenon of macropinocytosis.

The subject for administration of the pharmaceutical composition of the present invention may be a patient suffering from the disease above or a human capable of suffering from the disease.

The dose of the pharmaceutical composition of the present invention, converted as the pyridinone compound of the present invention or a pharmaceutically acceptable salt thereof, is usually about 5 mg to 500 mg, preferably about 5 mg to 250 mg, more preferably about 5 mg to 100 mg, and still more preferably about 5 mg to 50 mg, per day.

It is possible for the pharmaceutical composition of the present invention to contain the DOCK1-selective inhibitor described above. In relation to this pharmaceutical composition, the amount of the DOCK1-selective inhibitor, the disease to be treated, the dosage form, the target for administration, the dose, and the like may be as described above.

Screening Method

The screening method of the present invention is a method for screening a DOCK1-selective inhibitor from test substances. The method comprises the following steps 1 and 2:

step 1 of adding test substances to cells; and
step 2 of selecting a substance that selectively inhibits a function of DOCK1 in the cells from the test substances added in step 1.

The test substances are not particularly limited. Examples include chemical libraries, hybridoma-produced antibody libraries, various naturally-occurring extracts, and compositions comprising combinations thereof.

The cells in step 1 are not particularly limited. For example, the cells may be invasive cells. In this case, selective inhibition of the function of DOCK1 in step 2 is considered to be an inhibition of the invasiveness of the cells to which the test substances have been added. Examples of the invasive cells include cancer cell lines and the like.

The cells in step 1 may also be, for example, non-immune cells. In this case, the selective inhibition of the function of DOCK1 in step 2 is considered to be an inhibition of the dorsal ruffle formation while not affecting the peripheral ruffle formation in the cells after the addition of the test substances to the cells. Examples of the non-immune cells include epithelial cells and the like.

Needless to say, the phrase "not affecting the peripheral ruffle formation" is not interpreted to mean that the degree of ruffle formation in the cells is the same before and after the addition of the test substances.

Alternatively, the cells in step 1 may also be, for example, immune cells. In this case, the selective inhibition of the function of DOCK1 in step 2 is considered to not affect the migration response of proteins belonging to the DOCK families, other than DOCK1, in the cells after the addition of the test substances to the cells. Examples of the immune cells include lymphocytes and the like.

Examples of proteins belonging to the DOCK families, other than DOCK1, include, but are not particularly limited to, proteins belonging to the DOCK-A subfamily, proteins belonging to the DOCK-B subfamily, proteins belonging to the DOCK-C subfamily, proteins belonging to the DOCK-D subfamily, and the like.

Of these, DOCK2 and/or DOCK5, which are proteins belonging to the DOCK-A subfamily, are preferable, with DOCK2 being more preferable.

Irrespective of the type of the cells used in step 1, the selective inhibition of the function of DOCK1 in step 2 may be considered to be a selective inhibition of the GEF activity of DOCK1 in the cells to which the test substances have been added.

These screening methods can be easily performed by using the methods shown in the Examples below or known methods in accordance with these methods.

EXAMPLES

The present invention is described below in more detail with reference to the Production Examples for the pyridinone compounds of the present invention and Test Examples for the pyridinone compounds of the present invention. However, the present invention is not limited to these.

First, the pyridinone compounds represented by chemical formulas shown in FIGS. 1 to 7 were produced. The following are the names of the pyridinone compounds represented by these chemical formulas.

T070444 1-(2-(1-(4-fluorobenzyl)-2,5-dimethyl-1H-pyrrol-3-yl)-2-oxoethyl)-5-(pyrrolidin-1-ylsulfonyl)pyridin-2 (1H)-one NT-01 1-(2-(1-benzyl-2,5-dimethyl-1H-pyrrol-3-yl)-2-oxoethyl)-5-(pyrrolidin-1-ylsulfonyl)pyridin-2(1H)-one NT-02 1-(2-(2,5-dimethyl-1-(4-methylbenzyl)-1H-pyrrol-3-yl)-2-oxoethyl)-5-(pyrrolidin-1-ylsulfonyl)pyridin-2 (1H)-one NT-03 1-(2-(1-(4-chlorobenzyl)-2,5-dimethyl-1H-pyrrol-3-yl)-2-oxoethyl)-5-(pyrrolidin-1-ylsulfonyl)pyridin-2 (1H)-one NT-04 1-(2-(4-bromobenzyl)-2,5-dimethyl-1H-pyrrol-3-yl)-2-oxoethyl)-5-(pyrrolidin-1-ylsulfonyl)pyridin-2(1H)-one NT-05 1-(2-(1-(4-methoxybenzyl)-2,5-dimethyl-1H-pyrrol-3-yl)-2-oxoethyl)-5-(pyrrolidin-1-ylsulfonyl)pyridin-2 (1H)-one NT-06 1-(1-(4-fluorobenzyl)-2,5-dimethyl-1H-pyrrol-3-yl)-2-phenylethanone NT-07 1-(2-(1-benzyl-2,5-dimethyl-1H-pyrrol-3-yl)-2-oxoethyl)pyridin-2(1H)-one NT-08 1-(2-(1-(4-fluorobenzyl)-2,5-dimethyl-1H-pyrrol-3-yl)-2-oxoethyl)-5-(piperidin-1-ylsulfonyl)pyridin-2(1H)-one NT-09 5-(azepan-1-ylsulfonyl)-1-(2-(1-(4-fluorobenzyl)-2,5-dimethyl-1H-pyrrol-3-yl)-2-oxoethyl)pyridin-2(1H)-one NT-10 1-(2-(1-(4-fluorobenzyl)-2,5-dimethyl-1H-pyrrol-3-yl)-2-oxoethyl)-5-(thiomorpholinosulfonyl)pyridin-2 (1H)-one NT-11 1-(2-(1-(4-fluorobenzyl)-2,5-dimethyl-1H-pyrrol-3-yl)-2-oxoethyl)-5-(morpholinosulfonyl)pyridin-2(1H)-one NT-12 N,N-diethyl-1-(2-(1-(4-fluorobenzyl)-2,5-dimethyl-1H-pyrrol-3-yl)-2-oxoethyl)-6-oxo-1,6-dihydropyridine-3-sulfonamide NT-13 1-(2-(1-(4-hydroxybenzyl)-2,5-dimethyl-1H-pyrrol-3-yl)-2-oxoethyl)-5-(pyrrolidin-1-ylsulfonyl)pyridin-(1H)-one NT-15 1-(2-oxo-2-phenylethyl)-5-(pyrrolidin-1-ylsulfonyl)pyridin-2(1H)-one TS-01 1-(2-(1-methyl-1H-indol-3-yl)-2-oxoethyl)-5-(pyrrolidin-1-ylsulfonyl)pyridin-2(1H)-one TS-02 1-(2-(1,2-dimethyl-1H-indol-3-yl)-2-oxoethyl)-5-(pyrrolidin-1-ylsulfonyl)pyridin-2(1H)-one TS-03 1-(2-oxo-2-(1,2,5-trimethyl-1H-pyrrol-3-yl)ethyl)-5-(pyrrolidin-1-ylsulfonyl)pyridin-2(1H)-one TS-07 1-(2-(1-(4-fluorophenyl)-2,5-dimethyl-1H-pyrrol-3-yl)-2-oxoethyl)-5-(pyrrolidin-1-ylsulfonyl)pyridin-2 (1H)-one TS-08 1-(2-(1-(4-methoxyphenyl)-2,5-dimethyl-1H-pyrrol-3-yl)-2-oxoethyl)-5-(pyrrolidin-1-ylsulfonyl)pyridin-2 (1H)-one TS-09 1-(2-([1,1'-biphenyl]-4-yl)-2-oxoethyl)-5-(pyrrolidin-1-ylsulfonyl)pyridin-2(1H)-one TS-10 N,N-diallyl-1-(2-(1-fluorobenzyl)-2,5-dimethyl-1H-pyrrol-3-yl)-2-oxoethyl)-6-oxo-1,6-dihydropyridine-3-sulfonamide TS-11 1-(2-(2',6'-dimethyl-[1,1'-biphenyl]-4-yl)-2-oxoethyl)-5-(pyrrolidin-1-ylsulfonyl)pyridin-2(1H)-one TS-12 1-(2-(2'-methyl-[1,1'-biphenyl]-4-yl)-2-oxoethyl)-5-(pyrrolidin-1-ylsulfonyl)pyridin-2(1H)-one TS-13 1-(2-([1,1'-biphenyl]-3-yl)-2-oxoethyl)-5-(pyrrolidin-1-ylsulfonyl)pyridin-2(1H)-one TS-14 1-(2-(2'-methyl-[1,1'-biphenyl]-3-yl)-2-oxoethyl)-5-(pyrrolidin-1-ylsulfonyl)pyridin-2(1H)-one TS-15 1-(2-(2',6'-dimethyl-[1,1'-biphenyl]-3-yl)-2-oxoethyl)-5-(pyrrolidin-1-ylsulfonyl)pyridin-2(1H)-one TS-16 1-(2-oxo-2-(4'-(trifluoromethyl)-[1,1'-biphenyl]-4-yl)ethyl)-5-(pyrrolidin-1-ylsulfonyl)pyridin-2(1H)-one TS-17 1-(2-(4'-methoxy-[1,1'-biphenyl]-4-yl)-2-oxoethyl)-5-(pyrrolidin-1-ylsulfonyl)pyridin-2(1H)-one TS-18 1-(2-oxo-2-(4'-(trifluoromethoxy)-[1,1'-biphenyl]-4-yl)ethyl)-5-(pyrrolidin-1-ylsulfonyl)pyridin-2(1H)-one TS-19 1-(2-(4'-nitro-[1,1'-biphenyl]-4-yl)-2-oxoethyl)-5-(pyrrolidin-1-ylsulfonyl)pyridin-2(1H)-one TS-20 4'-(2-(2-oxo-5-(pyrrolidin-1-ylsulfonyl)pyridin-1(2H)-yl)acetyl)-[1,1'-biphenyl]-4-carbonitrile TS-21 1-(2-(9,10-dihydrophenanthren-2-yl)-2-oxoethyl)-5-(pyrrolidin-1-ylsulfonyl)pyridin-2(1H)-one TS-22 1-(2-([1,1':4',1''-terphenyl]-4-yl)-2-oxoethyl)-5-(pyrrolidin-1-ylsulfonyl)pyridin-2(1H)-one TS-23 1-(2-(4'-(dimethylamino)-[1,1'-biphenyl]-4-yl)-2-oxoethyl)-5-(pyrrolidin-1-ylsulfonyl)pyridin-2(1H)-one TS-24 1-(2-(4'-fluoro-[1,1'-biphenyl]-4-yl)-2-oxoethyl)-5-(pyrrolidin-1-ylsulfonyl)pyridin-2(1H)-one TS-25 1-(2-(4'-(tert-butyl)-[1,1'-biphenyl]-4-yl)-2-oxoethyl)-5-(pyrrolidin-1-ylsulfonyl)pyridin-2(1H)-one TS-26 1-(2-(4'-methyl-[1,1'-biphenyl]-4-yl)-2-oxoethyl)-5-(pyrrolidin-1-ylsulfonyl)pyridin-2(1H)-one TS-27 1-(2-(4'-chloro-[1,1'-biphenyl]-4-yl)-2-oxoethyl)-5-(pyrrolidin-1-ylsulfonyl)pyridin-2(1H)-one TS-28 1-(2-(4-(naphthalen-2-yl)phenyl)-2-oxoethyl)-5-(pyrrolidin-1-ylsulfonyl)pyridin-2(1H)-one TS-29 1-(2-(4-(naphthalen-1-yl)phenyl)-2-oxoethyl)-5-(pyrrolidin-1-ylsulfonyl)pyridin-2(1H)-one TS-30 1-(2-([1,1':4',1''-terphenyl]-3-yl)-2-oxoethyl)-5-(pyrrolidin-1-ylsulfonyl)pyridin-2(1H)-one TS-31 1-(2-([1,1':4',1'':4'',1'''-quaterphenyl]-3-yl)-2-oxoethyl)-5-(pyrrolidin-1-ylsulfonyl)pyridin-2(1H)-one TS-32 1-(2-([1,1':4',1'':4'',1'''-quaterphenyl]-4-yl)-2-oxoethyl)-5-(pyrrolidin-1-ylsulfonyl)pyridin-2(1H)-one TS-34 1-(2-([1,1':3',1''-terphenyl]-4-yl)-2-oxoethyl)-5-(pyrrolidin-1-ylsulfonyl)pyridin-2(1H)-one TS-35 1-(2-([1,1':3',1''-terphenyl]-3-yl)-2-oxoethyl)-5-(pyrrolidin-1-ylsulfonyl)pyridin-2(1H)-one TS-36 1-(2-oxo-2-(5'-phenyl-[1,1':3',1''-terphenyl]-4-yl)ethyl)-5-(pyrrolidin-1-ylsulfonyl)pyridin-2(1H)-one TS-37 1-(2-oxo-2-(5'-phenyl-[1,1':3',1''-terphenyl]-3-yl)ethyl)-5-(pyrrolidin-1-ylsulfonyl)pyridin-2(1H)-one TS-38 1-(2-(4'-(naphthalen-2-yl)-[1,1'-biphenyl]-4-yl)-2-oxoethyl)-5-(pyrrolidin-1-ylsulfonyl)pyridin-2(1H)-one TS-39 1-(2-(4'-(naphthalen-1-yl)-[1,1'-biphenyl]-4-yl)-2-oxoethyl)-5-(pyrrolidin-1-ylsulfonyl)pyridin-2(1H)-one TS-40 1-(2-(4'-benzyl-[1,1'-biphenyl]-4-yl)-2-oxoethyl)-5-(pyrrolidin-1-ylsulfonyl)pyridin-2(1H)-one TS-41 1-(2-(4'-(naphthalen-1-yl)-[1,1'-biphenyl]-3-yl)-2-oxoethyl)-5-(pyrrolidin-1-ylsulfonyl)pyridin-2(1H)-one TS-42 1-(2-(4'-(naphthalen-2-yl)-[1,1'-biphenyl]-3-yl)-2-oxoethyl)-5-(pyrrolidin-1-ylsulfonyl)pyridin-2(1H)-one TS-43 1-(2-(4'-benzyl-[1,1'-biphenyl]-3-yl)-2-oxoethyl)-5-(pyrrolidin-1-ylsulfonyl)pyridin-2(1H)-one TS-44 1-(2-oxo-2-(2'-(trifluoromethyl)-[1,1'-biphenyl]-4-yl)ethyl)-5-(pyrrolidin-1-ylsulfonyl)pyridin-2(1H)-one TS-45 1-(2-oxo-2-(3'-(trifluoromethyl)-[1,1'-biphenyl]-4-yl)ethyl)-5-(pyrrolidin-1-ylsulfonyl)pyridin-2(1H)-one TS-46 1-(2-(2'-methoxy-[1,1'-biphenyl]-4-yl)-2-oxoethyl)-5-(pyrrolidin-1-ylsulfonyl)pyridin-2(1H)-one TS-47 1-(2-(3-methoxy-[1,1'-biphenyl]-4-yl)-2-oxoethyl)-5-(pyrrolidin-1-ylsulfonyl)pyridin-2(1H)-one TS-48 1-(2-(2'-fluoro-[1,1'-biphenyl]-4-yl)-2-oxoethyl)-5-(pyrrolidin-1-ylsulfonyl)pyridin-2(1H)-one TS-49 1-(2-(3-fluoro-[1,1'-biphenyl]-4-yl)-2-oxoethyl)-5-(pyrrolidin-1-ylsulfonyl)pyridin-2(1H)-one TS-50 1-(2-(2-chloro-[1,1'-biphenyl]-4-yl)-2-oxoethyl)-5-(pyrrolidin-1-ylsulfonyl)pyridin-2(1H)-one TS-51 1-(2-(3-chloro-[1,1'-biphenyl]-4-yl)-2-oxoethyl)-5-(pyrrolidin-1-ylsulfonyl)pyridin-2(1H)-one TS-52 1-(2-(4'-chloro-[1,1'-biphenyl]-4-yl)-2-oxoethyl)-5-(pyrrolidin-1-ylsulfonyl)pyridin-2(1H)-one TS-53 1-(2-(4'-chloro-2'-(trifluoromethyl)-[1,1'-biphenyl]-4-yl)-2-oxoethyl)-5-(pyrrolidin-1-ylsulfonyl)pyridin-2(1H)-one TS-54 1-(2-(4'-chloro-3'-(trifluoromethyl)-[1,1'-biphenyl]-4-yl)-2-oxoethyl)-5-(pyrrolidin-1-ylsulfonyl)pyridin-2(1H)-one TS-55 1-(2-(4-(4-chlorophenyl)piperazin-1-yl)-2-oxoethyl)-5-(pyrrolidin-1-ylsulfonyl)pyridin-2(1H)-one TS-56 1-(2-(4-chloro-[1,1'-biphenyl]-4-yl)-2-oxoethyl)-6-oxo-N-propyl-1,6-dihydropyridine-3-sulfonamide TS-57 1-(2-(3,5'-bis(trifluoromethyl)-[1,1'-biphenyl]-4-yl)-2-oxoethyl)-5-(pyrrolidin-1-ylsulfonyl)pyridin-2(1H)-one TS-58 1-(2-(4'-chloro-2'-methyl-[1,1'-biphenyl]-4-yl)-2-oxoethyl)-5-(pyrrolidin-1-ylsulfonyl)pyridin-2(1H)-one TS-59 1-(2-(4-methoxy-2-methyl-[1,1'-biphenyl]-2-oxoethyl)-5-(pyrrolidin-1-ylsulfonyl)pyridin-2(1H)-one TS-60 1-(2-(2'-chloro-4'-methoxy-[1,1'-biphenyl]-4-yl)-2-oxoethyl)-5-(pyrrolidin-1-ylsulfonyl)pyridin-2(1H)-one TS-61 5-(azepan-1-ylsulfonyl)-1-(2-oxo-2-(3'-(trifluoromethyl)-[1,1'-biphenyl]-4-yl)ethyl)pyridin-2(1H)-one TS-62 5-(azepan-1-ylsulfonyl)-1-(2-oxo-2-(4'-(trifluoromethyl)-[1,1'-biphenyl]-4-yl)ethyl)pyridin-2(1H)-one TS-63 5-(azepan-1-ylsulfonyl)-1-(2-(4'-chloro-[1,1'-biphenyl]-4-yl)-2-oxoethyl)pyridin-2(1H)-one TS-64 5-(azepan-1-ylsulfonyl)-1-(2-(4'-chloro-2'-methyl-[1,1'-biphenyl]-4-yl)-2-oxoethyl)pyridin-2(1H)-one TS-65 N,N-diethyl-6-oxo-1-(2-oxo-2-(3'-(trifluoromethyl)-[1,1'-biphenyl]-4-yl)ethyl)-1,6-dihydropyridine-3-sulfonamide TS-66 N,N-diethyl-6-oxo-1-(2-oxo-2-(4'-(trifluoromethyl)-[1,1'-biphenyl]-4-yl)ethyl)-1,6-dihydropyridine-3-sulfonamide TS-67 1-(2-(4'-chloro-[1,1'-biphenyl]-4-yl)-2-oxoethyl)-N,N-diethyl-6-oxo-1,6-dihydropyridine-3-sulfonamide TS-68 1-(2-(2'-chloro-4'-methoxy-[1,1'-biphenyl]-4-yl)-2-oxoethyl)-5-(pyrrolidin-1-ylsulfonyl)pyridin-2(1H)-one The following are Production Examples for the above pyridinone compounds. The rest of the compounds were produced in accordance with Production Examples 2 to 74.

Production Example 1

Production of 1-(2-oxo-2-(3'-(trifluoromethyl)-[1,1'-biphenyl]-4-yl)ethyl)-5-(pyrrolidin-1-ylsulfonyl)pyridin-2(1H)-one (Compound TS-45)

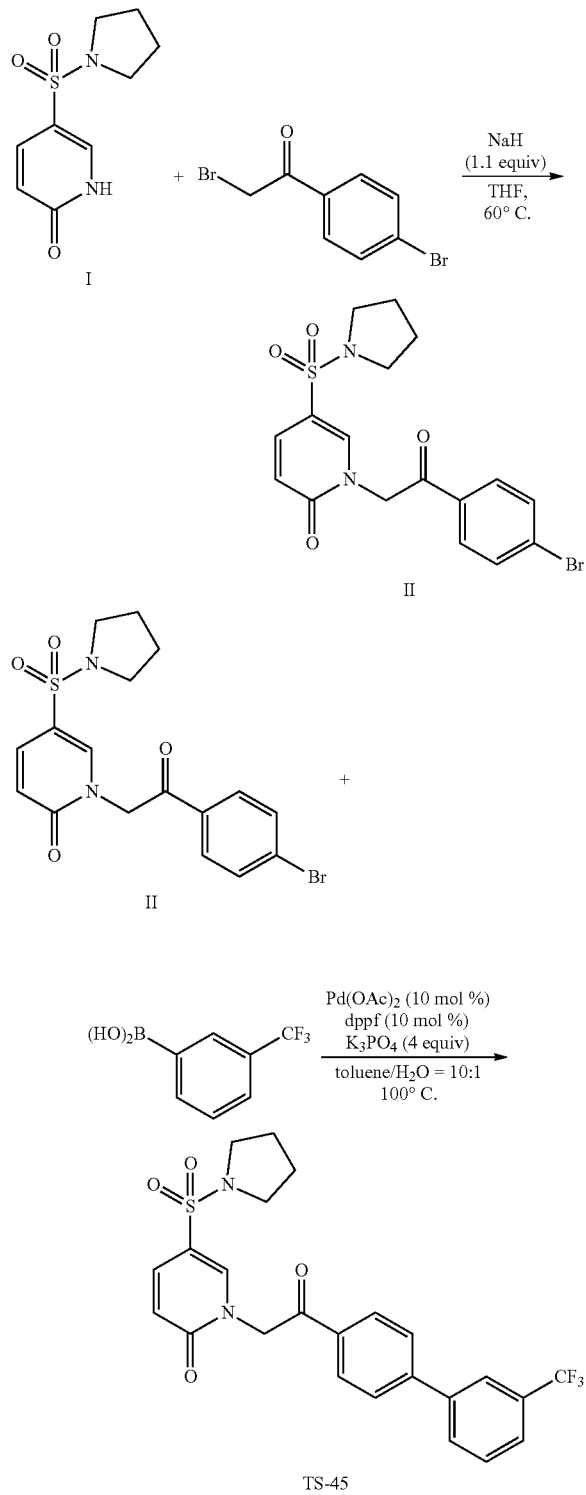

(1) Synthesis of 1-(2-(4-bromophenyl)-2-oxoethyl)-5-(pyrrolidin-1-ylsulfonyl)pyridin-2(1H)-one (Compound II)

5-(Pyrrolidin-1-ylsulfonyl)pyridin-2(1H)-one (compound I: 2.28 g, 10 mmol) was dissolved in 100 mL of tetrahydrofuran (THF), to which sodium hydride (purity: 60%, 11 mmol) was added at room temperature, followed by stirring at 60° C. for 60 minutes. A solution of 2,4'-dibromoacetophenone in THF (50 ml, 12 mmol) was added to the resulting mixture, followed by stirring at 60° C. for 90 minutes. After the reaction solution was cooled to room temperature, water was carefully added to stop the reaction, the obtained reaction product was extracted with $CH_2Cl_2$, and the collected organic phase was sequentially washed with water and brine. The organic phase was then dehydrated with $MgSO_4$, and the solvent was evaporated under reduced pressure. The obtained crude product was purified by silica gel column chromatography ($CH_2Cl_2$/ethyl acetate=1:1), and title compound II was obtained as a light-yellow solid (4.13 g, yield: 97%). The following are the physicochemical properties of the obtained compound II.

$^1$H NMR (500 MHz, Acetone-$d_6$) δ 8.27 (d, J=2.6 Hz, 1H), 8.03-8.06 (m, 2H), 7.80-7.82 (m, 2H), 7.77 (dd, J=9.5, 2.6 Hz, 1H), 6.55 (d, J=9.5 Hz, 1H), 5.69 (s, 2H), 3.22-3.27 (m, 4H), 1.82-1.87 (m, 4H);

$^{13}$C NMR (125 MHz, Acetone-$d_6$) δ 197.4, 166.9, 149.0, 143.1, 139.9, 138.1, 135.8, 134.3, 125.6, 121.4, 60.7, 53.9, 31.0.

(2) Production of 1-(2-oxo-2-(3'-(trifluoromethyl)-[1,1'-biphenyl]-4-yl)ethyl)-5-(pyrrolidin-1-ylsulfonyl)pyridin-2(1H)-one (Compound TS-45)

Compound II (1.00 g, 2.35 mmol) produced in (1), palladium acetate (52.8 mg, 0.235 mmol), and 1,1'-bis(diphenylphosphinoferrocene) (dppf, 130 mg, 0.235 mmol) were dissolved in toluene (23.5 mL). After the mixture was stirred at 100° C. for 5 minutes, $K_3PO_4$ (2.00 mg, 9.40 mmol) dissolved in degassed distilled water (2.35 ml) was added to the mixture. After the reaction mixture was stirred at 100° C. for 5 minutes, [3-(trifluoromethyl)phenyl]boronic acid (892 mg, 4.70 mmol) was added, followed by stirring at 100° C. for 8 hours. Subsequently, the reaction product was extracted twice with $CH_2Cl_2$. The collected organic phase was washed with water and brine, and dehydrated with $MgSO_4$. The solvent was evaporated under reduced pressure, and the obtained crude product was purified by silica gel column chromatography ($CH_2Cl_2$/ethyl acetate=5:1), and title compound TS-45 was produced as a yellow waxy solid (953 mg, yield: 83%). The following are physicochemical properties of the obtained compound TS-45.

$^1$H NMR (500 MHz, CDCl$_3$) δ 8.09-8.14 (m, 2H), 7.93 (d, J=2.6 Hz, 1H), 7.88 (s, 1H), 7.82 (d, J=7.7 Hz, 1H), 7.74-7.79 (m, 2H), 7.68 (dd, J=9.6, 2.6 Hz, 1H), 7.68 (dd, J=9.6, 2.6 Hz, 1H), 7.62 (dd, J=7.7, 7.7 Hz, 1H), 6.66 (d, J=9.6 Hz, 1H), 5.47 (s, 2H), 3.29-3.34 (m, 4H), 1.88-1.94 (m, 4H);

$^{13}$C NMR (125 MHz, CDCl$_3$) δ 191.1, 161.6, 145.5, 142.2, 140.4, 137.0, 133.7, 131.6 (q, J=32.4 Hz), 130.7, 129.7, 129.0, 127.8, 125.3 (q, J=3.6 Hz) 124.2 (q, J=3.6 Hz), 124.1 (q, J=272.3 Hz), 120.7, 116.4, 54.4, 48.2, 25.5;

HRMS (ESI-MS) calcd for $C_{24}H_{21}F_3N_2NaO_4S^+$ [M+Na$^+$] 513.1072 found 513.1078.

Production Example 2

Production of 1-(2-(3'-chloro-[1,1'-biphenyl]-4-yl)-2-oxoethyl)-5-(pyrrolidin-1-ylsulfonyl)pyridin-2(1H)-one (Compound TS-51)

Compound TS-51 was produced as a light-brown oil with a yield of 71% in a similar manner as described in Production Example 1(2), using compound II and (3-chlorophenyl)boronic acid. The following are physicochemical properties of the obtained compound TS-51.

$^1$H NMR (500 MHz, CDCl$_3$) δ 8.09 (d, J=8.0 Hz, 2H), 7.92 (d, J=2.0 Hz, 1H), 7.73 (d, J=8.0 Hz, 2H), 7.68 (dd, J=9.8, 2.0 Hz, 1H), 7.63 (d, J=0.9 Hz, 1H), 7.50-7.56 (m, 1H), 7.38-7.46 (m, 2H), 6.66 (d, J=9.8 Hz, 1H), 5.46 (s, 2H), 3.25 (m, 4H), 1.85-2.00 (m, 4H);

$^{13}$C NMR (125 MHz, CDCl$_3$) δ 91.0, 161.6, 145.9, 142.1, 141.4, 137.1, 135.2, 133.6, 130.5, 129.0, 128.8, 127.9, 127.6, 125.6, 120.8, 116.6, 54.3, 48.3, 25.6;

HRMS (ESI-MS) calcd for $C_{23}H_{21}ClN_2NaO_4S^+$ [M+Na$^+$] 479.0808. found 479.0814.

Production Example 3

Production of 1-(2-(4-(naphthalen-2-yl)phenyl)-2-oxoethyl)-5-(pyrrolidin-1-ylsulfonyl)pyridin-2(1H)-one (Compound TS-28)

Compound TS-28 was produced as a yellow wax with a yield of 69% in a similar manner as described in Production Example 1(2), using Compound II and (naphthalen-2-yl)boronic acid. The following are physicochemical properties of the obtained compound TS-28.

$^1$H NMR (500 MHz, CDCl$_3$) δ 8.13 (s, 1H), 8.12 (s, 2H), 7.84-8.00 (m, 6H), 7.77 (d, J=7.1 Hz, 1H), 7.68 (dd, J=9.6, 1.9 Hz, 1H), 7.50-7.58 (m, 2H), 6.66 (d, J=9.7 Hz, 1H), 5.49 (s, 2H), 3.26-3.36 (m, 4H), 1.86-1.96 (m, 4H);

$^{13}$C NMR (125 MHz, CDCl$_3$, CDCl$_3$) δ 191.3, 161.8, 147.5, 142.4, 137.3, 137.1, 133.9, 133.6, 133.3, 129.3, 129.2, 128.8, 128.3, 128.1, 127.1, 127.1, 127.0, 125.4, 121.0, 116.8, 54.6, 48.5, 25.8;

HRMS (ESI-MS) calcd for $C_{27}H_{24}N_2NaO_4S^+$ [M+Na$^+$] 495.1354. found 495.1339.

Production Example 4

Production of 1-(2-(4'-chloro-[1,1'-biphenyl]-4-yl)-2-oxoethyl)-5-(pyrrolidin-1-ylsulfonyl)pyridin-2(1H)-one (Compound TS-27)

Compound TS-27 was produced as a colorless solid with a yield of 71% in a similar manner as described in Production Example 1(2), using compound II and (4-chlorophenyl)boronic acid. The following are physicochemical properties of the obtained compound TS-27.

$^1$H NMR (500 MHz, CDCl$_3$) δ 8.08 (d, J=8.3 Hz, 2H), 7.92 (1H, d, J=2.4 Hz, 1H), 7.72 (d, J=8.3 Hz, 2H), 7.68 (dd, J=9.6, 2.4 Hz, 1H), 7.58 (d, J=8.3 Hz, 2H), 7.47 (d, J=8.3 Hz, 2H), 6.66 (d, J=9.6 Hz, 1H), 5.46 (s, 2H), 3.25-3.36 (m, 4H), 1.85-1.96 (m, 4H);

$^{13}$C NMR (125 MHz, CDCl$_3$) δ 191.0, 161.6, 146.1, 142.1, 138.0, 137.0, 135.1, 133.3, 129.4, 129.0, 128.7, 127.7, 120.8, 116.6, 54.3, 48.3, 25.6;

HRMS (ESI-MS) calcd for $C_{23}H_{21}ClN_2NaO_4S^+$ [M+Na$^+$] 479.0808 found 479.0911.

Production Example 5

Production of 1-(2-oxo-2-(2'-(trifluoromethyl)-[1,1'-biphenyl]-4-yl)ethyl)-5-(pyrrolidin-1-ylsulfonyl)pyridin-2(1H)-one (Compound TS-44)

Compound TS-44 was produced as a colorless solid with a yield of 99% in a similar manner as described in Production Example 1(2), using compound II and [2-(trifluoromethyl)phenyl]boronic acid. The following are physicochemical properties of the obtained compound TS-44.

$^1$H NMR (500 MHz, CDCl$_3$) δ 8.04-8.08 (m, 2H), 7.93 (d, J=2.6 Hz, 1H), 7.79 (d, J=7.8 Hz, 1H), 7.68 (dd, J=9.5, 2.6 Hz, 1H), 7.61 (dd, J=7.5 Hz, 1H), 7.48-7.56 (m, 3H), 7.33 (d, J=7.5 Hz, 1H), 6.66 (d, J=9.5 Hz, 1H), 5.48 (s, 2H), 3.27-3.34 (m, 4H), 1.86-1.95 (m, 4H);

$^{13}$C NMR (125 MHz, CDCl$_3$) δ 191.2, 161.6, 164.3, 142.1, 139.8 (q, J=1.8 Hz), 137.1, 133.6, 131.7, 131.6, 130.0 (q, J=1.6 Hz), 128.5 (q, J=30.4 Hz), 128.4, 127.9, 126.5 (q, J=5.2 Hz), 124.1 (q, J=273.7 Hz), 120.8, 116.6, 54.4, 48.2, 25.5;

HRMS (ESI-MS) calcd for $C_{24}H_{21}F_3N_2NaO_4S^+$ [M+Na$^+$] 513.1072 found 513.1049.

Production Example 6

Production of 1-(2-(2'-methyl-[1,1'-biphenyl]-4-yl)-2-oxoethyl)-5-(pyrrolidin-1-ylsulfonyl)pyridin-2(1H)-one (Compound TS-12)

Compound TS-12 was produced as a colorless oil with a yield of 32% in a similar manner as described in Production Example 1(2), using compound II and (2-methylphenyl)boronic acid. The following are physicochemical properties of the obtained compound TS-12.

$^1$H NMR (400 MHz, Acetone-d$_6$) δ 8.32 (d, J=2.6 Hz, 1H), 8.19-8.20 (m, 2H), 7.79 (dd, J=9.5, 2.6 Hz, 1H), 7.59-7.60 (m, 2H), 7.20-7.35 (m, 4H), 6.57 (d, J=9.5 Hz, 1H), 5.75 (s, 2H), 3.20-3.30 (m, 4H), 2.28 (s, 3H), 1.80-1.89 (m, 4H);

$^{13}$C NMR (100 MHz, CDCl$_3$) δ 191.1, 161.6, 148.7, 142.2, 140.5, 137.0, 135.3, 132.8, 130.8, 130.1, 129.6, 128.3, 128.2, 126.2, 120.8, 116.5, 54.3, 48.3, 25.6, 20.5;

HRMS (ESI-MS) calcd for $C_{24}H_{24}N_2NaO_4S^+$ [M+Na$^+$] 459.1354 found 459.1367.

Production Example 7

Product-on of 1-(2-(2',6'-dimethyl-[1,1'-biphenyl]-4-yl)-2-oxoethyl)-5-(pyrrolidin-1-ylsulfonyl)pyridin-2(1H)-one (Compound TS-11)

Compound TS-11 was produced as a colorless solid with a yield of 32% in a similar manner as described in Production Example 1(2), using compound II and (2,6-dimethylphenyl)boronic acid. The following are physicochemical properties of the obtained compound TS-11.

$^1$H NMR (500 MHz, CDCl$_3$) δ 8.09 (d, J=8.0 Hz, 2H), 7.94 (d, J=2.5 Hz, 1H), 7.68 (dd, J=9.5, 2.5 Hz, 1H), 7.34 (d, J=8.0 Hz, 2H), 7.18-7.23 (m, 1H), 7.13 (d, J=7.5 Hz, 2H), 6.66 (d, J=9.5 Hz, 1H), 5.49 (s, 2H), 3.26-3.37 (4H, m), 2.02 (6H, s), 1.86-1.96 (4H, m);

$^{13}$C NMR (125 MHz, CDCl$_3$): δ 191.2, 161.6, 148.2, 142.2, 140.4, 137.0, 135.6, 132.9, 130.1, 128.6, 127.9, 127.7, 120.8, 116.5, 54.4, 48.2, 25.5, 20.9;

HRMS (ESI-MS) calcd for $C_{25}H_{26}N_2NaO_4S^+$ [M+Na$^+$] 473.1511 found 473.1501.

Production Example 8

Production of 1-(2-([1,1'-biphenyl]-3-yl)-2-oxoethyl)-5-(pyrrolidin-1-ylsulfonyl)pyridin-2(1H)-one (Compound TS-13)

The method used in Production Example 1 (1) was improved to synthesize a Br regioisomer of compound II using compound I and 2,3'-dibromoacetophenone. Further, the Br regioisomer of compound II was reacted with phenylboronic acid to produce compound TS-13 as a light-yellow oil with a yield of 14%, in a similar manner as described in Production Example 1(2). The following are physicochemical properties of the obtained compound TS-13.

$^1$H NMR (500 MHz, CDCl$_3$) δ 8.21 (t, J=1.7 Hz, $^1$H), 7.96 (ddd, J=7.8, 1.7, 1.1 Hz, 1H), 7.92 (d, J=2.6 Hz, 1H), 7.89 (ddd, J=7.8, 1.7, 1.1 Hz, 1H), 7.68 (dd, J=9.5, 2.6 Hz, 1H), 7.59-7.64 (m, 3H), 7.46-7.52 (m, 2H), 7.39-7.44 (m, 1H), 6.66 (d, J=9.7 Hz, 1H), 5.49 (s, 2H), 3.28-3.33 (m, 4H), 1.89-1.94 (m, 4H);
$^{13}$C NMR (125 MHz, CDCl$_3$) δ 191.8, 161.9, 142.8, 142.4, 140.1, 137.3, 135.2, 133.6, 130.0, 129.5, 128.5, 127.6, 127.3, 127.3, 121.1, 116.8, 54.7, 48.5, 25.8;
HRMS (ESI-MS) calcd for $C_{23}H_{22}N_2NaO_4S^+$ [M+Na$^+$] 445.1198 found 445.1196.

Production Example 9

Production of 1-(2-(2'-methyl-[1,1'-biphenyl]-3-yl)-2-oxoethyl)-5-(pyrrolidin-1-ylsulfonyl)pyridin-2(1H)-one (Compound TS-14)

The method used in Production Example 1 (1) was improved to synthesize a Br regioisomer of compound II using compound I and 2,3'-dibromoacetophenone. Further, the Br regioisomer of Compound II was reacted with (2-methylphenyl)boronic acid to produce compound TS-14 as a light-yellow oil with a yield of 13%, in a similar manner as described in Production Example 1(2). The following are physicochemical properties of the obtained compound TS-14.

$^1$H NMR (500 MHz, CDCl$_3$) δ 7.98-8.02 (m, 1H), 7.94-7.97 (m, 1H), 7.90 (d, J=2.7 Hz, 1H), 7.68 (dd, J=9.6, 2.6 Hz, 1H), 7.62-7.65 (m, 1H), 7.59 (dd, J=7.7, 7.7 Hz, 1H), 7.25-7.32 (m, 3H), 7.23 (d, J=7.2 Hz, 1H), 6.65 (d, J=9.6 Hz, 1H), 5.46 (s, 2H), 3.24-3.34 (m, 4H), 2.27 (s, 3H), 1.88-1.91 (m, 4H);
$^{13}$C NMR (125 MHz, CDCl$_3$) δ 191.4, 161.6, 143.2, 142.1, 140.5, 137.0, 135.4, 134.4, 130.7, 129.8, 129.1, 129.0, 128.2, 126.7, 126.2, 120.8, 116.5, 54.4, 48.3, 25.5, 20.6;
HRMS (ESI-MS) calcd for $C_{24}H_{24}N_2NaO_4S^+$ [M+Na$^+$] 459.1354 found 459.1363.

Production Example 10

Production of 1-(2-(2',6'-dimethyl-[1,1'-biphenyl]-3-yl)-2-oxoethyl)-5-(pyrrolidin-1-ylsulfonyl)pyridin-2(1H)-one (Compound TS-15)

The method used in Production Example 1 (1) was improved to synthesize a Br regioisomer of compound II using compound I and 2,3'-dibromoacetophenone. Further, the Br regioisomer of Compound II was reacted with (2,6-dimethylphenyl)boronic acid to produce compound TS-15 as a light-yellow solid with a yield of 23%, in a similar manner as described in Production Example 1(2). The following are physicochemical properties of the obtained compound TS-15.

$^1$H NMR (500 MHz, CDCl$_3$) δ 8.00 (d, C=7.7 Hz, 1H), 7.89 (d, J=2.6 Hz, 1H), 7.80-7.82 (m, 1H), 7.67 (dd, J=9.5, 2.6 Hz, 1H), 7.62 (dd, J=7.7, 7.7 Hz, 1H), 7.48 (d, J=7.5 Hz, 1H), 7.19-7.23 (m, 1H), 7.14 (d, J=7.5 Hz, 2H), 6.65 (d, J=9.5 Hz, 1H), 5.45 (s, 2H), 3.28-3.34 (m, 4H), 2.03 (s, 6H), 1.87-1.91 (m, 4H);
$^{13}$C NMR (125 MHz, CDCl$_3$) δ 191.3, 161.6, 142.4, 142.1, 140.3, 137.0, 136.0, 135.5, 134.7, 129.5, 128.9, 127.9, 127.7, 126.8, 120.8, 116.5, 54.4, 48.3, 25.5, 21.0;
HRMS (ESI-MS) calcd for $C_{25}H_{26}N_2Na_4S^+$ [M+Na$^+$] 473.1511 found 473.1501.

Production Example 11

Production of 1-(2-oxo-2-(4'-(trifluoromethyl)-[1,1'-biphenyl]-4-yl)ethyl)-5-(pyrrolidin-1-ylsulfonyl)pyridin-2(1H)-one (Compound TS-16)

Compound TS-16 was produced as a light-brown solid with a yield of 71% in a similar manner as described in Production Example 1(2), using compound II and (4-(trifluoromethyl)phenyl)boronic acid. The following are physicochemical properties of the obtained compound TS-16.

$^1$H NMR (400 MHz, CDCl$_3$) δ 8.11 (d, J=0.7 Hz, 1H), 8.09 (s, 1H), 7.95 (d, J=2.5 Hz, 1H), 7.72-7.76 (m, 6H), 7.66 (ddd, J=9.6, 2.5, 0.9 Hz, 1H), 6.63 (d, J=9.6 Hz, 1H), 5.48 (s, 2H), 3.24-3.35 (m, 4H), 1.85-1.94 (m, 4H);
$^{13}$C NMR (100 MHz, CDCl$_3$) δ 191.1, 161.6, 145.6, 143.1, 142.2, 137.0, 133.8, 130.7 (q, J=33.2 Hz), 129.0, 128.0, 127.8, 126.1 (q, J=3.6 Hz), 124.2 (q, J=276.2 Hz), 120.7, 116.5, 54.4, 48.2, 25.5;
HRMS (ESI-MS) calcd for $C_{24}H_{21}F_3Na_2NaO_4S^+$ [M+Na$^+$] 513.1072 found 513.1071.

Production Example 12

Production of 1-(2-(4'-methoxy-[1,1'-biphenyl]-4-yl)-2-oxoethyl)-5-(pyrrolidin-1-ylsulfonyl)pyridin-2(1H)-one (Compound TS-17)

Compound TS-17 was produced as a light-brown solid with a yield of 63% in a similar manner as described in Production Example 1(2), using compound II and (4-methoxyphenyl)boronic acid. The following are physicochemical properties of the obtained compound TS-17.

$^1$H NMR (400 MHz, CDCl$_3$) δ 8.02-8.08 (m, 2H), 7.92 (d, J=2.5 Hz, 1H), 7.69-7.73 (m, 2H), 7.67 (dd, J=9.6, 2.5 Hz, 1H), 7.57-7.63 (m, 2H), 6.96-7.04 (m, 2H), 6.65 (d, J=9.6 Hz, 1H), 5.46 (s, 2H), 3.88 (s, 3H), 3.25-3.35 (m, 4H), 1.82-1.95 (m, 4H);
$^{13}$C NMR (100 MHz, CDCl$_3$) δ 190.9, 161.6, 160.4, 146.9, 142.2, 137.0, 132.4, 131.9, 128.9, 128.6, 127.1, 120.8, 116.4, 114.7, 55.6, 54.2, 48.3, 25.5;
HRMS (ESI-MS) calcd for $C_{24}H_{24}N_2NaO_5S^+$ [M+Na$^+$] 475.1304 found 475.1288.

Production Example 13

Production of 1-(2-oxo-2-(4'-(trifluoromethoxy)-[1,1'-biphenyl]-4-yl)ethyl)-5-(pyrrolidin-1-ylsulfonyl)pyridin-2(1H)-one (Compound TS-18)

Compound TS-18 was produced as a colorless solid with a yield of 35% in a similar manner as described in Production Example 1(2), using compound II and (4-(trifluoromethoxy)phenyl)boronic acid. The following are physicochemical properties of the obtained compound TS-18.

$^1$H NMR (500 MHz, CDCl$_3$) δ 8.08 (d, J=8.0 Hz, 2H), 7.94 (d, J=2.0 Hz, 1H), 7.60-7.75 (m, 5H), 7.34 (d, J=8.0 Hz, 2H), 6.63 (d, J=9.5 Hz, 1H), 5.46 (s, 2H), 3.23-3.37 (m, 4H), 1.84-1.96 (m, 4H);

$^{13}$C NMR (125 MHz, CDCl$_3$) δ 191.3, 161.8, 150.0 (q, J=1.8 Hz), 146.0, 142.5, 138.5, 137.2, 133.7, 129.3, 129.2, 128.0, 121.8, 121.0, 120.8 (q, J=257.7 Hz), 116.7, 54.6, 48.5, 25.8;

HRMS (ESI-MS) calcd for C$_{24}$H$_{21}$F$_3$N$_2$NaO$_5$S$^+$ [M+Na$^+$] 529.1021 found 529.1014.

Production Example 14

Production of 1-(2-(4'-nitro-[1,1'-biphenyl]-4-yl)-2-oxoethyl)-5-(pyrrolidin-1-ylsulfonyl)pyridin-2(1H)-one (Compound TS-19)

Compound TS-19 was produced as a light-brown solid with a yield of 31% in a similar manner as described in Production Example 1(2), using Compound II and (4-nitrophenyl)boronic acid. The following are physicochemical properties of the obtained compound TS-19.

$^1$H NMR (500 MHz, CDCl$_3$) δ 8.36 (d, J=8.6 Hz, 2H), 8.14 (d, J=8.3 Hz, 2H), 7.93 (d, J=2.5 Hz, 1H), 7.75-7.85 (m, 4H), 7.69 (dd, J=9.6, 2.5 Hz, 1H), 6.67 (d, J=9.6 Hz, 1H), 5.46 (s, 2H), 3.24-3.40 (m, 4H), 1.87-2.00 (m, 4H);

$^{13}$C NMR (125 MHz, CDCl$_3$) δ 191.0, 161.6, 148.1, 145.9, 144.7, 142.0, 137.1, 134.4, 129.2, 128.4, 128.2, 124.5, 120.9, 116.8, 54.4, 48.3, 25.6;

HRMS (ESI-ME) calcd for C$_{22}$H$_{21}$N$_3$NaO$_6$S$^+$ [M+Na$^+$] 490.1049 found 490.1035.

Production Example 15

Production of 1-(2-oxo-5-(pyrrolidin-1-ylsulfonyl)pyridin-2(1H)-yl)acetyl-[1,1'-biphenyl]-4-carbonitrile (Compound TS-20)

Compound TS-20 was produced as a light-yellow solid with a yield of 60% in a similar manner as described in Production Example 1(2), using compound II and (4-cyanophenyl)boronic acid. The following are physicochemical properties of the obtained compound TS-20.

$^1$H NMR (500 MHz, CDCl$_3$) δ 8.11-8.16 (m, 2H), 7.93 (d, J=2.6 Hz, 1H), 7.73-7.82 (m, 6H), 7.69 (dd, J=9.7, 2.6 Hz, 1H), 6.66 (d, J=9.7 Hz, 1H), 5.46 (s, 2H), 3.26-3.37 (m, 4H), 1.87-1.97 (m, 4H);

$^{13}$C NMR (125 MHz, CDCl$_3$) δ 191.2, 161.8, 145.4, 144.2, 142.3, 137.3, 134.4, 133.3, 129.4, 128.4, 128.3, 121.1, 118.9, 117.0, 112.7, 54.6, 48.5, 25.8;

HRMS (ESI-MS) calcd for C$_{24}$H$_{21}$N$_3$NaO$_4$S$^+$ [M+Na$^+$] 470.1150 found 470.1145.

Production Example 16

Production of 1-(2-(9,10-dihydrophenanthren-2-yl)-2-oxoethyl)-5-(pyrrolidin-1-ylsulfonyl)pyridin-2(1H)-one (Compound TS-21)

Compound TS-21 was produced as a colorless wax with a yield of 34% in a similar manner as described in Production Example 1(1), using compound I and 2-bromo-1-(9,10-dihydrophenanthren-2-yl)ethanone. The following are physicochemical properties of the obtained compound TS-21.

$^1$H NMR (400 MHz, CDCl$_3$) δ 7.90-7.97 (m, 2H), 7.85-7.89 (m, 2H), 7.78-7.83 (m, 1H), 7.67 (dd, J=9.6, 2.5 Hz, 1H), 7.26-7.39 (m, 3H), 6.64 (d, J=9.6 Hz, 1H), 5.46 (s, 2H), 3.26-3.35 (m, 4H), 2.89-2.99 (m, 4H), 1.87-1.94 (m, 4H);

$^{13}$C NMR (100 MHz, CDCl$_3$) δ 191.0, 161.6, 142.3, 140.8, 138.3, 138.2, 137.0, 133.2, 132.9, 129.2, 128.6, 128.1, 127.4, 127.2, 124.7, 124.3, 120.7, 116.4, 54.2, 48.2, 29.0, 28.8, 25.5;

HRMS (ESI-MS) calcd for C$_{25}$H$_{24}$N$_2$NaO$_4$S$^+$ [M+Na$^+$] 471.1354 found 471.1335.

Production Example 17

Production of 1-(2-([1,1':4',1''-terphenyl]-4-yl)-2-oxoethyl)-5-(pyrrolidin-1-ylsulfonyl)pyridin-2(1H)-one (Compound TS-22)

Compound TS-22 was produced as a colorless wax with a yield of 36% in a similar manner as described in Production Example 1(2), using compound II and [1,1'-biphenyl]-4-yl boronic acid. The following are physicochemical properties of the obtained compound TS-22.

$^1$H NMR (500 MHz, CDCl$_3$) δ 8.09 (d, J=8.3 Hz, 2H), 7.94 (d, J=2.6 Hz, 1H), 7.80 (d, J=8.3 Hz, 2H), 7.73 (s, 4H), 7.60-7.70 (m, 3H), 7.48 (dd, J=7.5, 7.5 Hz, 2H), 7.39 (dd, J=7.5, 7.5 Hz, 1H), 6.65 (d, J=9.8 Hz, 1H), 5.47 (s, 2H), 3.22-3.37 (m, 4H), 1.83-1.95 (m, 4H);

$^{13}$C NMR (125 MHz, CDCl$_3$) δ 191.0, 161.6, 146.7, 142.2, 141.6, 140.4, 138.3, 137.0, 137.0, 133.1, 129.1, 129.0, 127.9, 128.2, 127.6, 127.2, 120.7, 116.4, 54.3, 48.2, 25.5;

HRMS (ESI-MS) calcd for C$_{29}$H$_{26}$N$_2$NaO$_4$S$^+$ [M+Na$^+$] 521.1511 found 521.1502.

Production Example 18

Production of 1-(2-(4'-(dimethylamino)-[1,1'-biphenyl]-4-yl)-2-oxoethyl)-5-(pyrrolidin-1-ylsulfonyl)pyridin-2(1H)-one (Compound TS-23)

Compound TS-23 was produced as a light-yellowish-green solid with a yield of 73% in a similar manner as described in Production Example 1(2), using compound II and (4-(dimethylamino)phenyl)boronic acid. The following are physicochemical properties of the obtained compound TS-23.

$^1$H NMR (500 MHz, CDCl$_3$) δ 8.01 (d, J=8.3 Hz, 2H), 7.92 (d, J=2.3 Hz, 1H), 7.70 (d, J=8.3 Hz, 2H), 7.66 (dd, J=9.5, 2.3 Hz, 1H), 7.58 (d, J=9.0 Hz, 2H), 6.81 (d, J=9.0 Hz, 2H), 6.63 (d, J=9.5 Hz, 1H), 5.44 (s, 2H), 3.25-3.34 (m, 4H), 3.04 (s, 6H), 1.87-1.92 (m, 4H);

$^{13}$C NMR (125 MHz, CDCl$_3$) δ 191.0, 161.9, 151.2, 147.5, 142.6, 137.2, 131.9, 129.2, 128.4, 127.0, 126.5, 120.9, 116.5, 112.9, 54.4, 48.5, 40.7, 25.8;

HRMS (ESI-MS) calcd for C$_{25}$H$_{27}$N$_3$NaO$_4$S$^+$ [M+Na$^+$] 488.1620 found 488.1633.

Production Example 19

Production of 1-(2-(4'-fluoro-[1,1'-biphenyl]-4-yl)-2-oxoethyl)-5-(pyrrolidin-1-ylsulfonyl)pyridin-2(1H)-one (Compound TS-24)

Compound TS-24 was produced as a light-brown solid with a yield of 70% in a similar manner as described in Production Example 1(2), using compound II and (4-fluorophenyl)boronic acid. The following are physicochemical properties of the obtained compound TS-24.

$^1$H NMR (500 MHz, CDCl$_3$) δ 8.08 (d, J=8.5 Hz, 2H), 7.92 (d, J=2.5 Hz, 1H), 7.71 (d, J=8.5 Hz, 2H), 7.68 (dd, J=9.6, 2.5 Hz, 1H), 7.61 (dd, J=8.6, 5.4 Hz, 2H), 7.18 (dd, J=8.6, 8.6 Hz, 2H), 6.65 (d, J==9.5 Hz, 1H), 5.46 (s, 2H), 3.25-3.35 (m, 4H), 1.86-1.96 (m, 4H);

$^{13}$C NMR (125 MHz, CDCl$_3$) δ 191.2, 163.6 (d, J=249.0 Hz), 161.9, 146.6, 142.4, 137.3, 136.0 (d, J=3.0 Hz), 133.3, 129.4 (d, J=8.4 Hz), 129.2, 127.9, 121.0, 116.8, 116.5 (d, J=21.5 Hz), 54.5, 48.5, 25.8;

HRMS (ESI-MS) calcd for C$_{23}$H$_{21}$N$_2$NaO$_4$S$^+$ [M+Na$^+$] 463.1104. found 463.1093.

Production Example 20

Production of 1-(2-(4'-(tertiary butyl)-[1,1'-biphenyl]-4-yl)-2-oxoethyl)-5-(pyrrolidin-1-ylsulfonyl)pyridin-2(1H)-one (Compound TS-25)

Compound TS-25 was produced as a light-brown solid with a yield of 84% in a similar manner as described in Production Example 1(2), using compound II and (4-(tertiary butyl)phenyl)boronic acid. The following are physicochemical properties of the obtained compound TS-25.

$^1$H NMR (400 MHz, CDCl$_3$) δ 8.04-8.09 (m, 2H), 7.92 (d, J=2.7 Hz, 1H), 7.72-7.78 (m, 2H), 7.68 (dd, J=9.5, 2.7 Hz, 1H), 7.57-7.63 (m, 2H), 7.49-7.55 (m, 2H), 6.65 (d, J=9.5 Hz, 1H), 5.47 (s, 2H), 3.26-3.36 (m, 4H), 1.86-1.91 (m, 4H), 1.38 (s, 9H);

$^{13}$C NMR (100 MHz, CDCl$_3$) δ 191.0, 161.6, 152.1, 147.2, 142.2, 137.0, 136.6, 132.8, 128.9, 127.5, 127.1, 126.2, 120.8, 116.4, 54.3, 48.2, 34.8, 31.4, 25.5;

HRMS (ESI-MS) calcd for C$_{27}$H$_{30}$N$_2$NaO$_4$S$^+$ [M+Na$^+$] 501.1824. found 501.1829.

Production Example 21

Production of 1-(2-(4'-methyl-[1,1'-biphenyl]-4-yl)-2-oxoethyl)-5-(pyrrolidin-1-ylsulfonyl)pyridin-2(1H)-one (Compound TS-26)

Compound TS-26 was produced as a light-brown solid with a yield of 88% in a similar manner as described in Production Example 1(2), using compound II and (4-methylphenyl)boronic acid. The following are physicochemical properties of the obtained compound TS-26.

$^1$H NMR (500 MHz, CDCl$_3$) δ 8.06 (d, J=8.3 Hz, 2H), 7.92 (d, J=2.9 Hz, 1H), 7.74 (d, J=8.3 Hz, 2H), 7.67 (dd, J=9.8, 2.9 Hz, 1H), 7.55 (d, J=8.0 Hz, 2H), 7.30 (d, J=8.0 Hz, 2H), 6.65 (d, J=9.8 Hz, 1H), 5.47 (s, 2H), 3.25-3.40 (m, 4H), 2.42 (s, 3H), 1.85-1.95 (m, 4H);

$^{13}$C NMR (125 MHz, CDCl$_3$) δ 191.0, 161.6, 147.3, 142.2, 138.9, 137.0, 136.6, 132.8, 129.9, 128.9, 127.5, 127.3, 120.8, 116.4, 54.3, 48.2, 25.5, 21.4;

HRMS (ESI-ME) calcd for C$_{24}$H$_{24}$N$_2$NaO$_4$S$^+$ [M+Na$^+$] 459.1354. found 459.1346.

Production Example 22

Production of 1-(2-(4-(naphthalen-1-yl)phenyl)-2-oxoethyl)-5-(pyrrolidin-1-ylsulfonyl)pyridin-2(1H)-one (Compound TS-29)

Compound TS-29 was produced as a colorless wax with a yield of 69% in a similar manner as described in Production Example 1(2), using compound II and naphthalen-1-yl boronic acid. The following are physicochemical properties of the obtained compound TS-29.

$^1$H NMR (500 MHz, Acetone-d$_6$) δ 8.34 (d, J=2.6 Hz, 1H), 8.28 (d, J=8.3 Hz, 2H), 8.02 (dd, J=9.8, 9.8 Hz, 2H), 7.86 (d, J=8.3 Hz, 1H), 7.80 (dd, J=9.8, 2.6 Hz, 1H), 7.74 (d, J=8.3 Hz, 2H), 7.51-7.65 (m, 4H), 6.58 (d, J=9.7 Hz, 1H), 5.80 (s, 2H), 3.26-3.34 (m, 4H), 1.86-1.94 (4H, m);

$^{13}$C NMR (125 MHz, Acetone-d$_6$) δ 192.8, 162.0, 147.4, 144.2, 139.8, 138.2, 135.0, 134.9, 132.1, 131.5, 129.5, 129.5, 129.2, 128.0, 127.6, 127.1, 126.5, 126.2, 120.6, 116.4, 55.9, 49.0, 26.0;

HRMS (ESI-MS) calcd for C$_{27}$H$_{24}$N$_2$NaO$_4$S$^+$ [M+Na$^+$] 495.1354. found 495.1339.

Production Example 23

Production of 1-(2-([1,1':4',1''-terphenyl]-3-yl)-2-oxoethyl)-5-(pyrrolidin-1-ylsulfonyl)pyridin-2(1H)-one (Compound TS-30)

The method used in Production Example 1(1) was improved to synthesize a Br regioisomer of compound II using compound I and 2,3'-dibromoacetophenone. Further, the Br regioisomer of compound II was reacted with [1,1'-biphenyl]-4-yl boronic acid to produce compound TS-30 as a colorless solid with a yield of 80%, in a similar manner as described in Production Example 1(2). The following are physicochemical properties of the obtained compound TS-30.

$^1$H NMR (500 MHz, CDCl$_3$) δ 8.26 (s, 1H), 7.99 (d, J=8.0 Hz, 1H), 7.90-7.96 (m, 2H), 7.70-7.73 (m, 4H), 7.60-7.69 (m, 4H), 7.48 (dd, J=7.7 Hz, 2H), 7.38 (dd, J=7.4 Hz, 1H), 6.65 (d, J=9.2 Hz, 1H), 5.51 (s, 2H), 3.26-3.34 (m, 4H), 1.85-1.95 (m, 4H);

$^{13}$C NMR (125 MHz, CDCl$_3$) δ 191.6, 161.6, 142.2, 141.9, 141.1, 140.5, 138.6, 137.0, 135.0, 133.0, 129.7, 129.0, 127.9, 127.7, 127.7, 127.2, 127.1, 126.8, 120.7, 116.4, 54.5, 48.2, 25.5;

HRMS (ESI-MS) calcd for C$_{29}$H$_{26}$N$_2$NaO$_4$S$^+$ [M+Na$^+$] 521.1511. found 521.1537.

Production Example 24

Production of 1-(2-([1,1':4',1'':4'',1'''-quaterphenyl]-3-yl)-2-oxoethyl)-5-(pyrrolidin-1-ylsulfonyl)pyridin-2(1H)-one (Compound TS-31)

The method used in Production Example 1(1) was improved to synthesize a Br regioisomer of compound II using compound I and 2,3'-dibromoacetophenone. Further, the Br regioisomer of compound II was reacted with [1,1':4',1''-terphenyl]-4-yl boronic acid to produce Compound TS-31 as a light-brown solid with a yield of 80%, in a similar manner as described in Production Example 1(2). The following are physicochemical properties of the obtained compound TS-31.

$^1$H NMR (500 MHz, CDCl$_3$) δ 8.28 (dd, J=1.7, 1.7 Hz, 1H), 7.98-8.03 (m, 1H), 7.92-7.97 (m, 2H), 7.63-7.79 (m, 12H), 7.45-7.50 (m, 2H), 7.36-7.40 (m, 1H), 6.67 (d, J=9.5 Hz, 1H), 5.50 (s, 2H), 3.28-3.36 (m, 4H), 1.88-1.96 (m, 4H);

$^{13}$C, NMR (125 MHz, CDCl$_3$) δ 191.3, 161.4, 141.9, 141.7, 140.5, 140.4, 139.1, 138.5, 136.8, 134.8, 132.9, 129.5, 128.8, 127.5, 127.4, 127.3, 127.3, 127.0, 127.0, 126.8, 126.6, 120.6, 116.3, 54.2, 48.0, 25.3;

HRMS (ESI-MS) calcd for C$_{35}$H$_{30}$N$_2$NaO$_4$S$^+$ [M+Na$^+$] 597.1824. found 597.1846.

Production Example 25

Production of 1-(2-([1,1':4',1":4",1"'-quaterphenyl]-4-yl)-2-oxoethyl)-5-(pyrrolidin-1-ylsulfonyl)pyridin-2(1H)-one (Compound TS-32)

Compound TS-32 was produced as a colorless wax with a yield of 33% in a similar manner as described in Production Example 1(2), using compound II and [1,1':4',1"-terphenyl]-4-yl boronic acid. The following are physicochemical properties of the obtained compound TS-32.

$^1$H NMR (500 MHz, CDCl$_3$) δ 8.11 (d, J=8.3 Hz, 2H), 7.93 (d, J=2.3 Hz, 1H), 7.82 (d, J=7.8 Hz, 2H), 7.64-7.80 (m, 11H), 7.45-7.50 (m, 2H), 7.38 (dd, J=7.5, 7.5 Hz, 1H), 6.67 (d, J=9.8 Hz, 1H), 5.48 (s, 2H), 3.30-3.37 (m, 4H), 1.88-1.98 (4H, m);

$^{13}$C NMR (125 MHz, CDCl$_3$) δ 191.0, 161.6, 146.8, 142.2, 141.2, 140.8, 140.7, 139.3, 138.4, 137.0, 133.1, 129.0, 129.0, 127.9, 127.8, 127.7, 127.6, 127.2, 120.8, 116.5, 54.3, 48.3, 25.6.

Production Example 26

Production of 1-(2-([1,1':3',1"-terphenyl]-4-yl)-2-oxoethyl)-5-(pyrrolidin-1-ylsulfonyl)pyridin-2(1H)-one (Compound TS-34)

Compound TS-34 was produced as a colorless wax with a yield of 95% in a similar manner as described in Production Example 1(2), using compound II and [1,1'-biphenyl]-3-yl boronic acid. The following are physicochemical properties of the obtained compound TS-34.

$^1$H NMR (500 MHz, CDCl$_3$) δ 8.10 (d, J=8.6 Hz, 2H), 7.94 (d, J=2.6 Hz, 1H), 7.83-7.85 (m, 1H), 7.80 (d, J=8.3 Hz, 2H), 7.60-7.70 (m, 5H), 7.56 (dd, J=7.7, 7.7 Hz, 1H), 7.54-7.59 (m, 2H), 7.37-7.42 (m, 2H), 6.65 (d, J=9.8 Hz, 1H), 5.49 (s, 2H), 3.28-3.34 (m, 4H), 1.86-1.94 (m, 4H);

$^{13}$C NMR (125 MHz, CDCl$_3$) δ 191.1, 161.6, 147.2, 142.3, 142.2, 140.9, 140.1, 137.0, 133.2, 129.6, 129.0, 128.9, 127.9, 127.8, 127.6, 127.4, 126.4, 126.3, 120.7, 116.4, 54.3, 48.2, 25.5;

HRMS (ESI-MS) calcd for C$_{29}$H$_{26}$N$_2$NaO$_4$S$^+$ [M+Na$^+$] 521.1511. found 521.1499.

Production Example 27

Production of 1-(2-([1,1':3',1"-terphenyl]-3-yl)-2-oxoethyl)-5-(pyrrolidin-1-ylsulfonyl)pyridin-2(1H)-one (Compound TS-35)

The method used in Production Example 1(1) was improved to synthesize a Br regioisomer of compound II using compound I and 2,3'-dibromoacetophenone. Further, the Br regioisomer of compound II was reacted with [1,1'-biphenyl]-3-yl boronic acid to produce compound TS-35 as a light-yellow oil with a yield of 97%, in a similar manner as described in Production Example 1(2). The following are physicochemical properties of the obtained compound TS-35.

$^1$H NMR (500 MHz, CDCl$_3$) δ 8.26 (s, 1H), 8.00 (d, J=7.7 Hz, 1H), 7.90-7.97 (m, 2H), 7.82 (s, 1H), 7.52-7.74 (m, 7H), 7.48 (dd, J=7.6, 7.6 Hz, 2H), 7.37 (d, J=7.3 Hz, 1H), 6.65 (d, J=9.5 Hz, 1H), 5.50 (s, 2H), 3.22-3.36 (m, 4H), 1.84-1.95 (m, 4H);

$^{13}$C NMR (125 MHz, CDCl$_3$) δ 191.5, 161.6, 142.4, 142.3, 142.2, 140.9, 140.4, 137.0, 135.0, 133.3, 129.7, 129.6, 129.0, 127.8, 127.4, 127.2, 127.1, 127.0, 126.3, 126.3, 120.8, 116.4, 54.5, 48.2, 25.5;

HRMS (ESI-MS) calcd for C$_{29}$H$_{26}$N$_2$NaO$_4$S$^+$ [M+Na$^+$] 521.1511. found 521.1507.

Production Example 28

Production of 1-(2-oxo-2-(5'-phenyl-[1,1':3',1"-terphenyl]-4-yl)ethyl)-5-(pyrrolidin-1-ylsulfonyl)pyridin-2(1H)-one (Compound TS-36)

Compound TS-36 was produced as a light-yellow wax with a yield of 80% in a similar manner as described in Production Example 1 (2), using compound II and [1,1':3',1"-terphenyl]-5'-yl boronic acid. The following are physicochemical properties of the obtained compound TS-36.

$^1$H NMR (500 MHz, CDCl$_3$) δ 8.12 (d, J=8.3 Hz, 2H), 7.94 (d, J=2.3 Hz, 1H), 7.84-7.90 (m, 3H), 7.82 (s, 2H), 7.65-7.74 (m, 5H), 7.50 (dd, J=7.5, 7.5 Hz, 4H), 7.42 (dd, J=7.5, 7.5 Hz, 2H), 6.66 (d, J=9.5 Hz, 1H), 5.48 (s, 2H), 3.26-3.37 (m, 4H), 1.86-1.96 (m, 4H);

$^{13}$C NMR (125 MHz, CDCl$_3$) δ 191.1, 161.6, 147.3, 142.9, 142.2, 140.9, 140.7, 137.0, 133.3, 129.1, 129.0, 128.0, 128.0, 127.5, 126.6, 125.3, 120.8, 116.5, 54.3, 48.2, 25.5;

HRMS (ESI-MS) calcd for C$_{35}$H$_{30}$N$_2$NaO$_4$S$^+$ [M+Na$^+$] 597.1824. found 597.1846.

Production Example 29

Production of 1-(2-oxo-2-(5'-phenyl-[1,1':3',1"-terphenyl]-3-yl)ethyl)-5-(pyrrolidin-1-ylsulfonyl)pyridin-2(1H)-one (Compound TS-37)

The method used in Production Example 1(1) was improved to synthesize a Br regioisomer of compound II using compound I and 2,3'-dibromoacetophenone. Further, the Br regioisomer of compound II was reacted with [1,1':3',1"-terphenyl]-5'-yl boronic acid to produce compound TS-37 as a light-yellow oil with a yield of 95%, in a similar manner as described in Production Example 1(2). The following are physicochemical properties of the obtained compound TS-37.

$^1$H NMR (500 MHz, CDCl$_3$) δ 8.31 (s, 1H), 8.02 (d, J=7.7 Hz, 1H), 7.99 (d, J=7.7 Hz, 1H), 7.94 (d, J=2.3 Hz, 1H), 7.83-7.86 (m, 1H), 7.78-7.81 (m, 2H), 7.69-7.75 (m, 4H), 7.62-7.69 (m, 2H), 7.50 (dd, J=7.5, 7.5 Hz, 4H), 7.41 (dd, J=7.5, 7.5 Hz, 2H), 6.65 (d, J=9.7 Hz, 1H), 5.51 (s, 2H), 3.24-3.36 (m, 4H), 1.85-1.96 (m, 4H);

$^{13}$C NMR (125 MHz, CDCl$_3$) δ 191.5, 161.6, 142.8, 142.4, 142.2, 141.0, 140.9, 137.0, 135.0, 133.4, 129.7, 129.1, 127.9, 127.5, 127.3, 127.1, 126.1, 125.2, 120.8, 116.5, 54.5, 48.2, 25.5;

HRMS (ESI-MS) calcd for C$_{35}$H$_{30}$N$_2$NaO$_4$S$^+$ [M+Na$^+$] 597.1824 found 597.1846.

Production Example 30

Production of 1-(2-(4'-(naphthalen-2-yl)-[1,1'-biphenyl]-4-yl)-2-oxoethyl)-5-(pyrrolidin-1-ylsulfonyl)pyridin-2(1H)-one (Compound TS-38)

Compound TS-38 was produced as a light-brown solid with a yield of 83% in a similar manner as described in Production Example 1(2), using compound II and (4-(naphthalen-2-yl)phenyl)boronic acid. The following are physicochemical properties of the obtained compound TS-38.

$^1$H NMR (500 MHz, Acetone-d$_6$) δ 8.31 (d, J=2.6 Hz, 1H), 8.28 (s, 1H), 8.20-8.24 (m, 2H), 7.90-8.06 (m, 10H), 7.79 (dd, J=9.7, 2.6 Hz, 1H), 7.50-7.58 (m, 2H), 6.57 (d, J=9.7 Hz, 1H), 5.75 (s, 2H), 3.22-3.30 (m, 4H), 1.80-1.90 (m, 4H);
$^{13}$C NMR (125 MHz, Acetone-d$_6$) δ 192.6, 162.1, 146.7, 144.2, 141.9, 139.4, 138.5, 138.1, 134.9, 134.8, 134.0, 129.8, 129.7, 129.3, 128.8, 128.8, 128.6, 128.2, 127.5, 127.2, 126.6, 126.1, 120.7, 116.5, 55.8, 49.0, 26.1;
HRMS (ESI-MS) calcd for C$_{33}$H$_{28}$N$_2$NaO$_4$S$^+$ [M+Na$^+$] 571.1667. found 571.1645.

Production Example 31

Production of 1-(2-(4'-(naphthalen-1-yl)-[1,1'-biphenyl]-4-yl)-2-oxoethyl)-5-(pyrrolidin-1-ylsulfonyl)pyridin-2(1H)-one (Compound TS-39)

Compound TS-39 was produced as a colorless solid with a yield of 84% in a similar manner as described in Production Example 1(2), using compound II and (4-(naphthalen-1-yl)phenyl)boronic acid. The following are physicochemical properties of the obtained compound TS-39.
$^1$H NMR (500 MHz, CDCl$_3$) δ 8.10-8.16 (m, 2H), 7.84-7.98 (m, 6H), 7.76-7.81 (m, 2H), 7.69 (dd, J=9.7, 2.6 Hz, 1H), 7.62-7.66 (m, 2H), 7.44-7.58 (m, 4H), 6.66 (d, J=9.7 Hz, 1H), 5.49 (s, 2H), 5.46 (s, 2H), 3.25-3.35 (m, 4H), 1.85-2.00 (m, 4H);
$^{13}$C NMR (125 MHz, CDCl$_3$) δ 191.3, 191.3, 161.9, 147.2, 142.5, 142.4, 141.6, 139.8, 138.7, 137.3, 134.3, 133.4, 131.9, 131.2, 129.3, 128.8, 128.4, 128.0, 127.6, 127.4, 126.6, 126.3, 126.2, 125.8, 121.0, 116.6, 54.6, 48.5, 25.6;
HRMS (ESI-MS) calcd for C$_{33}$H$_{28}$N$_2$NaO$_4$S$^+$ [M+Na$^+$] 571.1667. found 571.1645.

Production Example 32

Production of 1-(2-(4'-benzyl-[1,1'-biphenyl]-4-yl)-2-oxoethyl)-5-(pyrrolidin-1-ylsulfonyl)pyridin-2(1H)-one (Compound TS-40)

Compound TS-40 was produced as a colorless solid with a yield of 61% in a similar manner as described in Production Example 1(2), using compound II and (4-benzylphenyl)boronic acid. The following are physicochemical properties of the obtained compound TS-40.
$^1$H NMR (500 MHz, CDCl$_3$) δ 8.04-8.08 (m, 2H), 7.92 (d, J=2.5 Hz, 1H), 7.71-7.75 (m, 2H), 7.67 (dd, J=9.7, 2.5 Hz, 1H), 7.55-7.59 (m, 2H), 7.28-7.34 (m, 4H), 7.18-7.25 (m, 3H), 6.65 (d, J=9.7 Hz, 1H), 5.45 (s, 2H), 4.05 (s, 2H), 3.25-3.35 (m, 4H), 1.85-1.91 (m, 4H);
$^{13}$C NMR (125 MHz, CDCl$_3$) δ 191.0, 161.6, 147.1, 142.2, 142.1, 140.8, 137.4, 137.0, 132.9, 129.8, 129.1, 128.9, 128.7, 127.6, 127.5, 126.4, 120.8, 116.5, 54.3, 48.2, 41.8, 25.5;
HRMS (ESI-MS) calcd for C$_{33}$H$_{28}$N$_2$NaO$_4$S$^+$ [M+Na$^+$] 535.1667. found 535.1656.

Production Example 33

Production of 1-(2-(4'-(naphthalen-1-yl)-[1,1'-biphenyl]-3-yl)-2-oxoethyl)-5-(pyrrolidin-1-ylsulfonyl)pyridin-2(1H)-one (Compound TS-41)

The method used in Production Example 1(1) was improved to synthesize a Br regioisomer of compound II using compound I and 2,3'-dibromoacetophenone. Further, the Br regioisomer of compound II was reacted with (4-(naphthalen-1-yl)phenyl)boronic acid to produce compound TS-41 as a colorless wax with a yield of 95%, in a similar manner as described in Production Example 1(2). The following are physicochemical properties of the obtained compound TS-41.
$^1$H NMR (500 MHz, CDCl$_3$) δ 8.31-8.33 (s, 1H), 7.88-8.02 (m, 6H), 7.74-7.78 (m, 2H), 7.62-7.71 (m, 4H), 7.45-7.58 (m, 4H), 6.67 (d, J=9.8 Hz, 1H), 5.52 (s, 2H), 3.30-3.36 (m, 4H), 1.88-1.96 (m, 4H);
$^{13}$C NMR (125 MHz, CDCl$_3$) δ 191.3, 161.4, 141.9, 141.9, 140.6, 139.4, 138.5, 136.8, 134.8, 133.8, 133.0, 131.4, 130.7, 129.5, 128.3, 127.8, 127.0, 127.0, 126.9, 126.7, 126.1, 125.8, 125.8, 125.3, 120.6, 116.4, 54.2, 48.0, 25.3;
HRMS (ESI-MS) calcd for C$_{30}$H$_{28}$N$_2$NaO$_4$S$^+$ [M+Na$^+$] 535.1667. found 535.1645.

Production Example 34

Production of 1-(2-(4'-(naphthalen-2-yl)-[1,1'-biphenyl]-3-yl)-2-oxoethyl)-5-(pyrrolidin-1-ylsulfonyl)pyridin-2(1H)-one (Compound TS-42)

The method used in Production Example 1(1) was improved to synthesize a Br regioisomer of compound II using compound I and 2,3'-dibromoacetophenone. Further, the Br regioisomer of compound II was reacted with (4-(naphthalen-2-yl)phenyl)boronic acid to produce compound TS-42 as a light-brown wax with a yield of 86%, in a similar manner as described in Production Example 1(2). The following are physicochemical properties of the obtained compound TS-42.
$^1$H NMR (500 MHz, CDCl$_3$) δ 8.28 (dd, J=1.7 Hz, 1H), 8.11 (s, 1H), 8.00 (d, J=7.8 Hz, 1H), 7.82-7.98 (m, 7H), 7.80 (dd, J=8.3, 1.9 Hz, 1H), 7.75 (d, J=8.3 Hz, 2H), 7.68 (dd, J=9.8, 2.6 Hz, 1H), 7.64 (dd, J=7.8, 7.8 Hz, 1H), 7.48-7.56 (m, 2H), 6.66 (d, J=9.8 Hz, 1H), 5.50 (s, 2H), 3.27-3.36 (m, 4H), 1.85-1.95 (m, 4H);
$^{13}$C NMR (125 MHz, CDCl$_3$) δ 191.6, 161.6, 142.2, 142.0, 141.0, 138.7, 137.8, 137.0, 135.0, 133.8, 133.1, 132.9, 129.8, 128.7, 128.4, 128.1, 127.8, 127.8, 127.1, 126.8, 126.6, 126.3, 126.0, 125.5, 120.8, 116.6, 54.5, 48.2, 25.5;
HRMS (ESI-MS) calcd for C$_{33}$H$_{28}$N$_2$NaO$_4$S$^+$ [M+Na$^+$] 571.1667. found 571.1645.

Production Example 35

Production of 1-(2-(4'-benzyl-[1,1'-biphenyl]-3-yl)-2-oxoethyl)-5-(pyrrolidin-1-ylsulfonyl)pyridin-2(1H)-one (Compound TS-43)

The method used in Production Example 1(1) was improved to synthesize a Br regioisomer of compound II using compound I and 2,3'-dibromoacetophenone. Further, the Br regioisomer of compound II was reacted with (4-benzylphenyl)boronic acid to produce Compound TS-43 as a light-brown solid with a yield of 37%, in a similar manner as described in Production Example 1(2). The following are physicochemical properties of the obtained compound TS-43.
$^1$H NMR (500 MHz, CDCl$_3$) δ 8.33 (dd, J=1.7, 1.7 Hz, 1H), 8.29 (d, J=2.9 Hz, 1H), 8.06 (ddd, J=7.3, 1.7, 1.2 Hz, 1H), 7.97 (ddd, J=8.6, 1.7, 1.2 Hz, 1H), 7.77 (dd, J=9.7, 2.9, 1H), 7.64-7.69 (m, 3H), 7.38 (d, J=8.3 Hz, 2H), 7.27-7.33

(m, 4H), 7.18-7.23 (m, 1H), 6.56 (d, J=9.7 Hz, 1H), 5.77 (s, 2H), 4.05 (s, 2H), 3.22-3.28 (m, 4H), 1.81-1.88 (m, 4H);

$^{13}$C NMR (125 MHz, CDCl$_3$) δ 191.6, 161.6, 142.3, 142.2, 141.4, 140.9, 137.6, 137.0, 134.9, 133.1, 129.8, 129.6, 129.1, 128.7, 127.4, 126.8, 126.8, 126.4, 120.8, 116.5, 54.4, 48.2, 41.7, 25.5;

HRMS (ESI-MS) calcd for C$_{30}$H$_{28}$N$_2$NaO$_4$S$^+$ [M+Na$^+$] 535.1667. found 535.1668.

Production Example 36

Production of 1-(2-(2'-methoxy-[1,1'-biphenyl]-4-yl)-2-oxoethyl)-5-(pyrrolidin-1-ylsulfonyl)pyridin-2 (1H)-one (Compound TS-46)

Compound TS-46 was produced as a light-yellow oil with a yield of 94%, in a similar manner as described in Production Example 1(2), using compound II and (2-methoxyphenyl)boronic acid. The following are physicochemical properties of the obtained compound TS-46.

$^1$H NMR (500 MHz, CDCl$_3$) δ 8.04 (d, J=8.6 Hz, 2H), 7.92 (d, J=2.6 Hz, 1H), 7.60-7.75 (m, 3H), 7.30-7.40 (m, 2H), 7.03-7.09 (m, 1H), 7.02 (d, J=8.4 Hz, 1H), 6.64 (d, J=9.5 Hz, 1H), 5.46 (s, 2H), 3.84 (s, 3H), 3.25-3.35 (m, 4H), 1.85-1.93 (m, 4H);

$^{13}$C NMR (125 MHz, CDCl$_3$) δ 191.2, 161.6, 156.6, 145.3, 142.2, 137.0, 132.7, 130.8, 130.3, 130.0, 129.2, 128.0, 121.2, 120.7, 116.4, 111.6, 55.7, 54.3, 48.2, 25.5;

HRMS (ESI-MS) calcd for C$_{24}$H$_{24}$N$_2$NaO$_5$S$^+$ [M+Na$^+$] 475.1304 found 475.1281.

Production Example 37

Production of 1-(2-(3'-methoxy-[1,1'-biphenyl]-4-yl)-2-oxoethyl)-5-(pyrrolidin-1-ylsulfonyl)pyridin-2 (1H)-one (Compound TS-47)

Compound TS-47 was produced as a colorless wax with a yield of 79%, in a similar manner as described in Production Example 1(2), using compound II and (3-methoxyphenyl)boronic acid. The following are physicochemical properties of the obtained compound TS-47.

$^1$H NMR (500 MHz, CDCl$_3$) δ 8.05-8.08 (m, 2H), 7.93 (d, J=2.1 Hz, 1H), 7.73-7.90 (m, 2H), 7.67 (dd, J=9.6, 2.7 Hz, 1H), 7.41 (dd. J=7.8, 7.8 Hz, 1H), 7.23 (ddd, J=7.9, 2.1, 0.8 Hz, 1H), 7.16 (dd, J=2.1 Hz, 1H), 6.97 (ddd, J=7.9, 2.1, 0.8 Hz, 1H), 6.65 (d, J=9.6 Hz, 1H), 5.46 (s, 2H), 3.89 (s, 3H), 3.26-3.34 (m, 4H), 1.88-1.94 (m, 4H);

$^{13}$C NMR (125 MHz, CDCl$_3$) δ 191.1, 161.4, 160.0, 147.0, 141.9, 140.8, 136.7, 132.9, 130.0, 128.6, 127.6, 120.5, 119.7, 116.2, 113.8, 113.0, 55.3, 54.1, 48.0, 25.3;

HRMS (ESI-MS) calcd for C$_{24}$H$_{24}$N$_2$NaO$_5$S$^+$ [M+Na$^+$] 475.1304 found 475.1282.

Production Example 38

Production of 1-(2-(2'-fluoro-[1,1'-biphenyl]-4-yl)-2-oxoethyl)-5-(pyrrolidin-1-ylsulfonyl)pyridin-2 (1H)-one (Compound TS-48)

Compound TS-48 was produced as a colorless wax with a yield of 27%, in a similar manner as described in Production Example 1(2), using compound II and (2-fluorophenyl)boronic acid. The following are physicochemical properties of the obtained compound TS-48.

$^1$H NMR (500 MHz, CDCl$_3$) δ 8.06-8.11 (m 2H), 7.93 (d, J=2.7 Hz, 1H), 7.70-7.75 (m, 2H), 7.68 (dd, J=9.6, 2.6 Hz, 1H), 7.48 (ddd, J=7.8, 7.8, 1.7 Hz, 1H), 7.36-7.43 (m, 1H), 7.25-7.28 (m, 1H), 7.17-7.23 (m, 1H), 6.65 (d, J=9.6 Hz, 1H), 5.47 (s, 2H), 3.25-3.35 (m, 4H), 1.85-1.95 (m, 4H);

$^{13}$C NMR (125 MHz, CDCl$_3$) δ 191.4, 161.9, 160.2 (d, J=248.9 Hz), 142.5 (d, J=1.1 Hz), 142.4, 137.3, 133.6, 131.0 (d, J=3.0 Hz), 130.7 (d, J=8.3 Hz), 130.0 (d, J=3.5 Hz), 128.7, 127.9 (d, J=13.2 Hz), 125.1 (d, J=3.6 Hz), 121.0, 116.8 (d, J=22.1 Hz), 116.7, 54.6, 48.5, 25.8.

Production Example 39

Production of 1-(2-(3'-fluoro-[1,1'-biphenyl]-4-yl)-2-oxoethyl)-5-(pyrrolidin-1-ylsulfonyl)pyridin-2 (1H)-one (Compound TS-49)

Compound TS-49 was produced as a light-brown solid with a yield of 97% in a similar manner as described in Production Example 1(2), using compound II and (3-fluorophenyl)boronic acid. The following are physicochemical properties of the obtained compound TS-49.

$^1$H NMR (400 MHz, CDCl$_3$) δ 8.09 (d, J=8.3 Hz, 2H), 7.93 (d, J=2.7 Hz, 1H), 7.74 (d, J=8.3 Hz, 2H), 7.68 (dd, J=9.6, 2.7 Hz, 1H), 7.40-7.50 (m, 2H), 7.30-7.40 (m, 1H), 7.10-7.15 (m, 1H), 6.66 (d, J=9.6 Hz, 1H), 5.46 (s, 2H), 3.25-3.35 (m, 4H), 1.85-1.95 (m, 4H);

$^{13}$C NMR (100 MHz, CDCl$_3$) δ 191.3, 164.6 (d, J=246.5 Hz), 161.9, 146.2, 142.4, 142.1 (d, J=7.8 Hz), 137.3, 133.8, 131.0 (d, J=8.4 Hz), 129.3, 128.1, 123.4 (d, J=3.0 Hz), 121.0, 116.8, 115.9 (d, J=21.0 Hz), 114.7 (d, J=22.1 Hz), 54.6, 48.5, 25.8;

HRMS (ESI-MS) calcd for C$_{23}$H$_{21}$FN$_2$NaO$_4$S$^+$ [M+Na$^+$] 463.1104 found 475.1096.

Production Example 40

Production of 1-(2-(2'-chloro-[1,1'-biphenyl]-4-yl)-2-oxoethyl)-5-(pyrrolidin-1-ylsulfonyl)pyridin-2 (1H)-one (Compound TS-50)

Compound TS-50 was produced as a light-brown wax with a yield of 75% in a similar manner as described in Production Example 1(2), using compound II and (2-chlorophenyl)boronic acid. The following are physicochemical properties of the obtained compound TS-50.

$^1$H NMR (500 MHz, CDCl$_3$) δ 8.05-8.10 (m, 2H), 7.93 (d, J=2.6 Hz, 1H), 7.68 (dd, J=9.7, 2.6 Hz, 1H), 7.59-7.62 (m, 2H), 7.48-7.53 (m, 1H), 7.32-7.38 (m, 3H), 6.65 (d, J=9.7 Hz, 1H), 5.48 (s, 2H), 3.29-3.34 (m, 4H), 1.86-1.94 (m, 4H);

$^{13}$C NMR (125 MHz, CDCl$_3$) δ 191.2, 161.6, 145.7, 142.1, 139.2, 137.0, 133.4, 132.4, 131.2, 130.4, 130.4, 129.6, 128.2, 127.2, 1280.8, 116.6, 54.4, 48.3, 25.5;

HRMS (ESI-MS) calcd for C$_{23}$H$_{21}$ClN$_2$NaO$_4$S$^+$ [M+Na$^+$] 479.0808. found 479.0788.

Production Example 41

Production of 1-(2-(4'-chloro-[1,1'-biphenyl]-4-yl)-2-oxoethyl)-6-oxo-1,6-dihydropyridine-3-sulfonamide (Compound TS-52)

Compound TS-52 was produced as a light-yellow wax with a yield of 12% in a similar manner as described in Production Example 1, by using N,N-bis(4-methoxybenzyl)-6-oxo-1,6-dihydropyridine-3-sulfonamide in (1) in place of compound I, and using (4-chlorophenyl)boronic acid in (2) in place of [3-(trifluoromethyl)phenyl]boronic acid to obtain 4-methoxybenzyl protected product of TS-52, followed by post-treatment with trifluoroacetic acid. The following are physicochemical properties of the obtained compound TS-52.

$^1$H NMR (500 MHz, Acetone-$d_6$) δ 8.24 (d, J=2.6 Hz, 1H), 8.21 (d, J=8.3 Hz, 2H), 7.90 (d, J=8.3 Hz, 2H), 7.79-7.81 (m, 3H), 7.56 (d, J=8.6 Hz, 2H), 6.56 (d, J=9.5 Hz, 1H), 5.69 (s, 2H);

$^{13}$C NMR (125 MHz, Acetone-$d_6$) δ 192.5, 161.9, 145.7, 141.9, 139.2, 137.5, 135.0, 134.9, 130.0, 129.8, 129.7, 128.2, 123.1, 120.7, 55.9;

HRMS (ESI-MS) calcd for $C_{19}H_{15}ClN_2NaO_4S^+$ [M+Na$^+$] 425.0339. found 425.0321.

Production Example 42

Production of 1-(2-(4'-chloro-2'-(trifluoromethyl)-[1,1'-biphenyl]-4-yl)-2-oxoethyl)-5-(pyrrolidin-1-ylsulfonyl)pyridin-2(1H)-one (Compound TS-53)

Compound TS-53 was produced as a light-yellow solid with a yield of 81% in a similar manner as described in Production Example 1(2), using compound II and (4-chloro-2-(trifluoromethyl)phenyl)boronic acid. The following are physicochemical properties of the obtained compound TS-53.

$^1$H NMR (500 MHz, CDCl$_3$) δ 8.05 (d, J=8.0 Hz, 2H), 7.93 (d, J=2.5 Hz, 1H), 7.77 (s, 1H), 7.67 (dd, J=9.6, 2.5 Hz, 1H), 7.55-7.60 (m, 1H), 7.47 (d, J=8.0 Hz, 2H), 7.26-7.29 (m, 1H), 6.64 (d, J=9.6 Hz, 1H), 5.47 (s, 2H), 3.26-3.31 (m, 4H), 1.82-1.94 (m, 4H);

$^{13}$C NMR (100 MHz, CDCl$_3$) δ 191.1, 161.6, 144.9, 142.1, 138.3 (q, J=2.0 Hz), 137.1, 134.7, 133.9, 133.0, 131.8, 130.0 (q, J=31.0 Hz), 129.9 (q, J=1.6 Hz), 128.0, 126.8 (q, J=5.5 Hz), 123.2 (q, J=274.4 Hz), 120.8, 116.6, 54.4, 48.2, 25.5;

HRMS (ESI-MS) calcd for $C_{24}H_{20}ClF_3N_2NaO_4S^+$ [M+Na$^+$] 547.0682. found 547.0661.

Production Example 43

Production of 1-(2-(4'-chloro-3'-(trifluoromethyl)-[1,1'-biphenyl]-4-yl)-2-oxoethyl)-5-(pyrrolidin-1-ylsulfonyl)pyridin-2(1H)-one (Compound TS-54)

Compound TS-54 was produced as a light-yellow solid with a yield of 88% in a similar manner as described in Production Example 1 (2), using compound II and (4-chloro-3-(trifluoromethyl)phenyl)boronic acid. The following are physicochemical properties of the obtained compound TS-54.

$^1$H NMR (500 MHz, CDCl$_3$) δ 8.11 (d, J=8.3 Hz, 2H), 7.92-7.95 (m, 2H), 7.70-7.75 (m, 3H), 7.67 (dd, J=9.8, 2.6 Hz, 1H), 7.63 (d, J=8.3 Hz, 1H), 6.64 (d, J=9.8 Hz, 1H), 5.47 (s, 2H), 3.24-3.32 (m, 4H), 1.81-1.91 (m, 4H);

$^{13}$C NMR (125 MHz, CDCl$_3$) δ 191.0, 161.6, 144.5, 142.1, 138.5, 137.0, 133.9, 132.8 (g, J=1.6 Hz), 132.4, 131.5, 129.3 (q, J=31.6 Hz), 129.2, 127.8, 126.5 (q, J=5.4 Hz), 122.8 (q, J=273.1 Hz), 120.8, 116.6, 54.4, 48.2, 25.5;

HRMS (ESI-MS) calcd for $C_{24}H_{20}ClF_3N_2NaO_4S^+$ [M+Na$^+$] 547.0682. found 547.0673.

Production Example 44

Production of 1-(2-(4'-chloro-[1,1'-biphenyl]-4-yl)-2-oxoethyl)-6-oxo-N-propyl-1,6-dihydropyridine-3-sulfonamide (Compound TS-56)

Compound TS-56 was produced as a colorless solid with a yield of 12% in a similar manner as described in Production Example 1, using 6-oxo-N-propyl-1,6-dihydropyridine-3-sulfonamide in place of compound I. The following are physicochemical properties of the obtained compound TS-56.

$^1$H NMR (500 MHz, CDCl$_3$) δ 8.08 (d, J=8.0 Hz, 2H), 7.95 (d, J=2.8 Hz, 1H), 7.72 (d, J=8.0 Hz, 2H), 7.66 (dd, J=9.6, 2.8 Hz, 1H), 7.58 (d, J=8.5 Hz, 2H), 7.47 (d, J=8.5 Hz, 2H), 6.67 (d, J=9.6 Hz, 1H), 5.43 (s, 2H), 4.44 (brs, 1H), 3.03 (dt, J=6.9, 6.7 Hz, 2H), 1.55-1.61 (m, 2H), 0.95 (t, J=7.5 Hz, 3H);

$^{13}$C NMR (125 MHz, CDCl$_3$) δ 190.9, 161.6, 146.0, 142.0, 138.0, 136.6, 135.0, 133.3, 129.4, 129.0, 128.7, 127.6, 121.1, 119.0, 54.6, 45.1, 23.1, 11.3;

HRMS (ESI-MS) calcd for $C_{22}H_{21}ClN_2NaO_4S^+$ [M+Na$^+$] 467.0808. found 467.0810.

Production Example 45

Production of 1-(2-(3',5'-bis(trifluoromethyl)-[1,1'-biphenyl]-4-yl)-2-oxoethyl)-5-(pyrrolidin-1-ylsulfonyl)pyridin-2(1H)-one (Compound TS-57)

Compound TS-57 was produced as a light-yellow solid with a yield of 94% in a similar manner as described in Production Example 1(2), using compound II and (3,5-bis(trifluoromethyl)phenyl)boronic acid. The following are physicochemical properties of the obtained compound TS-57.

$^1$H NMR (500 MHz, CDCl$_3$) δ 8.14 (d, J=8.3 Hz, 2H), 8.06 (s, 2H), 7.97 (d, J=2.5 Hz, 1H), 7.93 (s, 1H), 7.76 (d, J=8.3 Hz, 2H), 7.66 (dd, J=9.7, 2.5 Hz, 1H), 6.63 (d, J=9.7 Hz, 1H), 5.49 (s, 2H), 3.20-3.33 (m, 4H), 1.82-1.93 (m, 4H);

$^{13}$C NMR (125 MHz, CDCl$_3$) δ 191.0, 161.6, 143.9, 142.2, 141.8, 137.0, 134.4, 132.7 (q, J=33.4 Hz), 129.3, 128.0, 127.5, 123.3 (q, J=272.7 Hz), 122.2, 120.7, 116.6, 54.5, 48.2, 25.5;

HRMS (ESI-MS) calcd for $C_{25}H_{20}F_6N_2NaO_4S^+$ [M+Na$^+$] 581.0946. found 581.0942.

Production Example 46

Production of 1-(2-(4'-chloro-2'-methyl-[1,1'-biphenyl]-4-yl)-2-oxoethyl)-5-(pyrrolidin-1-ylsulfonyl)pyridin-2(1H)-one (Compound TS-58)

Compound IS-58 was produced as a brown solid with a yield of 76% in a similar manner as described in Production Example 1(2), using compound II and (4-chloro-2-methylphenyl)boronic acid. The following are physicochemical properties of the obtained compound TS-58.

$^1$H NMR (500 MHz, CDCl$_3$) δ 8.06 (d, J=8.3 Hz, 2H), 7.94 (d, J=2.6 Hz, 1H), 7.67 (dd, J=9.8, 2.6 Hz, 1H), 7.45 (d, J=8.3 Hz, 2H), 7.20-7.31 (m, 2H), 7.16 (d, J=8.0 Hz, 1H), 6.64 (d, J=9.6 Hz, 1H), 5.47 (s, 2H), 3.25-3.35 (m, 4H), 2.25 (s, 3H), 1.80-1.95 (m, 4H);

$^{13}$C NMR (125 MHz, CDCl$_3$) δ 191.1, 161.6, 147.3, 142.2, 138.9, 137.2, 137.0, 134.0, 133.1, 130.8, 130.6, 130.0, 128.3, 126.3, 120.7, 116.5, 54.4, 48.2, 25.5, 20.4;

HRMS (ESI-MS) calcd for $C_{24}H_{23}ClN_2NaO_4S^+$ [M+Na$^+$] 493.0965. found 493.0945.

Production Example 47

Production of 1-(2-(4'-methoxy-2'-methyl-[1,1'-biphenyl]-4-yl)-2-oxoethyl)-5-(pyrrolidin-1-ylsulfonyl)pyridin-2(1H)-one (Compound TS-59)

Compound TS-59 was produced as a light-brown solid with a yield of 90% in a similar manner as described in Production Example 1(2), using compound II and (4-methoxy-2-methylphenyl)boronic acid. The following are physicochemical properties of the obtained compound TS-59.

$^1$H NMR (400 MHz, CDCl$_3$) δ 8.04 (d, J=8.3 Hz, 2H), 7.94 (d, J=2.6 Hz, 1H), 7.67 (dd, J=9.6, 2.6 Hz, 7.47 (d, J=8.3 Hz, 2H), 7.17 (d, J=8.1 Hz, 1H), 6.78-6.82 (m, 2H), 6.64 (d, J=9.6 Hz, 1H), 5.47 (s, 2H), 3.85 (s, 3H), 3.23-3.34 (m, 4H), 2.28 (s, 3H), 1.83-1.96 (m, 4H);

$^{13}$C NMR (100 MHz, CDCl$_3$) δ 191.1, 161.6, 159.6, 148.4, 142.2, 137.0, 136.8, 133.1, 132.5, 130.8, 130.2, 128.2, 120.7, 116.4, 116.2, 111.6, 55.4, 54.3, 48.2, 25.5, 20.9;

HRMS (ESI-MS) calcd for C$_{25}$H$_{26}$N$_2$NaO$_5$S$^+$ [M+Na$^+$] 489.1460. found 489.1450.

Production Example 48

Production of 1-(2-(2'-chloro-4'-methoxy-[1,1'-biphenyl]-4-yl)-2-oxoethyl)-5-(pyrrolidin-1-ylsulfonyl)pyridin-2(1H)-one (Compound TS-60)

Compound TS-60 was produced as a light-yellow solid with a yield of 93% in a similar manner as described in Production Example 1(2), using compound II and (2-chloro-4-methoxyphenyl)boronic acid. The physicochemical property of obtained combination portion TS-60 is as follows.

$^1$H NMR (500 MHz, CDCl$_3$) δ 8.07 (d, J=8.5 Hz, 2H), 7.97 (d, J=2.5 Hz, 1H), 7.68 (dd, J=9.6 2.5 Hz, 1H), 7.61 (d, J=8.3 Hz, 2H), 7.29 (d, J=8.6 Hz, 1H), 7.07 (d, 2.6 Hz, 1H), 6.94 (dd, J=8.6, 2.6 Hz, 1H), 6.65 (d, J=9.5 Hz, 1H), 5.50 (s, 2H), 3.86 (s, 3H), 3.22-3.37 (m, 4H), 1.85-1.87 (m, 4H);

$^{13}$C NMR (125 MHz, CDCl$_3$) δ 191.2, 161.6, 160.2, 145.5, 142.2, 136.9, 133.0, 133.0, 131.8, 131.5, 130.4, 128.1, 120.7, 116.4, 115.6, 113.5, 55.8, 54.4, 48.2, 25.5;

HRMS (ESI-MS) calcd for C$_{24}$H$_{23}$ClN$_2$NaO$_5$S$^+$ [M+Na$^+$] 509.0914. found 509.0894.

Production Example 49

Production of 5-(azepan-1-ylsulfonyl)-1-(2-oxo-2-(3'-(trifluoromethyl)-[1,1'-biphenyl]-4-yl)ethyl)pyridin-2(1H)-one (Compound TS-61)

Compound TS-61 was produced as an orange wax with a yield of 74% in a similar manner as described in Production Example 1, using 5-(azepan-1-ylsulfonyl)pyridin-2(1H)-one in place of Compound I. The following are physicochemical properties of the obtained compound TS-61.

$^1$H NMR (400 MHz, CDCl$_3$) δ 8.11 (d, J=8.1 Hz, 2H), 7.57-7.96 (m, 8H), 6.64 (d, J=9.4 Hz, 1H), 5.46 (s, 2H), 3.36 (t, J=5.4 Hz, 4H), 1.76 (brs, 4H), 1.63 (brs, 4H);

$^{13}$C NMR (100 MHz, CDCl$_3$) δ 191.0, 161.6, 145.6, 141.6, 140.4, 136.6, 133.7, 131.7 (q, J=32.5 Hz), 130.7, 129.7, 129.1, 127.9, 125.3 (q, J=3.8 Hz), 124.2 (q, J=3.7 Hz), 124.1 (q, J=272.5 Hz), 121.0, 118.8, 54.5, 48.3, 29.3, 27.0;

HRMS (ESI-MS) calcd for C$_{26}$H$_{25}$F$_3$N$_2$NaO$_4$S$^+$ [M+Na$^+$] 541.1385. found 541.1397.

Production Example 50

Production of 5-(azepan-1-ylsulfonyl)-1-(2-oxo-2-(4'-(trifluoromethyl)-[1,1'-biphenyl]-4-yl)ethyl)pyridin-2(1H)-one (Compound TS-62)

Compound TS-62 was produced as a light-yellow wax with a yield of 79% in a similar manner as described in Production Example 1, using 5-(azepan-1-ylsulfonyl)pyridin-2(1H)-one in (1) in place of compound I, and using [4-(trifluoromethyl)phenyl]boronic acid in (2) in place of [3-(trifluoromethyl)phenyl]boronic acid. The following are physicochemical properties of the obtained compound TS-62.

$^1$H NMR (500 MHz, CDCl$_3$) δ 8.11 (d, J=8.3 Hz, 2H), 7.91 (d, J=2.7 Hz, 1H), 7.74-7.78 (m, 6H), 7.61 (dd, J=9.7, 2.7 Hz, 1H), 6.64 (d, J=9.7 Hz, 1H), 5.44 (s, 2H), 3.34 (t, J=6.0 Hz, 4H), 1.76 (brs, 4H), 1.61-1.67 (m, 4H);

$^{13}$C NMR (125 MHz, CDCl$_3$) δ 191.2, 161.8, 145.9, 143.4 (q, J=3.8 Hz), 141.8, 136.9, 134.2, 131.0 (q, J=32.7 Hz), 129.3, 128.3, 128.1, 126.4 (q, J=3.8 Hz), 124.5 (q, J=271.5 Hz), 121.2, 119.1, 54.8, 48.6, 30.0, 27.3;

HRMS (ESI-MS) calcd for C$_{26}$H$_{25}$F$_3$N$_2$NaO$_4$S$^+$ [M+Na$^+$] 541.1385. found 541.1397.

Production Example 51

Production of 5-(azepan-1-ylsulfonyl)-1-(2-(4'-chloro-[1,1'-biphenyl]-4-yl)-2-oxoethyl)pyridin-2(1H)-one (Compound TS-63)

Compound TS-63 was produced as a light-yellow wax with a yield of 86% in a similar manner as described in Production Example 1, using 5-(azepan-1-ylsulfonyl)pyridin-2(1H)-one in (1) in place of Compound I, and using (4-chlorophenyl)boronic acid in (2) in place of [3-(trifluoromethyl) phenyl]boronic acid. The following are physicochemical properties of the obtained compound TS-63.

$^1$H NMR (500 MHz, CDCl$_3$) δ 8.08 (d, J=8.2 Hz, 2H), 7.90 (d, J=2.6 Hz, 1H), 7.71 (d, J=8.2 Hz, 2H), 7.61 (dd, J=9.7, 2.6 Hz, 1H), 7.57 (d, J=8.3 Hz, 2H), 7.46 (d, J=8.3 Hz, 2H), 6.64 (d, J=9.7 Hz, 1H), 5.43 (s, 2H), 3.34 (t, J=5.9 Hz, 4H), 1.76 (brs, 4H), 1.60-1.67 (m, 4H).

$^{13}$C NMR (125 MHz, CDCl$_3$) δ 190.9, 161.6, 146.0, 141.5, 138.0, 136.6, 135.0, 133.4, 129.4, 129.0, 128.7, 127.6, 121.0, 118.8, 54.4, 48.4, 29.3, 27.1.

HRMS (ESI-MS) calcd for C$_{25}$H$_{22}$ClN$_2$NaO$_4$S$^+$ [M+Na$^+$] 484.9950. found 507.1141.

Production Example 52

Production of 5-(azepan-1-ylsulfonyl)-1-(2-(4'-chloro-2'-methyl-[1,1'-biphenyl]-4-yl)-2-oxoethyl)pyridin-2(1H)-one (Compound TS-64)

Compound TS-64 was produced as a colorless solid with a yield of 52% in a similar manner as described in Production Example 1, using 5-(azepan-1-ylsulfonyl)pyridin-2 (1H)-one in (1) in place of compound I, and using (4-chloro-2-methylphenyl)boronic acid in (2) in place of [3-(trifluoromethyl)phenyl]boronic acid. The following are physicochemical properties of the obtained compound TS-64.

$^1$H NMR (500 MHz, CDCl$_3$) δ 8.04-8.08 (m, 2H), 7.90 (d, J=2.6 Hz, 1H), 7.61 (dd, J=9.7, 2.6 Hz, 1H), 7.44-7.47 (m, 2H), 7.30 (d, J=2.0 Hz, 1H), 7.24-7.28 (m, 1H), 7.16 (d, J=8.0 Hz, 1H), 6.65 (d, J=9.7 Hz, 1H), 5.44 (s, 2H), 3.35 (t, J=6.0 Hz, 4H), 2.25 (s, 3H), 1.77 (brs, 4H), 1.60-1.67 (m, 4H);

$^{13}$C NMR (125 MHz, CDCl$_3$) δ 191.0, 161.6, 147.3, 141.5, 138.9, 137.2, 136.6, 134.1, 133.2, 130.8, 130.6, 130.0, 128.3, 126.3, 121.0, 118.9, 54.5, 48.4, 29.3, 27.1, 20.4;

HRMS (ESI-MS) calcd for $C_{26}H_{27}ClN_2NaO_4S^+$ [M+Na$^+$] 521.1278. found 521.1262.

Production Example 53

Production of N,N-diethyl-6-oxo-1-(2-oxo-2-(3'-(trifluoromethyl)-[1,1'-biphenyl]-4-yl)ethyl)-1,6-dihydropyridine-3-sulfonamide (Compound TS-65)

Compound TS-65 was produced as a light-yellow oil with a yield of 79% in a similar manner as described in Production Example 1, using N,N-diethyl-6-oxo-1,6-dihydropyridine-3-sulfonamide in place of compound I. The following are physicochemical properties of the obtained compound TS-65.

$^1$H NMR (500 MHz, CDCl$_3$) δ 8.11 (d, J=8.3 Hz, 2H), 7.93 (d, J=2.3 Hz, 1H), 7.87 (s, 1H), 7.82 (d, J=7.9 Hz, 1H), 7.76 (d, J=8.3 Hz, 2H), 7.69 (d, J=7.9 Hz, 1H), 7.58-7.65 (m, 2H), 6.64 (d, J=9.8 Hz, 1H), 5.45 (s, 2H), 3.30 (q, J=7.1 Hz, 4H), 1.21 (t, J=7.1 Hz, 6H);
$^{13}$C NMR (125 MHz, CDCl$_3$) δ 191.2, 161.8, 145.9, 141.9, 140.7, 136.9, 134.0, 132.0 (q, J=32.6 Hz), 131.0 (q, J=1.0 Hz), 130.0, 129.3, 128.2, 125.6 (q, J=3.8 Hz), 124.5 (q, J=3.8 Hz), 124.4 (q, J=272.3 Hz), 121.2, 119.7, 54.8, 42.4, 14.6;
HEMS(ESI-MS) calcd for $C_{24}H_{23}F_3N_2NaO_4S^+$ [M+Na$^+$] 515.1228. found 515.1240.

Production Example 54

Production of N,N-diethyl-6-oxo-1-(2-oxo-2-(4'-(trifluoromethyl)-[1,1'-biphenyl]-4-yl)ethyl)-1,6-dihydropyridine-3-sulfonamide (Compound TS-66)

Compound TS-66 was produced as a colorless solid with a yield of 90% in a similar manner as described in Production Example 1, using N,N-diethyl-6-oxo-1,6-dihydropyridine-3-sulfonamide in (1) in place of compound I, and using [4-(trifluoromethyl)phenyl]boronic acid in (2) in place of [3-(trifluoromethyl)phenyl]boronic acid. The following are physicochemical properties of the obtained compound TS-66.

$^1$H NMR (500 MHz, CDCl$_3$) δ 8.11 (d, J=8.0 Hz, 2H), 7.93 (d, J=2.6 Hz, 1H), 7.72-7.78 (m, 6H), 7.60 (dd, J=9.7, 2.6 Hz, 1H), 6.64 (d, J=9.7 Hz, 1H), 5.45 (s, 2H), 3.29 (q, J=7.2 Hz, 4H), 1.20 (t, J=7.2 Hz, 6H);
$^{13}$C NMR (125 MHz, CDCl$_3$) δ 191.0, 161.5, 145.6, 143.1, 141.7, 136.6, 133.9, 130.7 (q, J=32.8 Hz), 129.0, 128.0, 127.8, 126.1 (q, J=3.8 Hz), 124.2 (q, J=272.5 Hz), 120.9, 119.5, 54.5, 42.1, 14.3;
HRMS (ESI-MS) calcd for $C_{24}H_{23}F_3N_2NaO_4S^+$ [M+Na$^+$] 515.1228. found 515.1240.

Production Example 55

Production of 1-(2-(4'-chloro-[1,1'-biphenyl]-4-yl)-2-oxoethyl)-N,N-diethyl-6-oxo-1,6-dihydropyridine-3-sulfonamide (Compound TS-67)

Compound TS-67 was produced as a light-yellow wax with a yield of 97% in a similar manner as described in Production Example 1, using N,N-diethyl-6-oxo-1,6-dihydropyridine-3-sulfonamide in (1) in place of compound I, and using (4-chlorophenyl)boronic acid in (2) in place of [3-(trifluoromethyl)phenyl]boronic acid. The following are physicochemical properties of the obtained compound TS-67.

$^1$H NMR (500 MHz, CDCl$_3$) δ 8.07 (d, J=8.3 Hz, 2H), 7.91 (d, J=2.6 Hz, 1H), 7.71 (d, J=8.3 Hz, 2H), 7.60 (dd, J=9.8, 2.6 Hz, 1H), 7.57 (d, J=8.3 Hz, 2H), 7.46 (d, J=8.3 Hz, 2H), 6.63 (d, J=9.8 Hz, 1H), 5.43 (s, 2H), 3.30 (d, J=7.2 Hz, 4H), 1.21 (t, J=7.2 Hz, 6H);
$^{13}$C NMR (125 MHz, CDCl$_3$) δ 190.9, 161.5, 146.0, 141.7, 138.0, 136.6, 135.0, 133.4, 129.4, 129.0, 128.7, 127.6, 121.0, 119.4, 54.4, 42.1, 14.3;
HRMS (ESI-MS) calcd for $C_{23}H_{23}ClN_2NaO_4S^+$ [M+Na$^+$] 481.0965. found 481.0986.

Production Example 56

Production of 1-(2-(4'-chloro-2'-methyl-[1,1'-biphenyl]-4-yl)-2-oxoethyl)-N,N-diethyl-6-oxo-1,6-dihydropyridine-3-sulfonamide (Compound TS-68)

Compound TS-68 was produced as a light-yellow wax with a yield of 97% in a similar manner as described in Production Example 1, using N,N-diethyl-6-oxo-1,6-dihydropyridine-3-sulfonamide in (1) in place of compound I, and using (4-chloro-2-methylphenyl)boronic acid in (2) in place of [3-(trifluoromethyl)phenyl]boronic acid. The following are physicochemical properties of the obtained compound TS-68.

$^1$H NMR (500 MHz, CDCl$_3$) δ 8.06 (d, J=8.6 Hz, 2H), 7.92 (d, J=2.5 Hz, 1H), 7.61 (dd, J=9.7, 2.5 Hz, 1H), 7.45 (d, J=8.6 Hz, 2H), 7.30 (d, J=1.7 Hz, 1H), 7.25 (d, J=1.7 Hz, 1H), 7.16 (d, J=8.3 Hz, 1H), 6.64 (d, J=9.7 Hz, 1H), 5.44 (s, 2H), 3.30 (q, J=7.2 Hz, 4H), 2.27 (s, 3H), 1.21 (t, J=7.2 Hz, 6H);
$^{13}$C NMR (125 MHz, CDCl$_3$) δ 191.0, 161.6, 147.3, 141.7, 138.9, 137.2, 136.6, 134.0, 133.2, 130.8, 130.6, 130.0, 128.3, 126.3, 121.0, 119.4, 54.5, 42.1, 20.4, 14.3;
HRMS (ESI-MS) calcd for $C_{24}H_{25}ClN_2NaO_4S^+$ [M+Na$^+$] 495.1121. found 495.1145.

Production Example 57

Production of 1-(2-([1,1'-biphenyl]-4-yl)-2-oxoethyl)-5-(pyrrolidin-1-ylsulfonyl)pyridin-2(1H)-one (Compound TS-09)

Compound TS-09 was produced as a light-yellow solid with a yield of 81% in a similar manner as described in Production Example 1(1), using compound I and 1-([1,1'-biphenyl]-4-yl)-2-bromoethanone. The following are physicochemical properties of the obtained compound TS-09.

$^1$H NMR (500 MHz, CDCl$_3$) δ 8.07 (d, J=8.2 Hz, 2H), 7.95 (d, J=2.6 Hz, 1H), 7.74 (d, J=8.2 Hz, 7.74), 7.62-7.68 (m, 3H), 7.49 (dd, J=7.4, 7.4 Hz, 2H), 7.43 (dd, J=7.4, 7.4 Hz, 1H), 6.63 (d, J=9.8 Hz, 1H), 5.47 (s, 2H), 3.22-3.35 (m, 4H), 1.82-1.95 (m, 4H);
$^{13}$C NMR (125 MHz, CDCl$_3$) δ 191.1, 161.6, 147.2, 142.3, 139.6, 137.0, 136.9, 133.1, 129.2, 128.9, 127.7, 127.4, 120.7, 116.4, 54.3, 48.2, 25.5;
HRMS (ESI-MS) calcd for $C_{23}H_{22}N_2NaO_4S^+$ [M+Na$^+$] 445.1189 found 445.1189.

Production Example 58

Production of 1-(2-(1-(4-fluorobenzyl)-2,5-dimethyl-1H-pyrrol-3-yl)-2-oxoethyl)-5-(pyrrolidin-1-ylsulfonyl)pyridin-2(1H)-one (Compound T-070444)

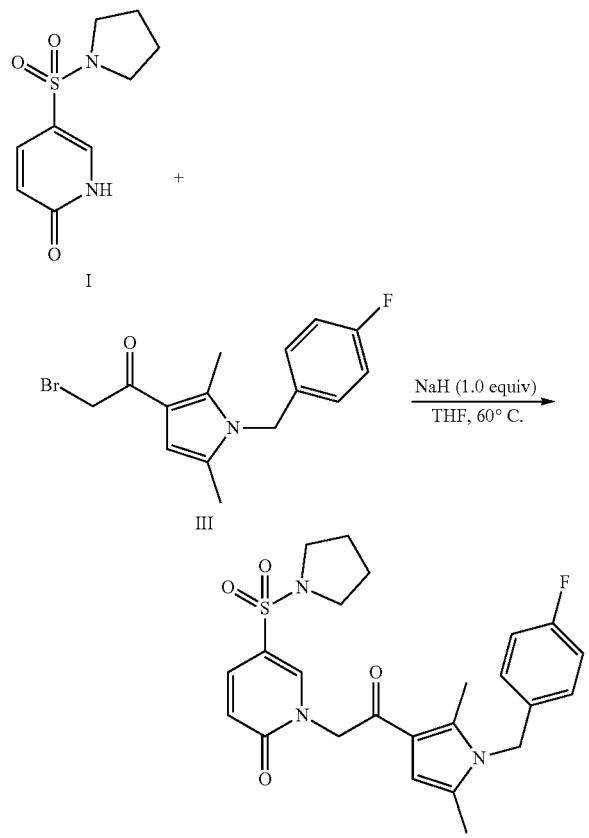

5-(Pyrrolidin-1-ylsulfonyl)pyridin-2(1H)-one (compound I; 228 g, 1.0 mmol) was dissolved in THF (7.5 mL), and sodium hydride (purity: 60%, 1.0 mmol) was added thereto at room temperature, followed by stirring at 60° C. for 60 minutes. Then, a solution of 2-bromo-1-(1-(4-fluorobenzyl)-2,5-dimethyl-1H-pyrrol-3-yl)ethanone (compound III) in THF (5 mL, 1.0 mmol) was added to the mixture, followed by stirring at 60° C. for 60 minutes. After the reaction solution was cooled to room temperature, water was carefully added to stop the reaction. The obtained reaction product was extracted with $CH_2Cl_2$, and the collected organic phase was sequentially washed with water and brine. The organic phase was dehydrated with $MgSO_4$, and the solvent was evaporated under reduced pressure. The obtained crude product was purified by silica gel column chromatography (ethyl acetate) to obtain the title compound (T-070444) as a light-yellow solid (yield: 49%). The following are physicochemical properties of the obtained T-070444.

$^1$H NMR (400 MHz, CDCl$_3$) δ 7.89 (d, J=2.7 Hz, 1H), 7.63 (dd, J=9.4, 2.7 Hz, 1H), 6.98-7.07 (m, 2H), 6.83 (m, 2H), 6.62 (d, J=9.9 Hz, 1H), 6.39 (s, 1H), 5.19 (s, 2H), 5.03 (s, 2H), 3.27-3.34 (m, 4H), 2.45 (s, 3H), 2.15 (s, 3H), 1.85-1.91 (m, 4H).

Production Example 59

Production of 1-(2-(1-(4-fluorophenyl)-2,5-dimethyl-1H-pyrrol-3-yl)-2-oxoethyl)-5-(pyrrolidin-1-ylsulfonyl)pyridin-2(1H)-one (Compound TS-07)

Compound TS-07 was produced as a light-brown solid with a yield of 64% in a similar manner as described in Production Example 58, using compound I and 2-bromo-1-(1-(4-fluorophenyl)-2,5-dimethyl-1H-pyrrol-3-yl)ethanone. The following are physicochemical properties of the obtained compound TS-07.

$^1$H NMR (500 MHz, CDCl$_3$) δ 7.91 (d, J=2.5 Hz, 1H), 7.64 (dd, J=9.5, 2.5 Hz, 1H), 7.11-7.25 (m, 4H), 6.62 (d, J=9.5 Hz, 1H), 6.42 (s, 1H), 5.19 (s, 2H), 3.22-3.40 (m, 4H), 2.29 (s, 3H), 2.00 (s, 3H), 1.82-1.95 (m, 4H);

$^{13}$C NMR (125 MHz, CDCl$_3$) δ 186.8, 162.7 (d, J=249.5 Hz), 161.8, 142.6, 137.9, 136.7, 133.1, 133.0, 130.0, 129.9 (d, J=8.4 Hz), 120.6, 116.8 (d, J=22.8 Hz), 115.9, 106.7, 55.2, 48.2, 25.5, 13.1, 12.8;

HRMS (ESI-MS) calcd for $C_{23}H_{24}FN_3NaO_4S^+$ [M+Na$^+$] 480.1369 found 480.1385.

Production Example 60

Production of 1-(2-(1-(4-methoxyphenyl)-2,5-dimethyl-1H-pyrrol-3-yl)-2-oxoethyl)-5-(pyrrolidin-1-ylsulfonyl)pyridin-2(1H)-one (Compound TS-08)

Compound TS-08 was produced as a light-yellow oil with a yield of 64% in a similar manner as described in Production Example 58, using compound I and 2-bromo-1-(1-(4-methoxyphenyl)-2,5-dimethyl-1H-pyrrol-3-yl)ethanone. The following are physicochemical properties of the obtained compound TS-08.

$^1$H NMR (500 MHz, CDCl$_3$) δ 7.91 (d, J=2.5 Hz, 1H), 7.64 (dd, J=9.8, 2.5 Hz, 1H), 7.06-7.11 (m, 2H), 6.98-7.03 (m, 2H), 6.62 (d, J=9.8 Hz, 1H), 6.40 (s, 1H), 5.19 (s, 2H), 3.88 (s, 3H), 3.23-3.35 (m, 4H), 2.29 (s, 3H), 2.00 (s, 3H), 1.82-1.93 (m, 4H);

$^{13}$C NMR (125 MHz, CDCl$_3$) δ 187.0, 162.0, 160.2, 142.9, 138.5, 137.0, 130.6, 130.0, 129.3, 120.9, 117.4, 116.1, 115.1, 106.6, 56.0, 55.4, 48.5, 25.7, 13.4, 13.1;

HRMS (ESI-MS) calcd for $C_{24}H_{27}N_3NaO_5S^+$ [M+Na$^+$] 492.1569 found 492.1555.

Production Example 61

Production of 1-(2-(1-(4-fluorobenzyl)-2,5-dimethyl-1H-pyrrol-3-yl)-2-oxoethyl)pyridin-2(1H)-one (Compound NT-07)

Compound NT-07 was produced as a light-brown solid with a yield of 52% in a similar manner as described in Production Example 58, using pyridin-2(1H)-one and 2-bromo-1-(1-(4-fluorobenzyl)-2,5-dimethyl-1H-pyrrol-3-yl)ethanone (compound III). The physicochemical property of obtained compound NT-07 is as follows.

$^1$H NMR (500 MHz, CDCl$_3$) δ 7.36 (ddd, J=9.1, 7.0, 2.0 Hz, 1H), 7.22 (dd, J=7.0, 2.0 Hz, 1H), 7.00 (dd, J=8.5, 8.5 Hz, 2H), 6.85 (dd, J=8.5, 5.5 Hz, 2H), 6.60 (d, J=9.1 Hz, 1H), 6.42 (s, 1H), 6.19 (ddd, J=7.0, 7.0, 1.5 Hz, 1H), 5.16 (s, 2H), 5.01 (s, 2H), 2.46 (s, 3H), 2.14 (s, 3H);

$^{13}$C NMR (125 MHz, CDCl$_3$) δ 188.1, 162.7, 162.3 (d, J=246.5 Hz), 139.9, 138.8, 136.9, 132.2 (d, J=3.0 Hz), 128.7, 127.3 (d, J=8.4 Hz), 120.9, 117.5, 116.1 (d, J=21.6 Hz), 107.3, 105.7, 54.9, 46.2, 12.3, 11.9;

Production Example 62

Production of N,N-diallyl-1-(2-(1-(4-fluorobenzyl)-2,5-dimethyl-1H-pyrrol-3-yl)-2-oxoethyl)-6-oxo-1,6-dihydropyridine-3-sulfonamide (Compound TS-10)

Compound TS-10 was produced as a light-brown solid with a yield of 46% in a similar manner as described in Production Example 58, using N,N-diallyl-6-oxo-1,6-dihydropyridine-3-sulfonamide and 2-bromo-1-(1-(4-fluorobenzyl)-2,5-dimethyl-1H-pyrrol-3-yl)ethanone (compound III). The following are physicochemical properties of the obtained compound TS-10.

$^1$H NMR (400 MHz, CDCl$_3$) δ 7.89 (d, J=2.6 Hz, 1H), 7.57 (dd, J=9.7, 2.6 Hz, 1H), 7.02 (dd, J=8.3 Hz, 2H), 6.86 (dd, J=8.3, 5.5 Hz, 2H), 6.61 (d, J=9.7 Hz, 1H), 6.38 (s, 1H), 5.66-5.83 (m, 2H), 5.12-5.29 (m, 6H), 5.03 (s, 2H), 3.84 (d, J=6.3 Hz, 4H), 2.46 (s, 3H), 2.15 (s, 3H);
$^{13}$C NMR (100 MHz, CDCl$_3$) δ 186.5, 162.3 (d, J=246.6 Hz), 161.7, 142.5, 137.1, 136.3, 132.6, 132.1 (d, J=3.3 Hz), 129.1, 127.3 (d, J=8.0 Hz), 120.8, 120.0, 118.6, 117.1, 116.1 (d, J=21.9 Hz), 107.1, 55.2, 49.5, 46.2, 12.4, 12.0;
HRMS (ESI-MS) calcd for C$_{26}$H$_{28}$F$_1$N$_3$NaO$_4$S$^+$ [M+Na$^+$] 520.1682 found 520.1703.

Production Example 63

Production of 1-(2-(1-benzyl-2,5-dimethyl-1H-pyrrol-3-yl)-2-oxoethyl)-5-(pyrrolidin-1-ylsulfonyl)pyridin-2(1H)-one (Compound NT-01)

Compound NT-01 was produced as a light-brown solid with a yield of 84% in a similar manner as described in Production Example 58, using compound I and 2-bromo-1-(1-benzyl-2,5-dimethyl-1H-pyrrol-3-yl)ethanone. The following are physicochemical properties of the obtained compound NT-01.

The Rf value (developing solvent; ethyl acetate 100%) of TLC (silica gel) was 0.62.

Production Example 64

Production of 1-(2-(2,5-dimethyl-1-(4-methylbenzyl)-1H-pyrrol-3-yl)-2-oxoethyl)-5-(pyrrolidin-1-ylsulfonyl)pyridin-2(1H)-one (Compound NT-02)

Compound NT-02 was produced as a light-brown solid with a yield of 63% in a similar manner as described in Production Example 58, using compound I and 2-bromo-1-(2,5-dimethyl-1-(4-methylbenzyl)-1H-pyrrol-3-yl)ethanone. The following are physicochemical properties of the obtained compound NT-02.

$^1$H NMR (500 MHz, CDCl$_3$) δ 7.90 (d, J=2.6 Hz, 1H), 7.63 (dd, J=9.7, 2.6 Hz, 1H), 7.11-7.16 (m, 2H), 6.74-6.81 (m, 2H), 6.61 (d, J=9.7 Hz, 1H), 6.38 (s, 1H), 5.19 (s, 2H), 5.02 (s, 2H), 3.26-3.32 (m, 4H), 2.46 (s, 3H), 2.32 (s, 3H), 2.15 (s, 3H), 1.85-1.92 (m, 4H).

Production Example 65

Production of 1-(2-(1-(4-chlorobenzyl)-2,5-dimethyl-1H-pyrrol-3-yl)-2-oxoethyl)-5-(pyrrolidin-1-ylsulfonyl)pyridin-2(1H)-one (Compound NT-03)

Compound NT-03 was produced as a light-brown solid with a yield of 14% in a similar manner as described in Production Example 58, using compound I and 2-bromo-1-((4-chlorobenzyl)-2,5-dimethyl-1H-pyrrol-3-yl)ethanone.
The following are physicochemical properties of the obtained compound NT-03.
The Rf value (developing solvent; hexane 33%, ethyl acetate 67%) of TLC (silica gel) was 0.18.

Production Example 66

Production of 1-(2-(1-(4-bromobenzyl)-2,5-dimethyl-1H-pyrrol-3-yl)-2-oxoethyl)-5-(pyrrolidin-1-ylsulfonyl)pyridin-2(1H)-one (Compound NT-04)

Compound NT-04 was produced as a light-brown solid with a yield of 50% in a similar manner as described in Production Example 38, using compound I and 2-bromo-1-((4-bromobenzyl)-2,5-dimethyl-1H-pyrrol-3-yl)ethanone.
The following are physicochemical properties of the obtained compound NT-04.

$^1$H NMR (500 MHz, CDCl$_3$) δ 7.89 (d, J=2.6 Hz, 1H), 7.64 (dd, J=9.7, 2.6 Hz, 1H), 7.42-7.47 (m, 2H), 6.73-6.79 (m, 2H), 6.62 (d, J=9.7 Hz, 1H), 6.39 (d, J=0.9 Hz, 1H), 5.18 (s, 2H), 5.00 (s, 2H), 3.26-3.33 (m, 4H), 2.45 (s, 3H), 2.14 (s, 3H), 1.85-1.92 (m, 4H).

Production Example 67

Production of 1-(2-(1-(4-methoxybenzyl)-2,5-dimethyl-1H-pyrrol-3-yl)-2-oxoethyl)-5-(pyrrolidin-1-ylsulfonyl)pyridin-2(1H)-one (Compound NT-05)

Compound NT-05 was produced as a colorless solid with a yield of 41% in a similar manner as described in Production Example 58, using compound I and 2-bromo-1-((4-methoxybenzyl)-2,5-dimethyl-1H-pyrrol-3-yl)ethanone.
The following are physicochemical properties of the obtained compound NT-05.

$^1$H NMR (500 MHz, CDCl$_3$) δ 7.89 (d, J=2.6 Hz, 1H), 7.63 (dd, J=9.5, 2.6 Hz, 1H), 6.80-6.90 (m, 4H), 6.62 (d, J=9.5 Hz, 1H), 6.37 (d, J=0.9 Hz, 1H), 5.19 (s, 2H), 5.00 (s, 2H), 3.78 (s, 3H), 3.26-3.35 (m, 4H), 2.47 (s, 3H), 2.16 (s, 3H), 1.85-1.93 (m, 4H).

Production Example 68

Production of 1-(2-(1-(4-fluorobenzyl)-2,5-dimethyl-1H-pyrrol-3-yl)-2-oxoethyl)-5-(piperidin-1-ylsulfonyl)pyridin-2(1H)-one (Compound NT-08)

Compound NT-08 was produced as a light orange solid with a yield of 30% in a similar manner as described in Production Example 58, using 5-(piperidin-1-ylsulfonyl)pyridin-2(1H)-one and compound III. The following are physicochemical properties of the obtained compound NT-08.

$^1$H NMR (500 MHz, CDCl$_3$) δ 7.83 (d, J=2.6 Hz, 1H), 7.55 (dd, J=9.5, 2.6 Hz, 1H), 6.98-7.05 (m, 2H), 6.84-6.90 (m, 2H), 6.60 (d, J=9.5 Hz, 1H), 6.39 (s, 1H), 5.18 (s, 2H), 5.03 (s, 2H), 3.07-3.15 (m, 4H), 2.46 (s, 3H), 2.15 (s, 3H), 1.63-1.70 (m, 4H), 1.46-1.54 (m, 2H).

Production Example 69

Production of 5-(azepan-1-ylsulfonyl)-1-(2-(1-(4-fluorobenzyl)-2,5-dimethyl-1H-pyrrol-3-yl)-2-oxoethyl)pyridin-2(1H)-one (Compound NT-09)

Compound NT-09 was produced as a light-yellow solid with a yield of 47% in a similar manner as described in Production Example 58, using 5-(azepan-1-ylsulfonyl)pyridin-2(1H)-one and compound III. The following are physicochemical properties of the obtained compound NT-09.

$^1$H NMR (500 MHz, CDCl$_3$) δ 7.86 (d, J=2.6 Hz, 1H), 7.57 (dd, J=9.7, 2.6 Hz, 1H), 6.99-7.05 (m, 2H), 6.84-6.90 (m, 2H), 6.61 (d, J=9.7 Hz, 1H), 6.39 (d, J=0.9 Hz, 1H), 5.17 (s, 2H), 5.03 (s, 2H), 3.31-3.36 (m, 4H), 2.46 (s, 3H), 2.15 (s, 3H), 1.70-1.79 (m, 4H), 1.59-1.64 (m, 4H).

Production Example 70

Production of 1-(2-(1-(4-fluorobenzyl)-2,5-dimethyl-1H-pyrrol-3-yl)-2-oxoethyl)-5-(thiomorpholinosulfonyl)pyridin-2(1H)-one (Compound NT-10)

Compound NT-10 was produced as a light-brown solid with a yield of 16% in a similar manner as described in Production Example 58, using 5-(thiomorpholinosulfonyl)pyridin-2(1H)-one and compound III. The following are physicochemical properties of the obtained compound NT-10.

The Rf value (developing solvent; hexane 50%, ethyl acetate 50%) of TLC (silica gel) was 0.1.

Production Example 71

Production of 1-(2-(1-(4-fluorobenzyl)-2,5-dimethyl-1H-pyrrol-3-yl)-2-oxoethyl)-5-(morpholinosulfonyl)pyridin-2(1H)-one (Compound NT-11)

Compound NT-11 was produced as a colorless solid with a yield of 45% in a similar manner as described in Production Example 58, using 5-(morpholinosulfonyl)pyridin-2(1H)-one and compound III. The following are physicochemical properties of the obtained compound NT-11.

$^1$H NMR (500 MHz, CDCl$_3$) δ 7.85 (d, J=2.6 Hz, 1H), 7.55 (dd, J=9.7, 2.6 Hz, 1H), 6.99-7.05 (m, 2H), 6.84-6.90 (m, 2H), 6.63 (d, J=9.7 Hz, 1H), 6.39 (d, J=0.9 Hz, 1H), 5.19 (s, 2H), 5.03 (s, 2H), 3.75-3.82 (m, 4H), 3.11-3.18 (m, 4H), 2.46 (s, 3H), 2.15 (s, 3H).

Production Example 72

Production of N,N-diethyl-1-(2-(1-(4-fluorobenzyl)-2,5-dimethyl-1H-pyrrol-3-yl)-2-oxoethyl)-6-oxo-1,6-dihydropyridine-3-sulfonamide (Compound NT-12)

Compound NT-12 was produced as a light-brown solid with a yield of 32% in a similar manner as described in Production Example 58, using N,N-diethyl-6-oxo-1,6-dihydropyridine-3-sulfonamide and compound III. The following are physicochemical properties of the obtained NT-12.

$^1$H NMR (500 MHz, CDCl$_3$) δ 7.88 (d, J=2.6 Hz, 1H), 7.56 (dd, J=9.7, 2.6 Hz, 1H), 6.99-7.05 (m, 2H), 6.84-6.89 (m, 2H), 6.61 (d, J=9.7 Hz, 1H), 6.39 (d, J=0.9 Hz, 1H), 5.17 (s, 2H), 5.03 (s, 2H), 3.28 (q, J=7.2 Hz, 4H), 2.46 (s, 3H), 2.15 (s, 3H), 1.20 (t, J=7.2 Hz, 6H).

Production Example 73

Production of 1-(2-(1-(4-hydroxybenzyl)-2,5-dimethyl-1H-pyrrol-3-yl)-2-oxoethyl)-5-(pyrrolidin-1-ylsulfonyl)pyridin-2(1H)-one (Compound NT-13)

Compound NT-13 was produced as a light-brown solid with a yield of 12% in a similar manner as described in Production Example 58, using compound I and 2-bromo-1-((4-hydroxybenzyl)-2,5-dimethyl-1H-pyrrol-3-yl)ethanone. The following are physicochemical properties of the obtained compound NT-13.

$^1$H NMR (500 MHz, CDCl$_3$) δ 7.89 (d, J=2.6 Hz, 1H), 7.64 (dd, J=9.5, 2.6 Hz, 1H), 6.99-7.05 (m, 2H), 6.74-6.82 (m, 4H), 6.62 (d, J=9.5 Hz, 1H), 6.37 (brs, 1H), 5.19 (s, 2H), 4.99 (s, 2H), 3.27-3.33 (m, 4H), 2.47 (s, 3H), 2.16 (s, 3H), 1.86-1.91 (m, 4H).

Production Example 74

Production of 1-(2-(1,2-dimethyl-1H-indol-3-yl)-2-oxoethyl)-5-(pyrrolidin-1-ylsulfonyl)pyridin-2(1H)-one (Compound TS-02)

Compound TS-02 was produced as a light-brown solid with a yield of 65% in a similar manner as described in Production Example 58, using compound I and 2-bromo-1-(1,2-dimethyl-1H-indol-3-yl)ethanone. The following are physicochemical properties of the obtained compound TS-02.

$^1$H NMR (500 MHz, CDCl$_3$) δ 7.94 (d, J=2.9 Hz, 1H), 7.86-7.90 (m, 1H), 7.65 (dd, J=9.5, 2.6 Hz, 1H), 7.35-7.40 (m, 1H), 7.27-7.32 (m, 2H), 6.98-7.07 (m, 2H), 6.62 (d, J=9.7 Hz, 1H), 5.42 (s, 1H), 3.74 (s, 3H), 2.78 (s, 3H), 3.25-3.32 (m, 4H), 1.85-1.92 (m, 4H).

The pyridinone compounds obtained by the above methods were subjected to various pharmacological tests as shown in the following methods.

Pharmacological Test 1 (In Vitro GEF Assay)

DOCK1, DOCK2, and DOCK5, which are DOCK-A subfamily members, catalyze the GTP-GDP exchange reaction for Rac via the DHR-2 domain to activate Rac.

The in vitro GEF assay referred to in this specification used a labeled GTP (Bodipy-FL-GTP, Invitrogen), whose fluorescence intensity increases when bound to Rac.

Polypeptide fragments that correspond to the DHR-2 domain of DOCK1, DOCK2, or DOCK5 were expressed in *E. coli* Arctic express (DE3) cells as N-terminal Histidine-SUMO tag-fused recombinant proteins and purified by affinity column chromatography on nickel-NTA columns.

Rac was expressed in *E. coli* BL21 (DE3) cells as an N-terminal GST tag-fused recombinant protein and purified by affinity column chromatography on glutathione-Sepharose columns.

Subsequently, a reaction solution A containing 20 mM of MES-NaOH, 150 mM of NaCl, 10 mM of MgCl$_2$, and 20 μM of GDP, and having an adjusted pH of 7.0 was incubated at room temperature for 30 minutes while being protected from light in the presence of each of the polypeptide fragments (DHR-2 domains) prepared above and each pyridinone compound or CPYPP dissolved at a predetermined concentration in DMSO or DMSO alone (control) to thus prepare GEF pretreated products. In all of the samples, the final DMSO concentration was adjusted to 3%.

Thereafter, 15 μM of Rac prepared above was added to the reaction solution A and directly allowed to stand on ice for 30 minutes to form a GDP-Rac complex.

Bodipy-FL-GTP was added to 100 μL of the reaction solution A containing the thus prepared GDP-Rac complex to a concentration of 3.6 μM, followed by equilibration at 30° C. for 2 minutes. After equilibration, 50 μL of the pretreated GEF was added for reaction at 30° C.

Changes in fluorescence intensity of Bodipy-FL-GTP were monitored during the reaction using an XS-N (Molecular Devices) or an Enspire spectrofluorometer (Perkin Elmer) (excitation wavelength: 488 nm, emission wavelength: 514 nm). The measured values were corrected so that the fluorescence intensity at the time that the reaction was initiated (0 seconds) was 0.

Then, an approximate curve (hyperbola) was obtained by plotting the calculated correction values on the y axis and the time (t) on the x axis using GraphPad Prism5 (GraphPad software), and the slope at t=0 to 10 seconds was considered to be an initial velocity of guanine nucleotide exchange reaction. The $IC_{50}$ value was calculated taking the initial reaction velocity of the control, to which only a solvent (DMSO) was added, as 100%.

Pharmacological Test 2 (Cellular Invasion Inhibition Assay)

Three hundred microliters of a suspension of a mouse lung carcinoma cell line (3LL), a human fibrosarcoma cell line (HT-1080), or a human colon cancer cell line (DLD-1) in DMEM (serum free) was placed in the upper chamber with Matrigel (BD Biosciences) equilibrated with DMEM (serum free) for 120 minutes, while 500 μL of DMEM (with 10% FCS) was placed in the lower chamber. Each pyridinone compound or CPYPP dissolved at a predetermined concentration in DMSO was added to the culture media in both the upper and lower chambers. As a control, DMSO alone was added to the media. In all of the experiments, the final DMSO concentration was adjusted to 0.2%.

After the resulting products were cultured at 37° C. under 5% $CO_2$ for 22 hours, the chambers were removed, and the culture media were removed. Thereafter, the cells that did not invade and remained on the upper chamber were removed using a cotton swab, and the cells remaining in the lower chamber (cells that invaded into the Matrigel) were stained with Diff-quick (Sysmex). After staining, the inserts were cut out with a blade to prepare slides, and the cells were counted under an optical microscope.

The results were evaluated based on percent cell invasion (%: Invasion) and percent inhibition (%: inhibition). The percent cell invasion was obtained by converting the number of invading cells under each condition to percentage, taking the number of invading cells in the control, to which DMSO was added alone, as 100%; and the percent inhibition was obtained by deducting the percent cell invasion from 100.

Pharmacological Test 3 (Inhibition of Cellular Anchorage Independent Growth)

Soft agar assay was performed to assess the inhibitory effect of the compounds on the anchorage independent growth of cancer cells. $1 \times 10^5$ 3LL cells were suspended in a 0.3% agarose-containing DMEM (with 10% FCS) to which DMSO in which each pyridinone compound or CPYPP was dissolved at a predetermined concentration was added, and the resulting products were stratified on base agar formed in a 6-well plate using DMEM (with 10% FCS) containing 0.7% agar.

After the resulting product was cultured at 37° C. in a 5% $CO_2$ environment for 7 days, the cells were stained with 0.005% crystal violet through a 1-hour reaction at room temperature, and the number of colonies formed was counted.

The results were evaluated based on percent colony formation (%: Colony formation) and percent inhibition (%: Inhibition). The percent colony formation was obtained by converting the number of colonies formed under each condition to percentage, taking the number of colonies formed under the control conditions (DMSO added alone) as 100%; and the percent inhibition (%: Inhibition) was obtained by deducting the percent colony formation from 100.

Pharmacological Test 4 (Experiment on Inhibition of Ruffle Formation in Primary Mouse Embryonic Fibroblasts)

As disclosed in NPL 2, stimulation of primary mouse embryonic fibroblasts (MEFs) with a growth factor, such as PDGF, induces actin cytoskeletal remodeling, leading to the formation of two types of characteristic cellular membrane structures, peripheral ruffles and dorsal ruffles.

The peripheral ruffle and dorsal ruffle formation depends on Rac activation and requires the functions of DOCK1 and DOCK5. Importantly, it is known that the peripheral ruffle formation requires the functions of both DOCK1 and DOCK5 while the dorsal ruffle formation requires the function of DOCK1.

Therefore, the use of various pyridinone compounds in this assay system enables cell-level verification of DOCK1 selectivity.

Wild-type MEFs or MEFs from DOCK1-deficient (D1KO) mouse (obtained by the method disclosed in NPL 2) were suspended in DMEM (with 10% FBS) to a concentration of $2 \times 10^4$ cells/mL, and 150 μL of the resulting product was seeded on the glass portion of fibronectin-coated glass-bottom culture dishes.

After 36-hour culture at 37° C., the medium was changed to DMEM (serum free) containing 0.1% BSA, and 12-hour culture was performed to allow the cells to be serum-starved. Subsequently, the medium was changed to 100 μL of DMEM (serum free) containing DMSO in which each pyridinone compound or CPYPP was dissolved at a predetermined concentration, followed by pretreatment for 1 hour. A control was prepared using a culture medium to which DMSO was added alone. In all of the experiments, the final concentration of DMSO was adjusted to 0.2%.

Thereafter, 100 μL of DMEM that was warmed beforehand to 37° C. (serum free, containing 60 ng/mL of PDGF) was added to the above pretreated cells to stimulate the cells, followed by incubation at 37° C. for 7 minutes and further incubation at room temperature for 10 minutes in 150 μL of 4% paraformaldehyde solution to fix the cells. Then, PBS (containing 0.2% Triton X-100) was added to the fixed cells, and a 5-min incubation at room temperature was performed to permeabilize the cellular membranes. Thereafter, the cells were blocked with BSA, and the actin cytoskeleton was stained with Alexa Fluor 546-labeled phalloidin. Using a Zeiss LSM510 meta confocal laser scanning microscope, the number of cells in which peripheral ruffles and dorsal ruffles were formed was observed and counted.

The results were relatively evaluated based on the ratio of peripheral ruffle or dorsal ruffle formation in the cells under each condition, relative to the percentage of either of the structure formations in MEFs from wild-type mouse to which DMSO was added alone (control cells) (the proportion of cells exhibiting either of the ruffle structures relative to the total number of cells) taken as 1.

Pharmacological Test 5 (Experiment of Inhibition of Macropinocytosis of Cancer Cells)

Macropinocytosis is a phenomenon in which cells take up various substances together with extracellular fluid while extending cellular membranes. Remodeling of actin cytoskeleton through Rac activity is known to be important. It has recently been revealed that oncogenic Ras stimulates uptake of extracellular high molecular weight proteins by means of macropinocytosis to use them as a source of glutamine supply, which plays essential functions for the survival and growth of cancer cells in a nutrient-poor environment; macropinocytosis thus has received significant attention as a novel target of cancer treatment (NPL 3).

One hundred and fifty microliters of $4 \times 10^4$ 3LL cells or HT-1080 cells were seeded on the glass portion of fibronectin-coated glass-bottom culture dishes. After 16-hour culture at 37° C., the medium was changed to DMEM (serum free) and cultured for 24 hours to allow the cells to be serum-starved. Subsequently, the medium was changed to 2 mL of serum-free medium containing DMSO alone or DMSO in which each pyridinone compound was dissolved, followed by pretreatment for 1 hour. The final concentration of DMSO was adjusted to 0.2%.

The cells were added to 180 µL of medium with TMR-dextran (final concentration: 500 µg/mL)-containing DMEM (with 10% FBS) containing DMSO alone or DMSO in which a predetermined concentration of each pyridinone compound was dissolved, as in the case above, followed by incubation at 37° C. for 1 hour. Thereafter, the cells were fixed by 60-minute incubation at room temperature in a 4% paraformaldehyde solution. After washing with PBS 3 times, the nuclei were stained with DAPI (1/3000 dilution) by 5-minute incubation at room temperature, followed by washing with PBS 4 times. Thereafter, observation was performed with a Zeiss LSM510 meta confocal laser scanning microscope. The TMR-dextran taken up by the cells was observed as spots in cytoplasm. The macropinocytosis activity was measured based on the number of TMR-dextran spots per cell.

The results were shown based on the macropinocytosis activity (the number of TMR-dextran uptake per cell) under each condition, relative to the macropinocytosis activity under control conditions (DMSO was added alone) taken as 1.

Pharmacological Test. 6 (Evaluation on T Lymphocyte Migration)

Lymphocyte migration plays key roles in immune responses. T cell stimulation by chemokines, such as CCL21, induces actin cytoskeletal remodeling through Rac activation. This drives the cells to migrate towards the source of chemokines. To activate Rac in lymphocytes, the function of DOCK2 is indispensable, and migration of DOCK2-deficient T cells is thus significantly impaired (NPL 4). In contrast, DOCK1 is not expressed in T cells, and lymphocyte migration does not depend on the function of DOCK1.

Therefore, the use of various pyridinone compounds in this assay system enables cell-level verification of DOCK1 selectivity.

Mouse spleen cells at a cell concentration of $1\times10^7$ cells/mL were precultured at 37° C. for 1 hour in 0.5% BSA-containing RPMI-1640 (Transwell medium) containing DMSO alone or DMSO in which each pyridinone compound was dissolved at a predetermined concentration.

Subsequently, 500 µL of Transwell medium containing 300 ng/mL of CCL21 and DMSO in which each pyridinone compound was dissolved at a predetermined concentration was added to a 24-well plate. Then, Transwell inserts (Corning, pore size: 5 µm) were placed in the wells, into which the precultured cells were loaded at $1\times10^6$ cells/100 µL.

After 2-hour incubation at 37° C., the cells that migrated to the lower chamber were collected and stained with PE-labeled anti-Thy1.2 antibody (53-2-1, BD Pharmingen) and APC-labeled anti-B220 antibody (RA-6B-2, eBioscience). The percentage (%) of the migrated cells was calculated by dividing the number of Thy1.2$^+$ cells (T cells) in the lower chamber by the number of Thy1.2$^+$ cells (T cells) placed into the Transwell inserts.

As a control, spleen cells from a DOCK2-deficient mouse obtained in accordance with the method disclosed in NPL 4 were stimulated with CCL21 as described above.

Pharmacological Test (Effect on Viability of Lymphocytes)

$1\times10^6$ mouse spleen cells were suspended in 100 µL of RPMI-1640 medium containing 0.5% BSA, and DMSO in which each pyridinone compound was dissolved at a predetermined concentration of DMSO alone was added thereto to a final DMSO concentration of 0.2%. After 1-hour culture at 37° C., 2 µL of a propidium iodide staining solution (BD Pharmingen) was added and incubated on ice for 30 minutes, followed by flow cytometry analysis. The percentage (%) of the viable cells under each condition was calculated, considering negative cells to be viable cells.

Pharmacological Test 8 (Experiment for Inhibition of Lung Metastasis of Mouse Melanoma Cells)

Mouse melanoma B16F10 cells suspended in 200 µL of PBS(−) were injected (2.5 or $5\times10^5$ cells per mouse) into the tail vein of C57BL/6 mice (6 weeks old, female). TS45 was added to a liquid mixture of PBS/CremophorEL/ethanol (6:1:1) at 3 mg/300 µL, and 200 µL of the resulting mixture was injected into the tail vein of each mouse. For a control group, an equivalent amount of a solvent (a liquid mixture of PBS/CremophoreEL/ethanol (6:1:1)) alone was administered. The administration was performed 4 times in total: immediately before the cell transplantation, and day 1, day 3, and day 5 after the transplantation. Fourteen days after the first administration, the lung was excised from each mouse, and the number of tumor metastatic foci at the lung surface was counted.

Pharmacological Test Results 1

Figure 1:
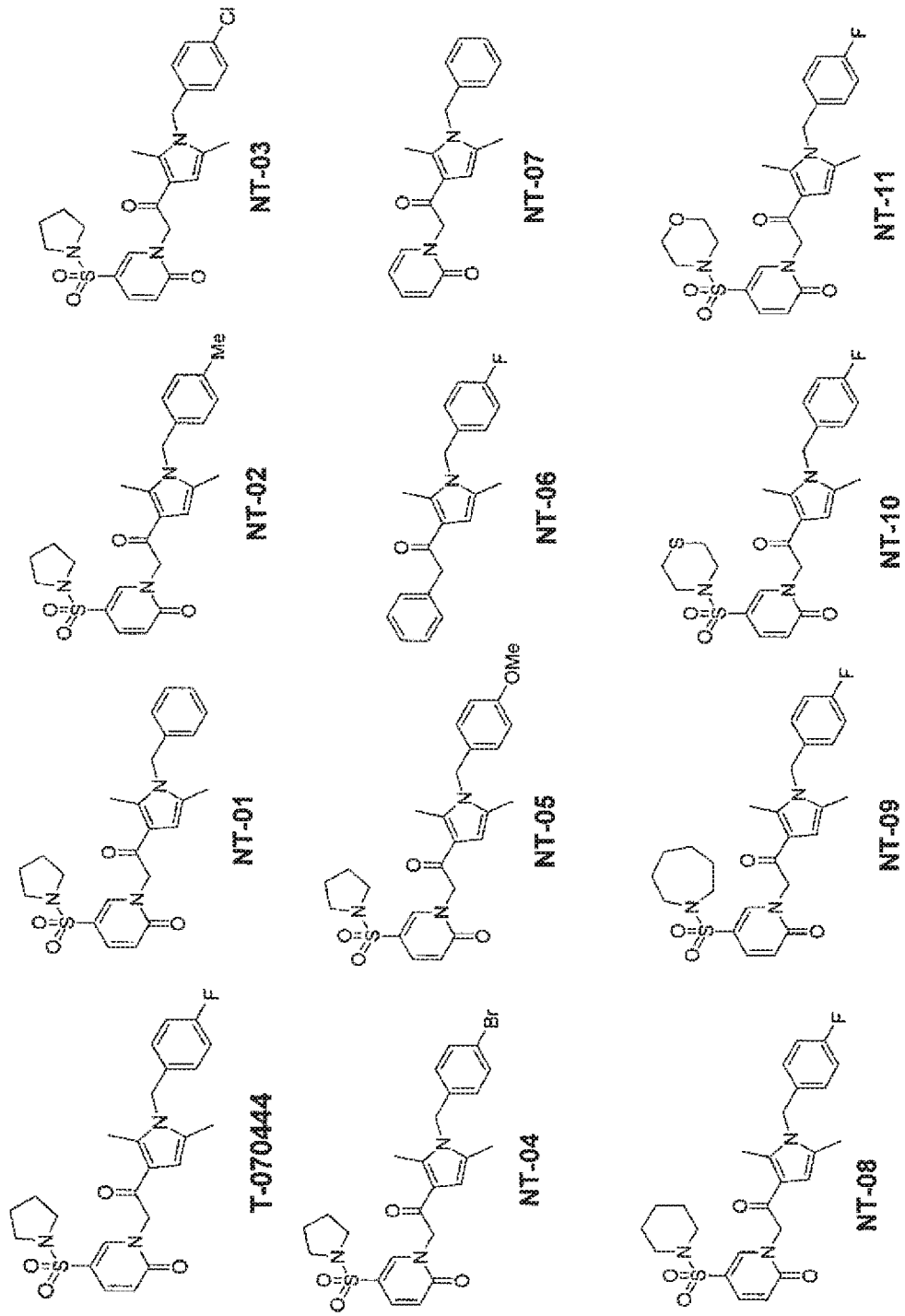
FIG. 1 shows the chemical structures of the pyridinone compounds of the present invention.
Figure 2:
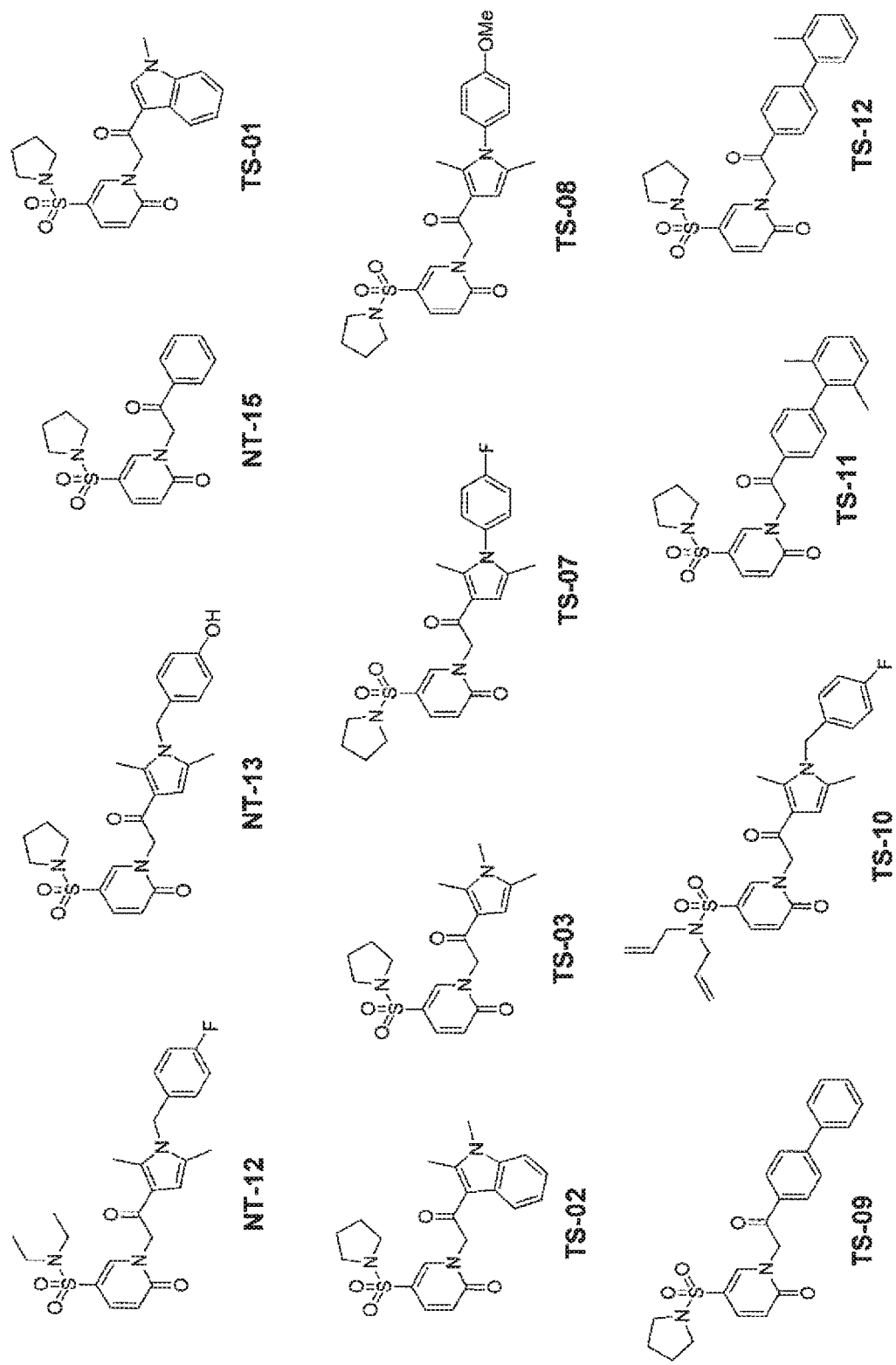
FIG. 2 shows the chemical structures of the pyridinone compounds of the present invention.
Figure 3:
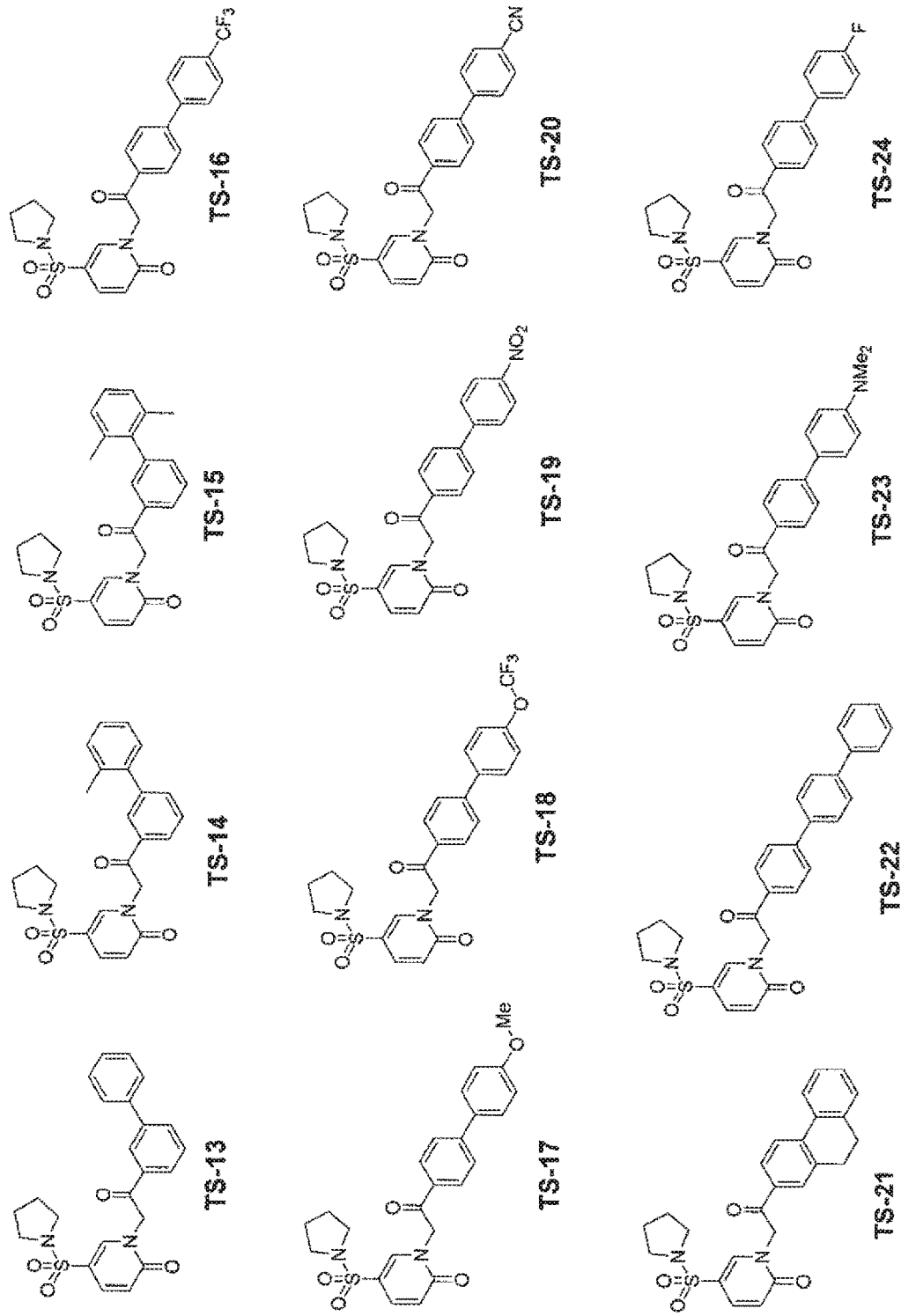
FIG. 3 shows the chemical structures of the pyridinone compounds of the present invention.
Figure 4:
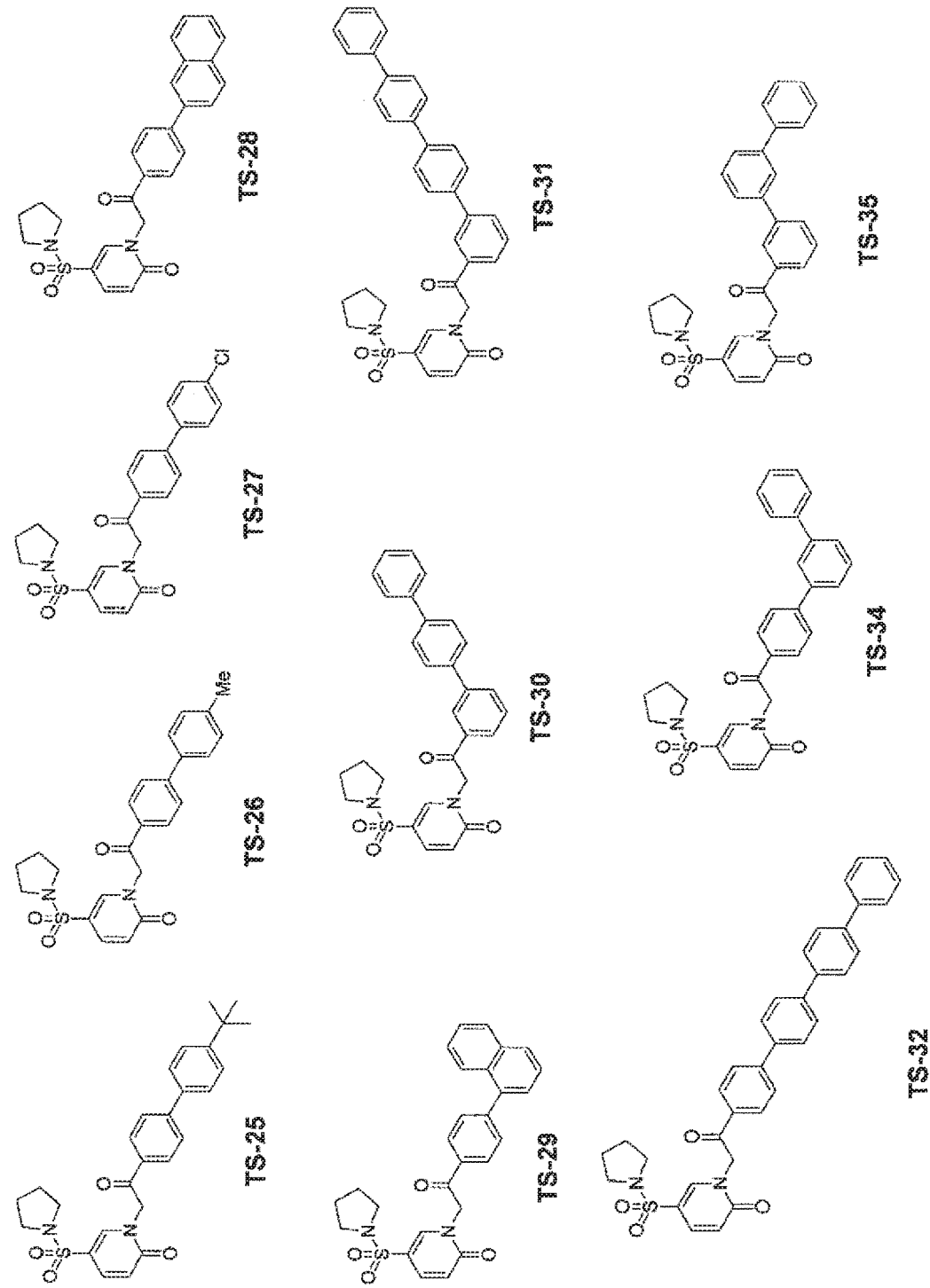
FIG. 4 shows the chemical structures of the pyridinone compounds of the present invention.
Figure 5:
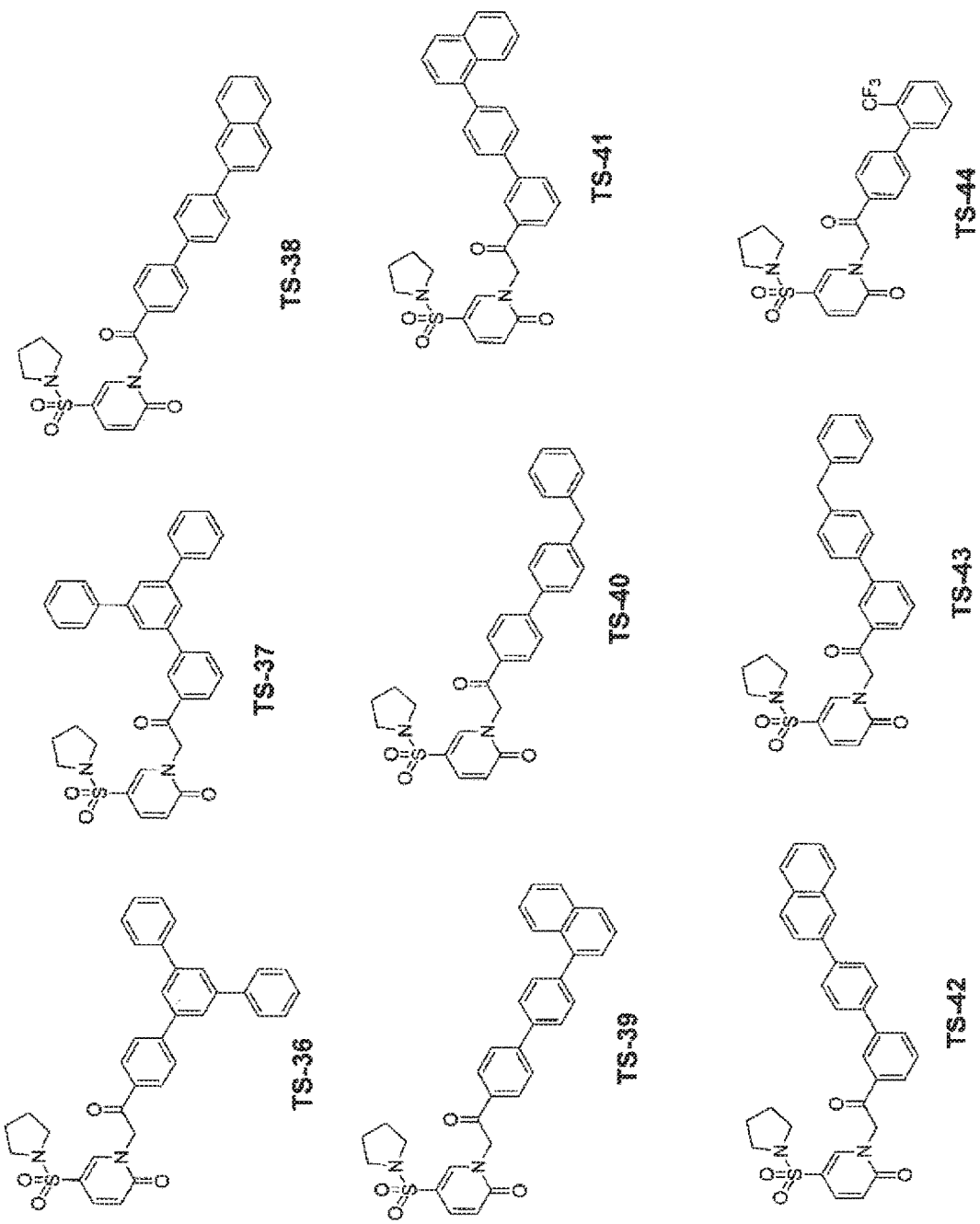
FIG. 5 shows the chemical structures of the pyridinone compounds of the present invention.
Figure 6:
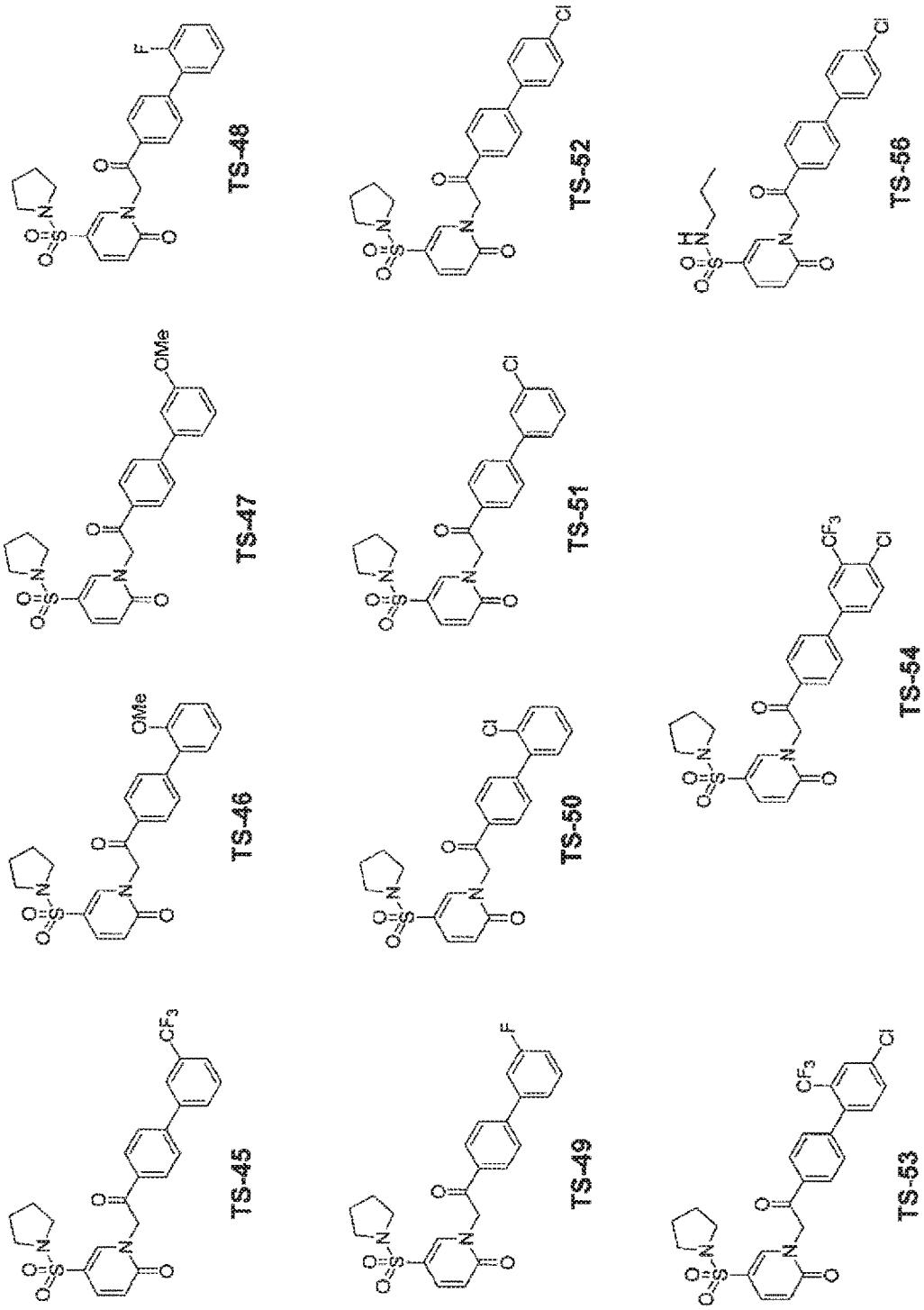
FIG. 6 shows the chemical structures of the pyridinone compounds of the present invention.
Figure 7:
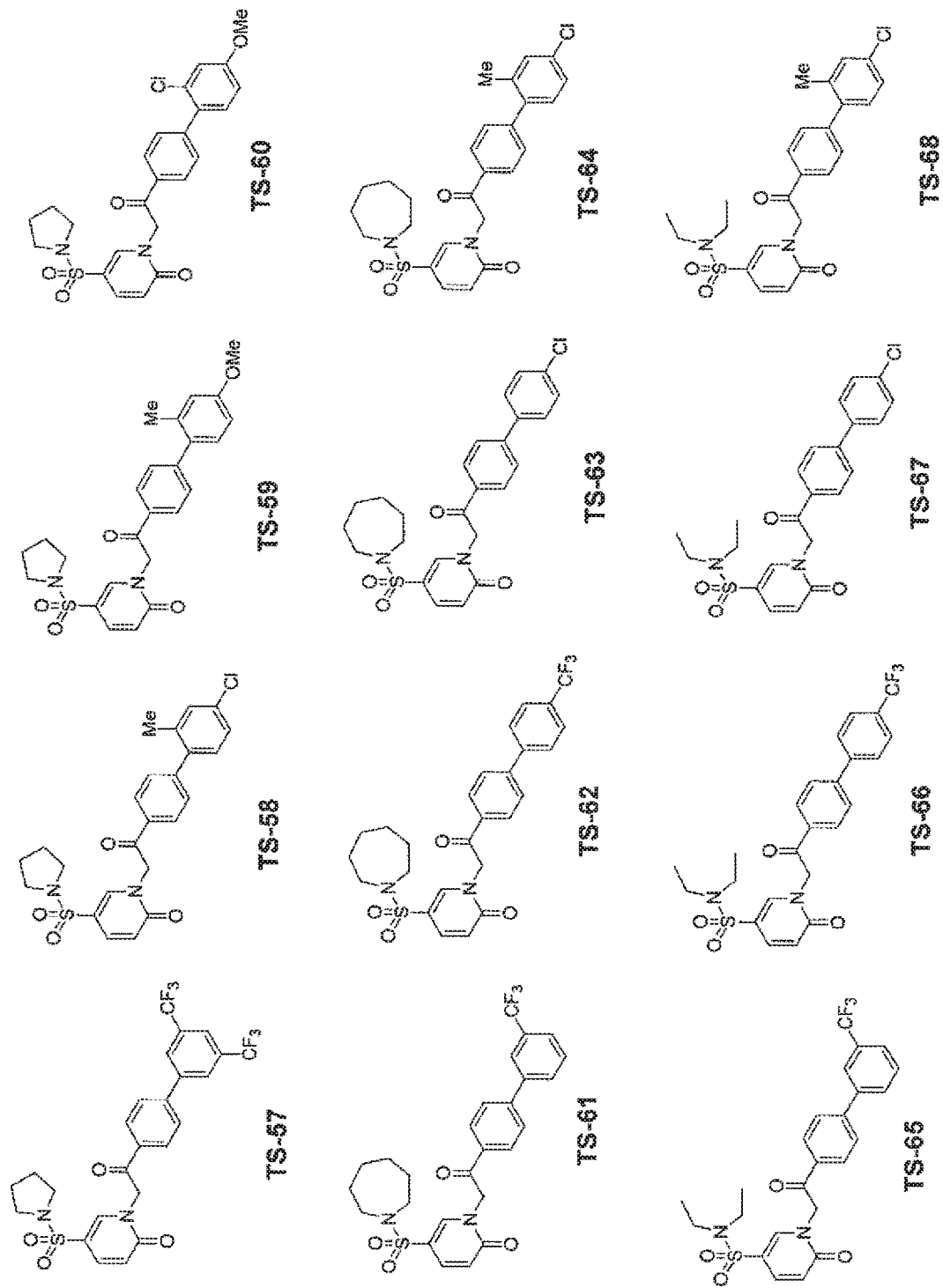
FIG. 7 shows the chemical structures of the pyridinone compounds of the present invention.
Figure 8:
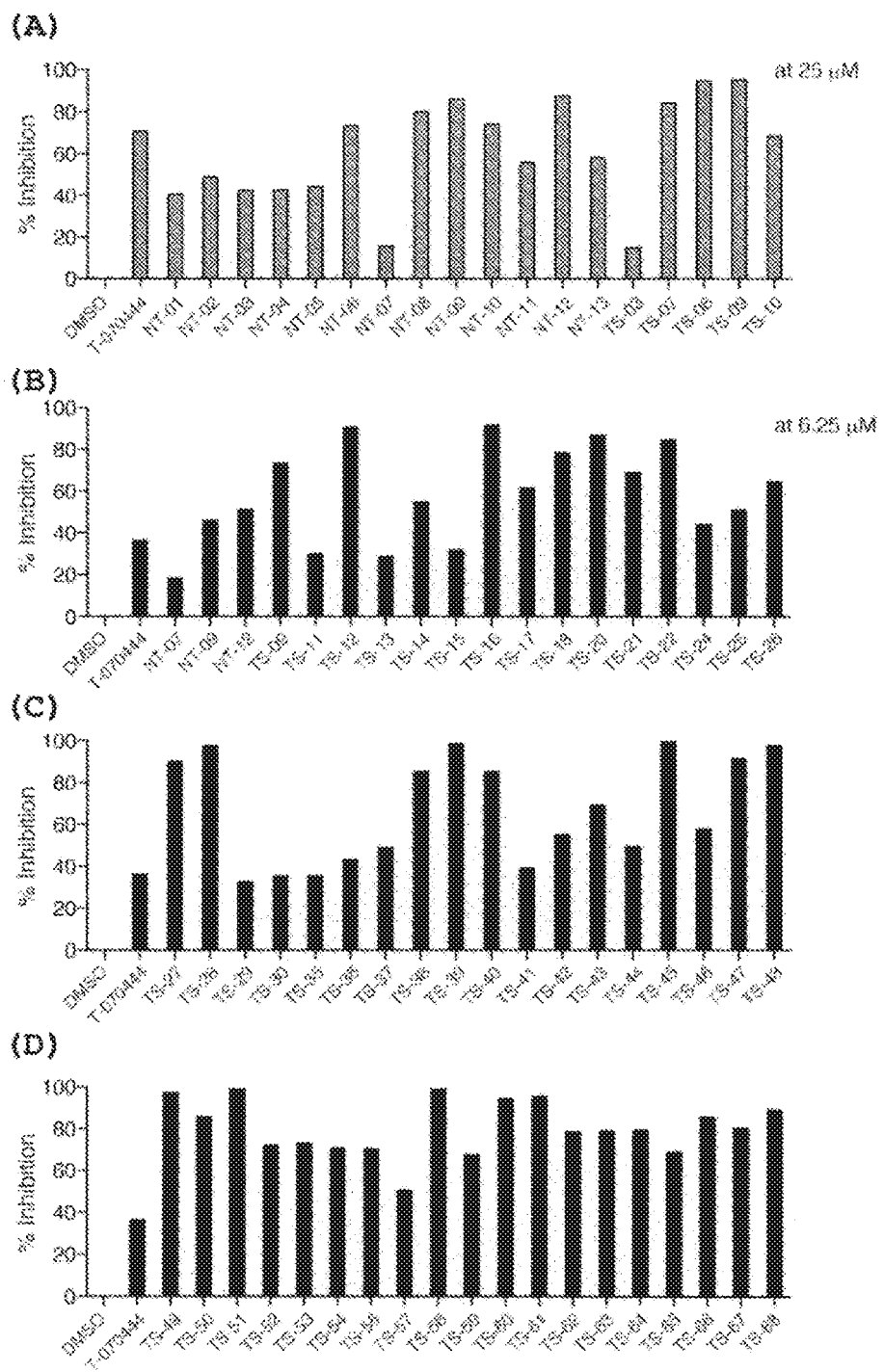
FIG. 8 is graphs showing the screening results obtained using as an index the inhibitory effect of the pyridinone compounds of the present invention on cancer cell (3LL) invasion.

The pyridinone compounds produced as described above were subjected to screening by using the method described in the Pharmacological Test 2 (Cellular Invasion Inhibition Assay) section above. The figure shows the concentrations of the pyridinone compounds used. FIG. 8 shows the results. In the graphs of the figure, the vertical axis represents percent inhibition (%: Inhibition); a higher value indicates a higher inhibitory activity.

These experimental results reveal that the pyridinone compounds of the present invention inhibit cancer cell invasion. Cancer cell invasion is believed to be a part of the mechanism of cancer cell metastasis. Thus, the pyridinone compounds of the present invention are clarified to be effective in the treatment and/or prevention of a metastatic cancer.

Pharmacological Test Results 2

The pyridinone compounds above were subjected to screening by using the method described in the Pharmacological Test 3 (Inhibition of Cellular Anchorage Independent Growth) section. The figure shows the concentrations of the pyridinone compounds used. FIG. 9 shows the results. In the graphs of the figure, the vertical axis represents percent inhibition (%: Inhibition); a higher value indicates a higher inhibitory activity.

Loss of anchorage dependence in cells is believed to be an index of oncogenic transformation of cells. Thus, the pyridinone compounds of the present invention are effective in the treatment and/or prevention of not only a metastatic cancer but also cancer cells.

Pharmacological Test Results 3

The pyridinone compounds above were subjected to screening by using the method described in the Pharmacological Test 1 (in vitro GEF Assay) section above. FIG. 10 shows the results. The vertical axis of the graphs in the figure represents the ratio of $IC_{50}$ value. The black bars represent the $IC_{50}$ value for DOCK1 relative to the $IC_{50}$ value for DOCK2, while the white bars represent the $IC_{50}$ value for DOCK1 relative to $IC_{50}$ value for DOCK5. "ND" in the figure indicates that either of the $IC_{50}$ values resulted in 300 µM or more.

It was clarified that the pyridinone compounds of the present invention exhibit, with selectivity to DOCK1, GEF inhibitory activity comparable to or more than that of CPYPP, which is known as a DOCK inhibitor (GEF inhibitor).

Based on the experimental results above, further experiments were conducted targeting some compounds from among the pyridinone compounds produced above.

Pharmacological Test Results 4

Together with CPYPP, four pyridinone compounds, T-070444, TS-09, TS-28, and TS-45, were subjected to Pharmacological Test 1 (in vitro GEF Assay) again. FIGS. 11(A)-(F) show the results.

The above four pyridinone compounds were confirmed to have a higher inhibitory activity against DOCK1 than the inhibitory activity against DOCK2 or DOCK5. Of the above compounds, TS-45 and TS-28 in particular had a high selectivity to DOCK1. In contrast, CPYPP had an effect on DOCK1, DOCK2, and DOCK5, and showed no selectivity in terms of GEF inhibition.

Accordingly, the four different pyridinone compounds were clarified to have excellent selectivity to DOCK1.

Pharmacological Test Results 5

Ten pyridinone compounds, T-070444, TS-09, TS-16, TS-27, TS-28, TS-44, TS-45, TS-47, TS-49, and TS-50, were subjected to Pharmacological Test 2 (Cellular Invasion Inhibition Assay) again. The figure shows the concentrations of the pyridinone compounds used. FIG. 12(A) shows the results.

In FIGS. 12(A)-(D), the vertical axis represents percent cell invasion (Invasion, %); a lower value indicates a more excellent inhibitory activity. The ten different pyridinone compounds above were all confirmed to significantly inhibit cancer cell (3LL) invasion, compared to DMSO used as a control. In particular, TS-16, TS-28, and TS-45 clearly exhibited a significantly excellent inhibitory effect.

FIG. 12(B) shows the results of cancer cell invasion inhibitory activity when TS-28 and TS-45 were used at various concentrations. The results indicate that both of these pyridinone compounds inhibit cancer cell invasion in a concentration-dependent manner. Further, as shown in the figure, the $IC_{50}$ value for TS-45 calculated based on this inhibition experiment was 3.0 μM, and the $IC_{50}$ value for TS-28 was 5.6 μM, which indicate excellent inhibitory activity, as with the $IC_{50}$ values calculated based on the GEF inhibitory activity above.

Further, the same experiment was performed, except that the cancer cells above were changed from 3LL cells to HT-1080 cells, i.e., a human fibrosarcoma cell line. The figure shows the concentrations of the pyridinone compounds used. FIG. 12(C) shows the results. The results indicate that both TS-45 and TS-28 also inhibit HT-1080 cell invasion.

Further, the same experiment was performed, except that the cancer cells above were changed from 3LL cells to DLD-1 cells, i.e., a human colon cancer cell line. The figure shows the concentrations of the pyridinone compounds used. FIG. 12(D) shows the results. The results indicate that TS-45 also inhibits DLD-1 cell invasion.

Pharmacological Test Results 6

Two pyridinone compounds, TS-28 and TS-45, were subjected to Pharmacological Test 3 (Inhibition of Cellular Anchorage Independent Growth) again. FIG. 13 shows the results.

The results indicate that both of these pyridinone compounds inhibit 3LL cell anchorage-independent growth in a concentration-dependent manner.

Pharmacological Test Results 7

Two pyridinone compounds, T-070444 and TS-45, were subjected to Pharmacological Test 4 (Experiment on Inhibition of Ruffle Formation). FIG. 14 shows the results.

As already reported in NPL 2, although the peripheral ruffle formation occurs, dorsal ruffle formation is impaired in MEFs from DOCK1 knockout mouse (D1KOMEFs).

CPYPP, which shows the inhibitory activity with non-selectivity among DOCK-A subfamily members, i.e., DOCK1, DOCK2, and DOCK5, inhibited both peripheral ruffle formation and dorsal ruffle formation. In the pyridinone compounds of the present invention, such as T-070444, however, the peripheral ruffle formation occurred in a similar manner to that of the control while the dorsal ruffle formation was significantly inhibited. These results have the same tendency as in the D1KOMEFs above.

Accordingly, it was clarified at the cellular level (in vivo level) that the pyridinone compounds of the present invention inhibit the GEF activity while identifying DOCK1 and DOCK5.

Pharmacological Test Results 8

Two pyridinone compounds, TS-28 and TS-45, were subjected to Pharmacological Test 5 (Experiment of Inhibition of Macropinocytosis. FIG. 15 shows the results.

TS-28 and TS-45 were confirmed to inhibit macropinocytosis in 3LL cells and HT-1080 cells in a concentration-dependent manner. As described above, cancer cells are believed to employ macropinocytosis to actively take up amino acids etc., from the extracellular space and use them as metabolic components to thus sustain the cells themselves and/or achieve cell growth; thus, the pyridinone compounds of the present invention, which effectively inhibit this phenomenon, are useful in the treatment and/or prevention of cancer.

Pharmacological Test Results 9

Two pyridinone compounds, TS-28 and TS-45, were subjected to experiments for confirming Pharmacological Test 6 (Evaluation on T Lymphocyte Migration) and Pharmacological Test 7 (Effect on Viability of Lymphocytes). FIG. 16 shows the results.

FIG. 16(A) clearly indicates that TS-28 and TS-45 did not affect the CCL21-stimulated T cell migration. If the pyridinone compounds of the present invention affect the GEF activity of DOCK2, the same behavior as the migration of T cells from DOCK2 knockout-mouse should be observed as shown in the D2KO in the figure; however, it was not observed, and so these results indicate at the cellular level (in vivo level) that the pyridinone compounds of the present invention selectively inhibit the GEF activity of DOCK1.

Accordingly, it was clarified that the pyridinone compounds of the present invention can be used as an active ingredient of an anti-cancer agent with few side effects.

Further, as shown in (B) in the figure, it was clear that the pyridinone compounds of the present invention did not affect the viability of T cells. This also indicates that the pyridinone compounds of the present invention can be used as an active ingredient of an anti-cancer agent with few side effects.

Pharmacological Test Results 10

TS-45, a pyridinone compound of the present invention, was subjected to Pharmacological Test 8 (Experiment for Inhibition of Lung Metastasis of Mouse Melanoma Cells). FIGS. 17(A)-(D) show the results.

The results shown in FIG. 17(B) reveal that the melanoma cells administered to mice were significantly inhibited from undergoing metastasis to the lung. This indicates that the pyridinone compounds of the present invention have inhibitory effects on cancer cell metastasis. Further, the results shown in FIG. 17(C) reveal that the administration at a dose of about 0.2 mg to a mouse would reduce the number of cells that underwent metastasis to the lung to about 20%. Further, the results shown in FIG. 17(D) reveal that the mouse body weight was not affected by administration or dose of TS-45.

Accordingly, TS-45 was clarified to be an anti-cancer agent with few side effects, i.e., an excellent compound that is effectively used in the treatment or prevention of a metastatic cancer.

The invention claimed is:

1. A method of screening for a substance as a candidate for an active ingredient of anti cancer drugs,
   the method comprising the following steps 1 to 3:
   step 1 of adding test substances to cells;
   step 2 of measuring the target function, which is a function of inhibition of DOCK1 function in the cells, and the control function, which is both a function of inhibition of DOCK2 function and a function of inhibition of DOCK5 function in the cells, and
   step 3 of identifying a substance as a candidate of an active ingredient of anti-cancer drugs, if the target function of the test substance measured in step 2 is greater than the control function of the same test substance measured in step 2,
   wherein steps 1 to 3 above comprise the following:
      the cells to which the test substances are added in step 1 are invasive cells, the target function measured in step 2 is to inhibit the invasiveness of the cells after the addition of the test substances to the cells, and substances that inhibit the invasiveness of the cells by the addition of the test substances are selected in step 3,
      the cells to which the test substances are added in step 1 are non-immune system cells, the target function measured in step 2 is both the dorsal ruffle formation and the peripheral ruffle formation in the cells, and substances that inhibit dorsal ruffle formation without affecting the peripheral ruffle formation in the cells by the addition of the test substances are selected in step 3, and
      the cells to which the test substances are added in step 1 are immune cells, the target function measured in step 2 is the migration response of the cells, and substances that do not affect the migration response of DOCK2 by the addition of the test substances are selected in step 3, and
   wherein the test substances for se in step 1 are selected by a screening method that comprises the following steps I to III:
      step I of separately contacting DHR-2 domain of DOCK1, DHR-2 domain of DOCK2, and DHR-2 domain of DOCK5 with test substances, and
      step II of measuring the target activity, which is the GEF activity by DHR-2 domain of DOCK1, and the control activity, which is both the GEF activity by DHR-2 domain of DOCK2 and the GEF activity by DHR-2 domain of DOCK5, using in vitro GEF assay; and
      step III of selecting, from the test substances, substances in which the target activity measured in step II is lower than the control activity as substances that inhibit the GEF activity, by DHR-2 domain of DOCK1 more strongly than the GEF activity by DHR-2 domain of DOCK2 and the GEF activity by DHR-2 domain of DOCK5.

2. The method according to claim 1, wherein the invasive cells are cancer cells.

3. The method according to claim 1, wherein the non-immune system cells are epithelial cells or fibroblasts.

4. The method according to claim 1, wherein the non-immune system ells are mouse embryonic fibroblasts.

5. The method according to claim 1, wherein the immune cells are lymphocytes.

6. A method of screening for a substance as a candidate for an active ingredient of anti-cancer drugs, the method comprising the following steps 1 to III and steps 1 to 4:
   step I of separately contacting DHR-2 domain of DOCK1, DHR-2 domain of DOCK2, and DHR-2 domain of DOCK5 with test substances;
   step II of measuring the target activity, which is the GEF activity of DOCK1, and the control activity, which is both the GEF activity by DHR-2 domain of DOCK2 and the GEF activity by DHR-2 domain of DOCK5, using in vitro GEF assay;
   step III of selecting, from the test substances, substances in which the target activity measured in step II is lower than the control activity as substances that inhibit the GEF activity by DHR-2 domain of DOCK1 more strongly than the GEF activity by DHR-2 domain of DOCK2 and the GEF activity by DHR-2 domain of DOCK5;
   step 1 of adding the substances selected in step HI to cells;
   step 2 of measuring the target function, which is a function of inhibition of DOCK1 function in the cells, and the control function, which is both a function of inhibition of DOCK2 function and a function of inhibition of DOCK5 function in the cells, and
   step 3 of identifying a substance as a candidate of an active ingredient of anti-cancer drugs if the target function of the test substance measured in step 2 is greater than the control function of the same test substance measured in step 2,
   wherein steps 1 to 3 above comprise the following:
      the cells to which the test substances are added in step 1 are invasive cells, the target function measured in step 2 is to inhibit the invasiveness of the cells after the addition of the test substances to the cells, and substances that inhibit the invasiveness of the cells by the addition of the test substances are selected in step 3,
      the cells to which the test substances are added in step 1 are non-immune system cells, the target function measured in step 2 is both the dorsal ruffle formation and the peripheral ruffle formation in the cells, and substances that inhibit dorsal ruffle formation without affecting the peripheral ruffle formation in the cells by the addition of the test substances are selected in step 3, and
      the cells to which the test substances are added in step 1 are immune cells, the target function measured in step 2 is the migration response of the cells, and substances that do not affect the migration response of DOCK2 by the addition of the test substances are selected in step 3, and
   providing the selected substance as a candidate of an active ingredient of anti-cancer drugs.

7. A method for treating cancer in a subject, comprising the step of administering the active ingredient obtained by the method of claim 1 to a subject suffering from cancer.

8. The method according to claim 7, wherein the active ingredient has an effect of selectively inhibiting GEF activity of DOCK1.

9. The method according to claim 7, wherein the cancer is a metastatic cancer.

10. A method for treating cancer in a subject, comprising the step of administering the active ingredient obtained by the method of claim 6 to a subject suffering from cancer.

11. The method according to claim 10, wherein the active ingredient has an effect of selectively inhibiting GEF activity of DOCK1.

12. The method according to claim 10, wherein the cancer is a metastatic cancer.

13. The method according to claim 8, wherein the cancer is a metastatic cancer.

14. The method according to claim 1,
wherein in steps II and III,
an $IC_{50}$ value for the GEF activity by DHR-2 domain of DOCK1 ($IC_{50}$ for DOCK1), an $IC_{50}$ value for the GEF activity by DHR-2 domain of DOCK2 ($IC_{50}$ for DOCK2), and an $IC_{50}$ value for the GEE activity by DHR-2 domain of DOCK5 ($IC_{50}$ for DOCK5) are measured, the ratio of the $IC_{50}$ for DOCK2 to the $IC_{50}$ for DOCK1 ($IC_{50}$ ratio D2/D1), and the ratio of the $IC_{50}$ for DOCK5 to the $IC_{50}$ for DOCK1 ($IC_{50}$ ratio D5/D1) are determined, and test substances that have the $IC_{50}$ ratio D2/D1 equal to or greater than the $IC_{50}$ ratio D1/D1 of CPYPP, and the $IC_{50}$ ratio D5/D1 equal to or greater than the $IC_{50}$ ratio D5/D1 of CPYPP, are selected,
with the proviso that the CPYPP is 4-[3-(2-Chlorophenyl)-2-propen-1-ylidene]-1-phenyl-3,5-pyrazolidinedione, which is a known DOCK inhibitor.

15. The method according to claim 14, wherein the test substances selected in the steps above have the $IC_{50}$ for DOCK1 of less than 300 μM, the $IC_{50}$ for DOCK2 of less than 300 μM, and the $IC_{50}$ for DOCK5 of less than 300 μM.

16. The method according to claim 6,
wherein in steps II and III,
an $IC_{50}$ value for the GEF activity by DHR-2 domain of DOCK1 ($IC_{50}$ for DOCK1), an $IC_{50}$ value for the GEF activity by DHR-2 domain of DOCK2 ($IC_{50}$ for DOCK2), and an $IC_{50}$ value for the GEF activity by DHR-2 domain of DOCK5 ($IC_{50}$ for DOCK5) are measured, the ratio of the $IC_{50}$ for DOCK2 to the $IC_{50}$ for DOCK1 ($IC_{50}$ ratio D2/D1), and the ratio of the $IC_{50}$ for DOCK5 to the $IC_{50}$ for DOCK1 ($IC_{50}$ ratio D5/D1) are determined, and
test substances that have the $IC_{50}$ ratio D2/D1 equal to or greater than the $IC_{50}$ ratio D2/D1 of CPYPP, and the $IC_{50}$ ratio D5/D1 equal to or greater than the $IC_{50}$ ratio D5/D1 of CPYPP, are selected,
with the proviso that the CPYPP is 4-[3-(2-Chlorophenyl)-2-propen-1-ylidene]-1-phenyl-3,5-pyrazolidinedione, which is a known DOCK inhibitor.

17. The method according to claim 16, wherein the test substances selected in the steps above have the $IC_{50}$ for DOCK1 of less than 300 μM, the $IC_{50}$ for DOCK2 of less than 300 μM, and the $IC_{50}$ for DOCK5 of less than 300 μM.

* * * * *